(12) United States Patent
Tun et al.

(10) Patent No.: US 12,421,562 B2
(45) Date of Patent: Sep. 23, 2025

(54) FECAL MICROBIAL BIOMARKERS FOR NON-ALCOHOLIC FATTY LIVER DISEASE

(71) Applicant: The University Of Hong Kong, Hong Kong (CN)

(72) Inventors: Hein Min Tun, Hong Kong (CN); Sai Sai Zhang, Hong Kong (CN); Hau Tak Chau, Hong Kong (CN); Fung Yu Huang, Hong Kong (CN); Man Fung Yuen, Hong Kong (CN); Wai Kay Seto, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 0 days.

(21) Appl. No.: 17/716,619

(22) Filed: Apr. 8, 2022

(65) Prior Publication Data

US 2022/0333163 A1 Oct. 20, 2022

Related U.S. Application Data

(60) Provisional application No. 63/172,900, filed on Apr. 9, 2021.

(51) Int. Cl.

| | | |
|---|---|---|
| *C12Q 1/68* | (2018.01) | |
| *A61K 35/741* | (2015.01) | |
| *A61K 35/747* | (2015.01) | |
| *A61P 1/16* | (2006.01) | |
| *C12Q 1/6883* | (2018.01) | |
| *C12Q 1/689* | (2018.01) | |
| *A61K 35/00* | (2006.01) | |
| *C12Q 1/686* | (2018.01) | |

(52) U.S. Cl.
CPC ............ *C12Q 1/689* (2013.01); *A61K 35/741* (2013.01); *A61K 35/747* (2013.01); *A61P 1/16* (2018.01); *C12Q 1/6883* (2013.01); *A61K 2035/115* (2013.01); *C12Q 1/686* (2013.01); *C12Q 2600/158* (2013.01)

(58) Field of Classification Search
CPC .............................. C12Q 1/689; A61K 35/741
See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 2019/0127781 A1* | 5/2019 | Yooseph | ................. G16H 50/20 |
| 2022/0333163 A1* | 10/2022 | Tun | ..................... A61K 35/744 |

FOREIGN PATENT DOCUMENTS

WO    WO-2017184899 A1 * 10/2017    ........... C12Q 1/6883

OTHER PUBLICATIONS

Agrimonti et al., 2019. Application of real-time PCR (qPCR) for characterization of microbial populations and type of milk in dairy food products. Critical Reviews in Food Science and Nutrition, 59(3), pp. 423-442. (Year: 2019).*
Aron-Wisnewsky et al., 2020. Nonalcoholic fatty liver disease: modulating gut microbiota to improve severity?. Gastroenterology, 158(7), pp. 1881-1898. (Year: 2020).*
Bajaj et al., 2014. Altered profile of human gut microbiome is associated with cirrhosis and its complications. Journal of hepatology, 60(5), pp. 940-947. (Year: 2014).*
Boursier et al., 2016. The severity of nonalcoholic fatty liver disease is associated with gut dysbiosis and shift in the metabolic function of the gut microbiota. Hepatology, 63(3), pp. 764-775. (Year: 2016).*
Delroisse et al., 2008. Quantification of *Bifidobacterium* spp. and *Lactobacillus* spp. in rat fecal samples by real-time PCR. Microbiological research, 163(6), pp. 663-670. (Year: 2008).*
Karaaslan et al., 2016. *Lactococcus lactis* spp lactis infection in infants with chronic diarrhea: two cases report and literature review in children. The Journal of Infection in Developing Countries, 10(03), pp. 304-307. (Year: 2016).*
Kubota et al. (2010). Detection of human intestinal catalase-negative, Gram-positive cocci by rRNA-targeted reverse transcription-PCR. Appl. Environ. Microbiol. 76, 5440-5451. (Year: 2010).*
Lelouvier et al., 2016. Changes in blood microbiota profiles associated with liver fibrosis in obese patients: a pilot analysis. Hepatology, 64(6), pp. 2015-2027. (Year: 2016).*
Loomba et al., 2017. Gut microbiome-based metagenomic signature for non-invasive detection of advanced fibrosis in human nonalcoholic fatty liver disease. Cell metabolism, 25(5), pp. 1054-1062. (Year: 2017).*
Maruo et al., 2006. Monitoring the cell number of *Lactococcus lactis* subsp. cremoris FC in human feces by real-time PCR with strain-specific primers designed using the RAPD technique. International journal of food microbiology, 110(1), pp. 69-76. (Year: 2006).*
Odamaki et al., 2011. Novel multiplex polymerase chain reaction primer set for identification of *Lactococcus* species. Letters in applied microbiology, 52(5), pp. 491-496. (Year: 2011).*
Ozaki et al., 2018. The effects of fermented milk containing *Lactococcus lactis* subsp. cremoris FC on defaecation in healthy young Japanese women: a double-blind, placebo-controlled study. International Journal of Food Sciences and Nutrition, 69(6), pp. 762-769. (Year: 2018).*

(Continued)

*Primary Examiner* — Gary Benzion
*Assistant Examiner* — Olayinka A Oyeyemi
(74) *Attorney, Agent, or Firm* — Pabst Patent Group LLP

(57) ABSTRACT

Disclosed are microbial biomarkers and methods for accurate non-invasive diagnosis of non-alcoholic fatty liver disease (NAFLD) in subjects. The microbial biomarkers include *Lactococcus lactis* as well as its strains and subspecies. The microbial biomarkers include *Dorea* sp. 5-2. The methods include measuring abundance or copy number of the one or more microbial biomarkers in a sample from the subject. The sample may be bodily fluid, mucus, or stool. Also described are methods of treating a subject with NAFLD by administering to the subject a composition containing *Lactococcus lactis* and/or *Dorea* sp. 5-2.

21 Claims, 18 Drawing Sheets

Specification includes a Sequence Listing.

(56) References Cited

OTHER PUBLICATIONS

Quigley, E.M., 2013. Gut bacteria in health and disease. Gastroenterology & hepatology, 9(9), p. 560. (Year: 2013).*
Segata et al., 2012. Metagenomic microbial community profiling using unique clade-specific marker genes. Nature methods, 9(8), pp. 811-814. (Year: 2012).*
Scorletti et al., 2018. Design and rationale of the INSYTE study: a randomised, placebo controlled study to test the efficacy of a synbiotic on liver fat, disease biomarkers and intestinal microbiota in non-alcoholic fatty liver disease. Contemporary Clinical Trials, 71, pp. 113-123. (Year: 2018).*
Song et al., 2020. Microbial niches in raw ingredients determine microbial community assembly during kimchi fermentation. Food Chemistry, 318, p. 126481. (Year: 2020).*
Tsuji et al., 2018. Counting the countless: bacterial quantification by targeting rRNA molecules to explore the human gut microbiota in health and disease. Frontiers in microbiology, 9, p. 1417. (Year: 2018).*
Youn et al., 2020. Gut-Microbial and-Metabolomic Signatures in the Prevention of Non-Alcoholic Fatty Liver Disease by Lactobacillus Lactis and Pediococcus Pentosaceus. (Year: 2020).*
Delik et al., 2022. Metagenomic identification of gut microbiota distribution on the colonic mucosal biopsy samples in patients with non-alcoholic fatty liver disease. Gene, 833, 146587, pp. 1-9. (Year: 2022).*
Mbaye et al., 2023. Limosilactobacillus fermentum, Lactococcus lactis and Thomasclavelia ramosa are enriched and Methanobrevibacter smithii is depleted in patients with non-alcoholic steatohepatitis. Microbial Pathogenesis, 106160, pp. 1-8. (Year: 2023).*
Allegretti, et al., "The evolution of the use of faecal microbiota transplantation and emerging therapeutic indications", Lancet, 394(10196):420-431 (2019).
Bang and Cho, "Comorbidities and Metabolic Derangement of NAFLD", J Lifestyle Med., 5(1):7-13 (2015).
Bashiardes, et al., "Non-alcoholic fatty liver and the gut microbiota", Mol Metab., 5(9):782-794 (2016).
Britton, et al., "Microbiotas from Humans with Inflammatory Bowel Disease Alter the Balance of Gut Th17 and RORγt+ Regulatory T Cells and Exacerbate Colitis in Mice", Immunity, 50:212-224 e214 (2019).
Browning, et al., "Prevalence of hepatic steatosis in an urban population in the United States: impact of ethnicity", Hepatology, 40(6):1387-1395 (2004).
Calinescu, et al., "Carboxymethyl high amylose starch (CM-HAS) as excipient for *Escherichia coli* oral formulations", Eur J Pharm Biopharm., 60(1):53-60 (2005).
Cani, et al., "Role of gut microflora in the development of obesity and insulin resistance following high-fat diet feeding", Pathol Biol. (Paris), 56(5):305-9 (2008).
Chalasani, et al., "The diagnosis and management of non-alcoholic fatty liver disease: practice Guideline by the American Association for the Study of Liver Diseases, American College of Gastroenterology, and the American Gastroenterological Association", Hepatology, 55(6):2005-23 (2012).
Chen, et al., "Lean NAFLD: A Distinct Entity Shaped by Differential Metabolic Adaptation", Hepatology (Baltimore, MD), 71(4):1213-1227 (2020).
Chen, et al., "SOAPnuke: a MapReduce acceleration-supported software for integrated quality control and preprocessing of high-throughput sequencing data", Gigascience, 7(1):1-6 (2018).
Conner, et al., "Detection of sickle cell BetaS-globin allele by hybridization with synthetic oligonucleotides", PNAS, 80(1):278-282 (1983).
Craven, et al., "Allogenic Fecal Microbiota Transplantation in Patients with Nonalcoholic Fatty Liver Disease Improves Abnormal Small Intestinal Permeability: A Randomized Control Trial", Am J Gastroenterol, 115(7):1055-1065 (2020).

De Vadder, et al., "Microbiota-generated metabolites promote metabolic benefits via gut-brain neural circuits", Cell, 156(1-2):84-96 (2014).
Del Chierico, et al., "Gut microbiota profiling of pediatric nonalcoholic fatty liver disease and obese patients unveiled by an integrated metaomics-based approach", Hepatology, 65(2):451-464 (2017).
Eslam, et al., "A new definition for metabolic dysfunction-associated fatty liver disease: An international expert consensus statement", J Hepatol., 73:202-209 (2020).
Fan, et al., "New trends on obesity and NAFLD in Asia", Journal of Hepatology; 67(4):862-873 (2017).
Feldman, et al., "Clinical and Metabolic Characterization of Lean Caucasian Subjects with Non-alcoholic Fatty Liver", Am J Gastroenterol., 112(1):102-110 (2017).
Franzosa, et al., "Species-level functional profiling of metagenomes and metatranscriptomes" Nat Methods, 15(11):962-968 (2018).
Gotoh, et al., "A dose-finding study for a supplement containing *Lactococcus lactis* subsp. cremoris FC in healthy adults with mild constipation", Biosci Microbiota Food Health; 39(1):19-22 (2020).
Govander, et al., "A review of the advancements in probiotic delivery: Conventional vs. non-conventional formulations for intestinal flora supplementation", AAPS PharmSciTech, 15(1):29-43 (2014).
Grattepanche, et al., "Quantification by real-time PCR of *Lactococcus lactis* subsp. cremoris in milk fermented by a mixed culture", Applied Microbiology and Biotechnology, 66(4):414-421 (2005).
Hakansson and Molin, "Gut microbiota and inflammation", Nutrients, 3(6):637-682 (2011).
Hay, et al., "Abnormal bacterial colonization of the genital tract and subsequent preterm delivery and late miscarriage", BMJ, 308(6924):295-298 (1994).
Hoyles, et al., "Molecular phenomics and metagenomics of hepatic steatosis in non-diabetic obese women", Nat Med., 24(7):1070-1080 (2018).
Hu, et al., "Intestinal microbiome and NAFLD: molecular insights and therapeutic perspectives", J Gastroenterol., 55(2):142-158 (2020).
Ivanov, et al., "Induction of intestinal Th17 cells by segmented filamentous bacteria", Cell, 139(3):485-98 (2009).
Jeznach-Steinhagen, et al., "Dietary and Pharmacological Treatment of Nonalcoholic Fatty Liver Disease", Medicina (Kaunas), 55(5):166 (2019).
Kameyama and Itoh, "Intestinal colonization by a Lachnospiraceae bacterium contributes to the development of diabetes in obese mice", Microbes Environ., 29(4):427-430 (2014).
Karlas et al., "Individual patient data meta-analysis of controlled attenuation parameter (CAP) technology for assessing steatosis", J Hepatol., 66:1022-1030 (2017).
Kazankov, et al., "The role of macrophages in nonalcoholic fatty liver disease and nonalcoholic steatohepatitis", Nat Rev Gastroenterol Hepatol., 16(3):145-159 (2019).
Kleiner, et al., "Design and Validation of a Histological Scoring System for Nonalcoholic Fatty Liver Disease.", Hepatology, 41(6):1313-1321 (2005).
Klijn, et al., "Detection and Characterization of Lactose-Utilizing *Lactococcus* spp. in Natural Ecosystems", Applied and Environmental Microbiology, 61(2):788-792 (1995).
Landegren, et al., "A ligase-mediated gene detection technique", Science, 241(4869):1077-80 (1988).
Laroute, et al., "From Genome to Phenotype: An Integrative Approach to Evaluate the Biodiversity of Lactococcus lactis", Microorganisms, 5(27):1-17 (2017).
Larrieta, et al., "Pharmacological concentrations of biotin reduce serum triglycerides and the expression of lipogenic genes", Eur J Pharmacol., 644(1-3):263-268 (2010).
Lazic, et al., "What exactly is 'N' in cell culture and animal experiments?", PLoS Biol., 16:e2005282 (2018).
Ley, et al., "Microbial ecology: human gut microbes associated with obesity", Nature, 444(7122):1022-3 (2006).
Li, et al., "Probiotics and antibodies to TNF inhibit inflammatory activity and improve nonalcoholic fatty liver disease", Hepatology, 37(2):343-50 (2003).

(56) References Cited

OTHER PUBLICATIONS

Li, et al., "The Role of Vitamins in the Pathogenesis of Non-alcoholic Fatty Liver Disease", Integr Med Insights, 11:19-25 (2016).
Liu, et al., "Gut Microbiome Fermentation Determines the Efficacy of Exercise for Diabetes Prevention", Cell Metab, 31(1):77-91 (2020).
Loguercio, et al., "Beneficial effects of a probiotic VSL#3 on parameters of liver dysfunction in chronic liver diseases", J Clin Gastroenterol., 39(6):540-3 (2005).
Lozupone, et al., "Diversity, stability and resilience of the human gut microbiota", Nature, 489(7415):220-230 (2012).
Mansouri, et al., "Mitochondrial Dysfunction and Signaling in Chronic Liver Diseases", Gastroenterology, 155(3):629-647 (2018).
Masarone, et al., "Role of Oxidative Stress in Pathophysiology of Nonalcoholic Fatty Liver Disease", Oxid Med Cell Longev., 2018:9547613 (2018).
Mouries et al., "Microbiota-driven gut vascular barrier disruption is a prerequisite for non-alcoholic steatohepatitis development", Journal of Hepatology, 71(6):1216-1228 (2019).
Naudin, et al., "*Lactococcus lactis* Subspecies cremoris Elicits Protection Against Metabolic Changes Induced by a Western-Style Diet", Gastroenterology, 159(2):639-651 (2020).
Nguyen, et al., "Association Between Sulfur-Metabolizing Bacterial Communities in Stool and Risk of Distal Colorectal Cancer in Men", Gastroenterology, 158(5):1313-1325 (2020).
O'Toole, et al., "Next-generation probiotics: the spectrum from probiotics to live biotherapeutics.", Nat Microbiol., 2:17057 (2017).
Paulino, et al., "Molecular analysis of fungal microbiota in samples from healthy human skin and psoriatic lesions.", J. Clin. Microbiol., 44(8):2933-2941 (2006).
Peng, et al., "IDBA-UD: a de novo assembler for single-cell and metagenomic sequencing data with highly uneven depth", Bioinformatics, 28(11):1420-1428 (2012).
Pittman, "Fecal Microbiota and Screening for Colorectal Cancer" Clin Chem., 64(9):1273-1274 (2018).
Raman, et al., "Fecal microbiome and volatile organic compound metabolome in obese humans with nonalcoholic fatty liver disease", Clin Gastroenterol Hepatol., 11(7):868-875.e861-863 (2013).
Ravussin, et al., "Responses of gut microbiota to diet composition and weight loss in lean and obese mice", Obesity (Silver Spring), 20(4):738-747 (2012).
Revilla-Monsalve, et al., "Biotin supplementation reduces plasma triacylglycerol and VLDL in type 2 diabetic patients and in nondiabetic subjects with hypertriglyceridemia", Biomed Pharmacother., 60(4):182-185 (2006).
Ridaura, et al., "Gut microbiota from twins discordant for obesity modulate metabolism in mice.", Science, 341(6150):1241214 (2013).
Saiki, et al., "A Novel Method for the Detection of Polymorphic Restriction Sites by Cleavage of Oligonucleotide Probes: Application to Sickle-Cell Anemia" Nature Bio/Technology, 3:1008-1012 (1985).
Sampson, et al., "Gut Microbiota Regulate Motor Deficits and Neuroinflammation in a Model of Parkinson's Disease," Cell, 167(6):1469-1480 e1412 (2016).
Satiaputra, et al., "Mechanisms of biotin-regulated gene expression in microbes", Synth Syst Biotechnol., 1(1):17-24 (2016).
Sato, et al., "Paneth cells constitute the niche for Lgr5 stem cells in intestinal crypts" Nature; 469:415-418 (2011).

Schleifer, et al., "Transfer of *Streptococcus lactis* and Related *Streptococci* to the Genus *Lactococcus* gen. nov", Syst Appl Microbiol., 6:183-195(1985).
Schnabl and BRENNER, "Interactions between the intestinal microbiome and liver diseases", Gastroenterology, 146(6):1513-1524 (2014).
Segata, et al., "Metagenomic biomarker discovery and Explanation", Genome Biol., 12(6):R60 (2011).
Segata, et al., "Metagenomic microbial community profiling using unique clade-specific marker genes", Nat Methods, 9(8):811-814 (2012).
Sepp, et al., "The association of gut microbiota with body weight and body mass index in preschool children of Estonia", Microb Ecol Health Dis., 24:19231 (2013).
Seto and Yuen, "Nonalcoholic fatty liver disease in Asia: emerging perspectives", J Gastroenterol., 52(2):164-174 (2017).
Shimizu, et al., "Lactococcus lactis cholangitis and bacteremia identified by MALDI-TOF mass spectrometry: A case report and review of the literature on Lactococcus lactis infection", J Infect Chemother., 25(2):141-146 (2019).
Song, et al., "A review on Lactococcus lactis: from food to factory", Microb Cell Fact., 16:(55):1-15 (2017).
Staley, et al., Diurnal cycling of rhizosphere bacterial communities is associated with shifts in carbon metabolism, Microbiome, 5(1):65 (2017).
Tannahill, et al., "Succinate is an inflammatory signal that induces IL-1β through HIF-1α", Nature; 496(7444):238-242 (2013).
Thomsen et al., "Topical Clindamycin Treatment of Acne: Clinical, Surface Lipid Composition, and Quantitative Surface Microbiology Response", Arch. Dermatol., 116:1031-1034 (1980).
Van Mastrigt, et al., "Large plasmidome of dairy *Lactococcus lactis* subsp. lactis biovar diacetylactis FM03P encodes technological functions and appears highly unstable", (2018), BMC Genomics, 19(1):620 (2018).
Vrieze, et al., "Transfer of intestinal microbiota from lean donors increases insulin sensitivity in individuals with metabolic syndrome", Gastroenterology, 143(4):913-916 (2012).
Walter, et al., "Establishing or Exaggerating Causality for the Gut Microbiome: Lessons from Human Microbiota-Associated Rodents", Cell, 180(2):221-232 (2020).
Williams, et al., Prevalence of nonalcoholic fatty liver disease and nonalcoholic steatohepatitis among a largely middle-aged population utilizing ultrasound and liver biopsy: a prospective study., Gastroenterology, 140(1):124-131 (2011).
Wong, et al., "Gavage of Fecal Samples From Patients With Colorectal Cancer Promotes Intestinal Carcinogenesis in Germ-Free and Conventional Mice", Gastroenterology, 153(6): 1621-1633 (2017).
Yadav, et al., "Effect of Dahi containing Lactococcus lactis on the progression of diabetes induced by a high-fructose diet in rats", Biosci Biotechnol Biochem., 70(5):1255-1258 (2006).
Yang, et al., "Establishing high-accuracy biomarkers for colorectal cancer by comparing fecal microbiomes in patients with healthy families", Gut Microbes, 11:918-929 (2020).
Zempleni and Mock, "Biotin biochemistry and human requirements", J Nutr Biochem.; 10(3):128-138 (1999).
Zhang, et al., "Ecological robustness of the gut microbiota in response to ingestion of transient food-borne microbes", The ISME journal, 10(9):2235-2245 (2016).

\* cited by examiner

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Synthetic sequence - forward primer for
      Lactococcus lactis

<400> SEQUENCE: 1
tgtcacaagc catgcgaaac                                                   20

<210> SEQ ID NO 2
<211> LENGTH: 21
<212> TYPE: DNA
<213> ORGANISM: Artificial Sequence
<220> FEATURE:
<223> OTHER INFORMATION: Synthetic sequence - reverse primer for
      Lactococcus lactis

<400> SEQUENCE: 2
cacgcaattg gttgatgaaa a                                                 21

<210> SEQ ID NO 3
<211> LENGTH: 21
<212> TYPE: DNA
<213> ORGANISM: Artificial Sequence
<220> FEATURE:
<223> OTHER INFORMATION: Synthetic sequence - forward primer for
      Lactococcus lactis (LL1)

<400> SEQUENCE: 3
agcagtaggg aatcttcggc a                                                 21

<210> SEQ ID NO 4
<211> LENGTH: 24
<212> TYPE: DNA
<213> ORGANISM: Artificial Sequence
<220> FEATURE:
<223> OTHER INFORMATION: Synthetic sequence - reverse primer for
      Lactococcus lactis (LL1)

<400> SEQUENCE: 4
gggtagttac cgtcacttga tgag                                              24

<210> SEQ ID NO 5
<211> LENGTH: 20
<212> TYPE: DNA
<213> ORGANISM: Artificial Sequence
<220> FEATURE:
<223> OTHER INFORMATION: Synthetic sequence - forward primer for
      Lactococcus lactis (LL2)

<400> SEQUENCE: 5
tgaagaattg atggaactcg                                                   20

<210> SEQ ID NO 6
<211> LENGTH: 18
<212> TYPE: DNA
<213> ORGANISM: Artificial Sequence
<220> FEATURE:
<223> OTHER INFORMATION: Synthetic sequence - reverse primer for
      Lactococcus lactis (LL2)

<400> SEQUENCE: 6
cattgtggtt caccgttc                                                     18

<210> SEQ ID NO 7
<211> LENGTH: 27
<212> TYPE: DNA
<213> ORGANISM: Artificial Sequence
<220> FEATURE:
<223> OTHER INFORMATION: Synthetic sequence - forward primer for
      Lactococcus lactis (LL3)

<400> SEQUENCE: 7
gttgtattag ctagttggtg aggtaaa                                          27

<210> SEQ ID NO 8
<211> LENGTH: 20
<212> TYPE: DNA
<213> ORGANISM: Artificial Sequence
<220> FEATURE:
<223> OTHER INFORMATION: Synthetic sequence - reverse primer for
      Lactococcus lactis (LL3)

<400> SEQUENCE: 8
gttgagccac tgccttttac                                                  20

<210> SEQ ID NO 9
<211> LENGTH: 16
<212> TYPE: DNA
<213> ORGANISM: Artificial Sequence
<220> FEATURE:
<223> OTHER INFORMATION: Synthetic sequence - forward primer for
      subspecies lactis (lactis1)

<400> SEQUENCE: 9
tgtcacaagc catgcg                                                      16

<210> SEQ ID NO 10
<211> LENGTH: 18
<212> TYPE: DNA
<213> ORGANISM: Artificial Sequence
<220> FEATURE:
<223> OTHER INFORMATION: Synthetic sequence - reverse primer for
      subspecies lactis (lactis1)

<400> SEQUENCE: 10
cacgcaattg gttgaaaa                                                    18

<210> SEQ ID NO 11
<211> LENGTH: 28
<212> TYPE: DNA
<213> ORGANISM: Artificial Sequence
<220> FEATURE:
<223> OTHER INFORMATION: Synthetic sequence - forward primer for
      subspecies lactis (lactis2)

<400> SEQUENCE: 11
ttaattcaac ctggagacac agtcttag                                         28

<210> SEQ ID NO 12
<211> LENGTH: 25
<212> TYPE: DNA
<213> ORGANISM: Artificial Sequence
<220> FEATURE:
<223> OTHER INFORMATION: Synthetic sequence - reverse primer for
      subspecies lactis (lactis2)

<400> SEQUENCE: 12
ctatcagcga tttcacggaa cttag                                            25

```
<210> SEQ ID NO 13
<211> LENGTH: 33
<212> TYPE: DNA
<213> ORGANISM: Artificial Sequence
<220> FEATURE:
<223> OTHER INFORMATION: Synthetic sequence - forward primer for
      subspecies cremoris (cremoris)

<400> SEQUENCE: 13
gatgaagatt ggtgcttgca ccaatttgaa gag                               33

<210> SEQ ID NO 14
<211> LENGTH: 20
<212> TYPE: DNA
<213> ORGANISM: Artificial Sequence
<220> FEATURE:
<223> OTHER INFORMATION: Synthetic sequence - reverse primer for
      subspecies cremoris (cremoris)

<400> SEQUENCE: 14
cctctcaggt cggctatgta                                              20

<210> SEQ ID NO 15
<211> LENGTH: 21
<212> TYPE: DNA
<213> ORGANISM: Artificial Sequence
<220> FEATURE:
<223> OTHER INFORMATION: Synthetic sequence - forward primer for
      subspecies lactis biovar diacetylactis (citP)

<400> SEQUENCE: 15
ggagttggtg ctggtattgt g                                            21

<210> SEQ ID NO 16
<211> LENGTH: 18
<212> TYPE: DNA
<213> ORGANISM: Artificial Sequence
<220> FEATURE:
<223> OTHER INFORMATION: Synthetic sequence - reverse primer for
      subspecies lactis biovar diacetylactis (citP)

<400> SEQUENCE: 16
ctgctattac agggttgg                                                18
```

FECAL MICROBIAL BIOMARKERS FOR NON-ALCOHOLIC FATTY LIVER DISEASE

CROSS-REFERENCE TO RELATED APPLICATIONS

This application claims priority to and the benefit of U.S. Provisional Application No. 63/172,900, filed on Apr. 9, 2021, which is incorporated herein and by reference in its entirety.

REFERENCE TO SEQUENCE LISTING

The Sequence Listing submitted Apr. 8, 2022, as a text file named "UHK_01037_ST25.txt", created on Apr. 8, 2022, and having a size of 4,302 bytes is hereby incorporated by reference pursuant to 37 C.F.R. § 1.52(e)(5).

FIELD OF THE INVENTION

This invention is generally directed to biomarkers and methods for non-invasive diagnosis or treatment of liver diseases.

BACKGROUND OF THE INVENTION

Metabolic syndrome encompasses a set of interlinked chronic diseases, including hypertension, diabetes, dyslipidemia, nonalcoholic fatty liver disease (NAFLD) and cardiovascular disease. Despite the longstanding notion that obesity is the origin of metabolic syndrome, increased incidence in lean individuals suggests that obesity is a symptom rather than a cause of metabolic syndrome. A historic analysis of 36,377 US adults showed higher body mass index (BMI) in 2008 compared to 1975, despite similar caloric intake and activity level, pointing to the notion that changes in overall dietary composition may be responsible for rising rates of metabolic syndrome. Interestingly, in females, an inverse relationship has been reported between caloric intake and BMI, where lower total caloric intake corresponded with a higher BMI, even after accounting for individuals who were dieting for weight loss. This signifies a sexually dimorphic impact of caloric consumption on weight gain. Along with rising rates of obesity, the prevalence of NAFLD and type 2 diabetes has increased by 40% in Western societies in recent years, underscoring an urgent need for treatments to combat these conditions. Increasingly, investigations have shown a relationship between the intestinal microbiota and metabolic syndrome, with specific reports linking certain microbiome diversities (Nadin et al., *Gastroenterology*, 159:639-651 (2020)) to exacerbation of Western-style diet-induced systemic pathologies.

Non-alcoholic fatty liver disease (NAFLD) is the world's most common chronic liver disease, with a population-based prevalence of 24-46% in Western countries and 7.9-54% in Asia, affecting both lean and obese individuals, but lacking in viable therapeutic options. More recently, the gut microbiota has emerged as an important player in the pathogenesis of NAFLD. In general, NAFLD patients showed altered microbial composition, manifested as a decreased proportion of Oscillibacter, an increased proportion of *Roseburia, Robinsoniella, Dorea* and *Lactobacillus* via 16s rRNA sequencing. Microbial dysbiosis leads to the distinct shifts in bacterial products, including ethanol, lipopolysaccharides, short-chain fatty acids, conjugated bile acids, and trimethylamine N-oxide. These metabolites translocate into the portal vein through an impaired intestinal barrier ("leaky" gut), bind to specific toll-like receptors in the liver, and activate the proinflammatory pathways. While there has been evidence of an altered gut microbiota being associated with NAFLD, causality had not been established.

Despite the common association of *Lactococcus lactis* with dairy products, the bacterium was originally isolated from plants where it was believed to be dormant, and only became active and multiplied in the gastrointestinal tract after being consumed by ruminants Originating from the *streptococcus* genus and re-classified into the *Lactococcus* genus in 1985, *L. lactis* is divided into three subspecies namely *L. lactis* subsp. *lactis, L. lactis* subsp. *cremoris*, and *L. lactis* subsp. *hordniae*. Phenotypically, it is classified as a gram-positive, spherical, homolactate, non-sporulating, and facultative anaerobic gut bacteria with hundreds of strains and bio variants published to date (Song et al., *Microb Cell Fact*, 16:(55):1-15 (2017)).

The use of lactobacilli in patients with NAFLD has produced no evidence of a clinical benefit. A study using a type of VSL #3 mixture of three types of bacteria (lyophilized *bifidobacteria*, lactobacilli, and *Streptococcus thermophilus*) for 4 weeks in ob/ob mice showed a reduction in hepatic total fatty acid content and liver inflammation as well as an improvement in hepatic insulin resistance (Li et al., *Hepatology*, 37:343-50 (2003)). VSL #3R (Alfasigma USA, Inc.) is a probiotic medical food intended for the dietary management of ulcerative colitis (UC), irritable bowel syndrome (IBS), or an ileal pouch. Another study also provided the beneficial effects of a probiotic VSL #3 on parameters of liver dysfunction in chronic liver diseases. (Loguercio et al., *J Clin Gastroenterol.*, 39(6):540-3 (2005)). However, a subsequent trial on VSL #3 in patients with NAFLD was terminated in 2020 due to the lack of evidence of clinical benefit (NCT03511365).

In NAFLD, liver biopsy remains the gold standard for diagnosis. However, routine use of liver biopsy is limited by its invasive nature, risk of complications, cost, sampling error, and poor patient acceptance. This underscores an urgent need for non-invasive and accurate methods for disease detection.

There is a pressing need for diagnostic biomarkers to non-invasively detect NAFLD. There is also a need for effective treatments for NAFLD.

Therefore, it is the object of the present invention to provide biomarkers for non-invasive detection of NAFLD.

It is another object of the present invention to provide compositions and methods for treating NAFLD.

SUMMARY OF THE INVENTION

Described are compositions and methods for non-invasively detecting non-alcoholic fatty liver disease (NAFLD) in a subject. Also described are methods for preventing or treating NAFLD. The compositions typically include an effective amount of *Lactococcus lactis* and/or *Dorea* sp. 5-2. The compositions may include microorganisms from *L. lactis* subsp. *lactis, L. lactis* subsp. *cremoris, L. lactis* subsp. *hordniae, Lactococcus lactis* strains selected from the group consisting of CF102, 104, 109, MGYG-HGUT-00226, and *Lactococcus lactis, L. lactis* subsp. *lactis* strain CF111 or 112. In some aspects, the compositions do not contain *L. lactis* subsp. *cremoris*.

The compositions may include a mix of microorganisms having *Dorea* sp. 5-2 at a relative abundance of about 3%, or greater than about 3%, such as between about 3% and 6%, as measured by linear discriminant analysis (LDA). In some aspects, the composition may include a mix of microorganisms having *Lactococcus lactis* at a relative abundance of about 30% or greater than about 30%, such as between about 30% and 60%, as measured by LDA. In some aspects, the composition may include a mix of microorganisms having *Lactococcus lactis* at a relative abundance of about 30 copies of *Lactococcus lactis* DNA per ng bacterial DNA, or greater than about 30 copies of *Lactococcus lactis* DNA per ng bacterial DNA, as determined by quantitative polymerase chain reaction (qPCR). The compositions may include between $1.0 \times 10^{11}$-$1.0 \times 10^{13}$ colony forming units (CFU) of the microorganisms per ml of the composition or per mg of the composition.

Also described are methods of detecting NAFLD by
(a) measuring abundance or copy number of a microbial biomarker in a sample from the subject, and
(b) detecting NAFLD in the subject when
  (i) the abundance of the microbial biomarker in the sample is less than half or about half of the abundance of the microbial biomarker in a healthy control, and/or
  (ii) the number of copies of the microbial biomarker DNA in the sample is about 20 copies/ng bacterial DNA or below 20 copies/ng bacterial DNA.

In some forms, measuring comprises a linear discriminant analysis (LDA) to measure abundance. In some forms, measuring comprises a catalase activity test to measure the presence or absence of the catalase enzyme. In some forms, measuring comprises a quantitative PCR to measure copy number.

The step of measuring may be by LDA or by quantitative PCR using amplification primers containing the nucleic acid sequences of SEQ ID NO:1 and/or SEQ ID NO:2, SEQ ID NO:3 and/or SEQ ID NO:4; SEQ ID NO:5 and/or SEQ ID NO:6; SEQ ID NO:7 and/or SEQ ID NO:8; SEQ ID NO:9 and/or SEQ ID NO:10; SEQ ID NO:11 and/or SEQ ID NO:12; SEQ ID NO:15 and/or SEQ ID NO:16.

In some forms, measuring is by quantitative PCR using amplification primers comprising the nucleic acid sequence of (1) SEQ ID NO:1 and/or SEQ ID NO:2, (2) SEQ ID NO:3 and/or SEQ ID NO:4, (3) SEQ ID NO:5 and/or SEQ ID NO:6, (4) SEQ ID NO:7 and/or SEQ ID NO:8, (5) SEQ ID NO:9 and/or SEQ ID NO:10, (6) SEQ ID NO:11 and/or SEQ ID NO:12, (7) SEQ ID NO:13 and/or SEQ ID NO:14, and/or (8) SEQ ID NO:15 and/or SEQ ID NO:16.

In some forms, measuring is by quantitative PCR using amplification primers comprising the nucleic acid sequence of (1) SEQ ID NO:1 and/or SEQ ID NO:2. In some forms, measuring is by quantitative PCR using amplification primers comprising the nucleic acid sequence of (2) SEQ ID NO:3 and/or SEQ ID NO:4. In some forms, measuring is by quantitative PCR using amplification primers comprising the nucleic acid sequence of (3) SEQ ID NO:5 and/or SEQ ID NO:6. In some forms, measuring is by quantitative PCR using amplification primers comprising the nucleic acid sequence of (4) SEQ ID NO:7 and/or SEQ ID NO:8. In some forms, measuring is by quantitative PCR using amplification primers comprising the nucleic acid sequence of (5) SEQ ID NO:9 and/or SEQ ID NO:10. In some forms, measuring is by quantitative PCR using amplification primers comprising the nucleic acid sequence of (6) SEQ ID NO:11 and/or SEQ ID NO:12. In some forms, measuring is by quantitative PCR using amplification primers comprising the nucleic acid sequence of (7) SEQ ID NO:13 and/or SEQ ID NO:14. In some forms, measuring is by quantitative PCR using amplification primers comprising the nucleic acid sequence of (8) SEQ ID NO:15 and/or SEQ ID NO:16.

In some forms, when primers of more than one of (1), (2), (3), (4), (5), (6), (7), and (8) are used for quantitative PCR, a separate quantitative PCR reaction is performed for the primers used from different of (1), (2), (3), (4), (5), (6), (7), and (8). In some forms, when a separate quantitative PCR reaction is performed for the primers used from different of (1), (2), (3), (4), (5), (6), (7), and (8), the separate quantitative PCR reactions are performed in parallel. In some forms, when a separate quantitative PCR reaction is performed for the primers used from different of (1), (2), (3), (4), (5), (6), (7), and (8), the separate quantitative PCR reactions are performed sequentially. In some forms, separate quantitative PCR reactions are performed sequentially for primers of (1), primers of (2), (3), and/or (4), primers of (5), (6), and/or (7), and primers of (8), the separate quantitative PCR reactions are performed sequentially.

Typically, the method detects the microbial biomarker *Lactococcus lactis* or *Dorea* sp. 5-2. The method detects NAFLD in the subject when the number of *L. lactis* copies is about 20 copies of *Lactococcus lactis* DNA per ng bacterial DNA or below 20 copies of *Lactococcus lactis* DNA per ng bacterial DNA in the sample. The sample may be diluted or undiluted bodily fluid, mucus, or stool. The sample may be a diluted sample diluted at a ratio between about 1:5 and 1:500 (v/v) of the sample to a sample dilution buffer.

The subject may have one or more diseases, such as metabolic syndrome, type 2 diabetes mellitus, cardiovascular disease (CVD), and chronic kidney disease (CKD).

Also described are methods of treating NAFLD or preventing NAFLD in a subject. Typically, the method includes administering to the subject a composition containing an effective amount of *Lactococcus lactis* and/or *Dorea* sp. 5-2.

Also described are kits containing one or more compositions containing an effective amount of *L. lactis* and/or *Dorea*.

DETAILED DESCRIPTION OF THE INVENTION

I. Definitions

Figure 1A:
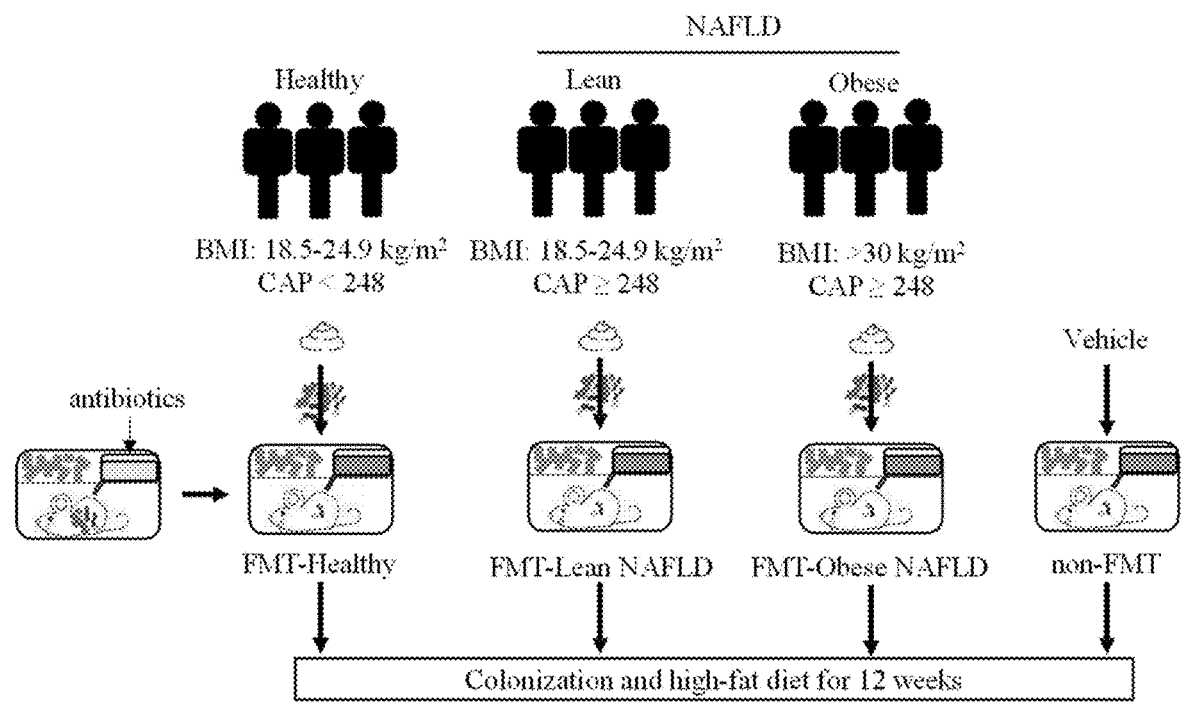
FIG. 1A is a diagram showing the experimental design for the FMT studies. Human feces from healthy donors, lean NAFLD donors and obese NAFLD donors were used to perform fecal microbiota transplantation without pooling. Antibiotic cocktail-treated mice were orally administrated with microbiota from healthy donors, lean NAFLD donors and obese NAFLD donors (FMT-HC, FMT-LN and FMT-ON) or vehicle (non-FMT). All mice were colonized for 12 weeks on a high-fat diet. BMI, body mass index; CAP, controlled attenuation parameter; FMT, fecal microbiota transplantation; HC, Healthy controls; LN, lean non-alcoholic fatty liver disease; NAFLD, non-alcoholic fatty liver disease; ON, obese non-alcoholic fatty liver disease.

As used herein, the term "biomarker" refers to a cellular, molecular, histologic, radiographic, and/or a physiologic characteristic that is measured as an indicator of normal biological processes, pathogenic processes, or responses to an exposure or intervention, including therapeutic interventions. The biomarker may be a diagnostic and/or or prognostic biomarker used for detecting a tissue state or disease, monitoring a tissue state or disease, and/or predicting tissue state or disease. For example, a measure of a biomolecule that is a biomarker may provide information about a tissue state as a diagnostic biomarker, as well as information about future changes in the tissue state as a prognostic biomarker. Other examples of biomarkers include body mass index (BMI) as a physiologic biomarker, or tissue elasticity as a radiographic biomarker, both of which may be diagnostic biomarkers and prognostic biomarkers.

As used herein, the term "non-invasive" or "non-invasively," in the context of detecting, refers to a mode of obtaining information about an organ of interest without physically taking a sample from the organ of interest, such as without a biopsy of the organ of interest. For example, non-invasively detecting NAFLD refers to detecting NAFLD without biopsy of the liver.

As used herein, the term "detect," "detecting," "determine" or "determining" generally refers to obtaining information. Detecting or determining can utilize any of a variety of techniques available to those skilled in the art, including for example specific techniques explicitly referred to herein. Detecting or determining may involve manipulation of a physical sample, consideration and/or manipulation of data or information, for example utilizing a computer or other processing unit adapted to perform a relevant analysis, and/or receiving relevant information and/or materials from a source. Detecting or determining may also mean comparing an obtained value to a known value, such as a known test value, a known control value, or a threshold value. Detecting or determining may also mean forming a conclusion based on the difference between the obtained value and the known value.

As used herein, the term "substantial" generally refers to a comparative degree, such as at least about 85-90%, preferably about 95% or more for substantial similarity, and less than 15%, preferably less than 10%, or less than 5% for substantial difference. In the context of purity, "substantially pure" refers to at least about 85-90%, about 90%, preferably about 95% or more purity.

As used herein, the term "purified" and like terms relate to the molecule or compound in a form that is substantially free (at least 60% free, preferably 75% free, and most preferably 90% free) from other components normally associated with the molecule or compound in a native environment.

As used herein, the term "isolated" refers to a degree of purity such that the isolated is substantially free of components occurring in a non-isolated state. In a context of isolated microbial biomarker, the isolated microbial biomarker is substantially free of other microbes occurring in a non-isolated state with the biomarker.

As used herein, the term "sensitivity" refers to the ability of a test to correctly identify true positives, i.e., subjects with NAFLD. For example, sensitivity can be expressed as a percentage, the proportion of actual positives which are correctly identified as such (e.g., the percentage of test subjects having NAFLD correctly identified by the test as having NAFLD). A test with high sensitivity has a low rate of false negatives, i.e., the cases with NAFLD not identified as such. Generally, the disclosed assays and methods have a sensitivity of at least about 70%, at least about 80%, at least about 85%, at least about 90%, at least 92%, at least 94%, at least 95%, at least 96%, at least 97%, at least 98%, at least 99%, or at least 100%.

As used herein, the term "specificity" refers to the ability of a test to correctly identify true negatives, i.e., the subjects without NAFLD. For example, specificity can be expressed as a percentage, the proportion of actual negatives which are correctly identified as such (e.g., the percentage of test subjects not having NAFLD correctly identified by the test as not having NAFLD). A test with high specificity has a low rate of false positives, i.e., the cases of individuals not having NAFLD but suggested by the test as having NAFLD. Generally, the disclosed methods have a specificity of at least about 60%, at least about 70%, at least about 80%, at least about 90%, at least 92%, at least 94%, at least 95%, at least 96%, at least 97%, at least 98%, at least 99%, or at least 100%.

As used herein, the term "accurate" refers to the ability of a test to provide results with high sensitivity and high specificity, such as with sensitivity over about 80% and specificity over about 60%, with sensitivity over about 85% and specificity over about 65%, or with sensitivity over about 90% and specificity over about 80%.

As used herein, the term "sample" refers to body fluids, body smears, cell, tissue, organ or portion thereof that is isolated from a subject. A sample may be a single cell or a plurality of cells. A sample may be a specimen obtained by biopsy (e.g., surgical biopsy). A sample may be cells from a subject that are or have been placed in or adapted to tissue culture. A sample may be one or more of cells, tissue, serum, plasma, urine, spittle, sputum, and stool. A sample may be one or more of a saliva, sputum, tear, sweat, urine, exudate, blood, serum, plasma, or a vaginal discharge.

As used herein, the terms "subject," "individual" or "patient" refer to a human or a non-human mammal. A subject may be a non-human primate, domestic animal, farm animal, or a laboratory animal. For example, the subject may be a dog, cat, goat, horse, pig, mouse, rabbit, or the like. The subject may be a human. The subject may be healthy, suffering from, or susceptible to a disease, disorder or condition. A patient refers to a subject afflicted with a disease or disorder. The term "patient" includes human and veterinary subjects.

A "control" sample or value refers to a sample that serves as a reference, usually a known reference, for comparison to a test sample. For example, a test sample can be taken from a test subject, and a control sample can be taken from a control subject, such as from a known normal (non-disease) individual. A control can also represent an average value gathered from a population of similar individuals, e.g., disease patients or healthy individuals with a similar medical background, same age, weight, etc. One of skill will recognize that controls can be designed for assessment of any number of parameters.

As used herein the terms "treatment" or "treating" refer to administering a composition to a subject or a system to treat one or more symptoms of a disease. The effect of the administration of the composition to the subject can be, but is not limited to, the cessation of a particular symptom of a condition, a reduction or prevention of the symptoms of a condition, a reduction in the severity of the condition, the complete ablation of the condition, a stabilization or delay of the development or progression of a particular event or characteristic, or minimization of the chances that a particular event or characteristic will occur.

As used herein, the terms "prevent" or "preventing" refer to: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein the terms "effective amount" and "therapeutically effective amount," used interchangeably, refer to the quantity necessary to render the desired therapeutic result. For example, an effective amount is a level effective to treat, cure, or alleviate the symptoms of a disease for which the composition and/or therapeutic agent, or pharmaceutical composition, is/are being administered. Amounts effective for the particular therapeutic goal sought will depend upon a variety of factors including the disease being treated and its severity and/or stage of development/progression; the bioavailability and activity of the specific compound and/or antineoplastic, or pharmaceutical composition, used; the route or method of administration and introduction site on the subject.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%.

II. Microbial Biomarkers for NAFLD

Biomarkers for non-invasively detecting NAFLD in a subject include microbial, molecular, radiographic, and/or a physiologic biomarker. The biomarkers may be used alone or in any combination. For example, any one or more of the microbial biomarkers may be used with any one or more of the radiographic biomarkers, and/or with any one or more physiologic biomarkers. In some embodiments, the one or more microbial biomarkers are used with one or more physiologic biomarkers, and/or with the one or more radiographic biomarkers, to detect NAFLD.

Described are microbial biomarkers for detecting and diagnosing NAFLD. The microbial biomarkers include microbes from host's microbiome and populating host's mucosal, fluid, and/or stool spaces. The microbial biomarkers typically include species *Lactococcus lactis* and *Dorea* sp. 5-2. These markers are typically negatively associated with NAFLD, especially with NAFLD with significant liver steatosis.

In some embodiments, the microbial biomarkers may be used with molecular biomarkers, such as glycated hemoglobin (HbA1c); high-density lipoprotein cholesterol (HDL-C); low-density lipoprotein cholesterol (LDL-C); total cholesterol (TC); triglycerides (TG); alanine aminotransferase (ALT); and aspartate transaminase (AST).

A. *Lactococcus lactis*

The *Lactococcus* genus, belonging to the phylum Firmicutes, is closely related to the *Streptococcus* genus, both members of the Streptococcaceae family, and has 11 species: *L. lactis, L. raffinolactis, L. garviae, L. plantarum, L. piscium, L. chungengensis, L. fujiensis, L. taiwanensis, L. formosensis* and two newly identified species *L. hircilactis* and *L. laudensis*. To date, *L. lactis* is the best known lactococcal species. It is one of the most frequently used microorganisms in the dairy industry and its use has the "generally recognized as safe" (GRAS) status. *L. lactis* is involved in the manufacture of various dairy products, both artisanal and industrial ones, such as (soft) cheese, buttermilk and sour cream. Its major role in dairy as dairy starter culture is to provide lactic acid at an efficient rate during milk fermentation.

*Lactococcus lactis* is a gram-positive, non-sporulating, aerotolerant bacteria belonging to the Streptococcaceae family. The species is divided into four subspecies, *lactis, cremoris, hordniae* and *tructae*, and one *diacetylactis* biovar.

The *Lactococcus lactis* and its subspecies include unique about 83 different strains extensively reviewed by Laroute (Laroute et al., *Microorganisms*, 5(27):1-17 (2017), incorporated herein in its entirety, and particularly for its disclosure of *Lactococcus lactis* strains), as well as *Lactococcus lactis* strains (CF102, 104, 109, MGYGHGUT-00226, and *Lactococcus lactis*) and two *Lactococcus lactis* subsp. *lactis* strains (CF111 and 112).

1. *Lactococcus lactis* as a Biomarker for NAFLD

The microbial marker may be *Lactococcus lactis*, its subspecies, and its strains. Preferably, the microbial biomarker includes *L. lactis* subsp. *lactis, L. lactis* subsp. *cremoris, L. lactis* subsp. *hordniae*. In some embodiments, the microbial biomarker does not include *L. lactis* subsp. *cremoris*. In some embodiments, the microbial biomarker includes *Lactococcus lactis* strains CF102, 104, 109, MGYG-HGUT-00226, and/or *Lactococcus lactis*, and *L. lactis* subsp. *lactis* strain CF111 or 112.

Typically, the microbial biomarker abundance and/or the microbial biomarker copy number in a population of microorganisms in a sample from a subject is measured and compared to the same in a sample from a healthy control. Typically, NAFLD is detected when the abundance of the microbial biomarker in the sample from the subject is less than half or is about half of the abundance of the microbial biomarker in the healthy control. Alternatively, the copy number of the microbial biomarker in a population of microorganisms in a sample from a subject is measured and compared to the same in a sample from a healthy control. Typically, NAFLD is detected when the number of copies of the microbial biomarker DNA in the sample is about 20 copies/ng bacterial DNA or is below 20 copies/ng bacterial DNA. For example, the number of *L. lactis* copies/ng bacterial DNA in a sample may be between about 1 copies/ng bacterial DNA and about 20 copies/ng bacterial DNA, such as between about 1 copies/ng bacterial DNA and about 15 copies/ng bacterial DNA, or between about 5 copies/ng bacterial DNA and about 15 copies/ng bacterial DNA, as measured by linear discriminant analysis (LDA).

B. *Dorea* sp. 5-2

*Dorea* sp. 5-2, with UniPort Taxon Identifier 1235798, is a bacterium classified under Bacteria, Firmicutes, Clostridia, Clostridiales, Lachnospiraceae, Dorea, *Dorea* sp. 5-2. The genus *Dorea* includes four known and classified species: *Candidatus Dorea massiliensis, Dorea formicigenerans, Dorea longicatena,* and *Dorea phocaeensis*. The genus *Dorea* also includes numerous unclassified species annotated as: *Dorea* sp., *Dorea* sp. 42_8, *Dorea* sp. 4_1_36 FAA, *Dorea* sp. 5-2, *Dorea* sp. AF24-7LB, *Dorea* sp. AF36-15AT, *Dorea* sp. AGR2135, *Dorea* sp. AM10-31, *Dorea* sp. AM13-35, *Dorea* sp. AM58-8, *Dorea* sp. BIOML-A1, *Dorea* sp. D27, *Dorea* sp. hmp_mda_pilot_jcvi_0005, *Dorea* sp. hmp_mda_pilot_jcvi_0013, *Dorea* sp. Marseille-P3386, *Dorea* sp. Marseille-P4042, *Dorea* sp. MC_33, *Dorea* sp. OM02-2LB, and *Dorea* sp. OM07-5.

Of these, *Dorea* sp. 5-2 was found to have negative association with development of NAFLD.

1. *Dorea* sp. 5-2 as a Biomarker for NAFLD

The microbial marker may be species of genus *Dorea*, their subspecies, and strains. In some embodiment, the microbial biomarker includes *Dorea* species *Candidatus Dorea massiliensis*, *D. formicigenerans*, *D. longicatena*, *D. phocaeensis*, *Dorea* sp. 42_8, *Dorea* sp. 4_1_36 FAA, *Dorea* sp. 5-2, *Dorea* sp. AF24-7LB, *Dorea* sp. AF36-15AT, *Dorea* sp. AGR2135, *Dorea* sp. AM10-31, *Dorea* sp. AM13-35, *Dorea* sp. AM58-8, *Dorea* sp. BIOML-A1, *Dorea* sp. D27, *Dorea* sp. hmp_mda_pilot_jcvi_0005, *Dorea* sp. hmp_mda_pilot_jcvi_0013, *Dorea* sp. Marseille-P3386, *Dorea* sp. Marseille-P4042, *Dorea* sp. MC_33, *Dorea* sp. OM02-2LB, and *Dorea* sp. OM07-5. Preferably, the microbial biomarker includes *Dorea* sp. 5-2.

Typically, the microbial biomarker abundance and/or the microbial biomarker copy number in a population of microorganisms in a sample from a subject is measured and compared to the same in a sample from a healthy control. Typically, NAFLD is detected when the abundance of the microbial biomarker in the sample from the subject is less than half or is about half of the abundance of the microbial biomarker in the healthy control. Alternatively, the copy number of the microbial biomarker in a population of microorganisms in a sample from a subject is measured and compared to the same in a sample from a healthy control. Typically, NAFLD is detected when the number of copies of the microbial biomarker DNA in the sample is at a relative abundance of about 3%, or less than about 3%, such as between about 0.1% and 3%, as measured by linear discriminant analysis (LDA).

C. Subject

The subjects benefiting from the disclosed methods may be humans, non-human primates, domestic animals, farm animals, or laboratory animals. For example, the subject may be a dog, cat, goat, horse, pig, mouse, rabbit, or the like. The subject may be a human. The subject may be healthy, suffering from, or susceptible to a disease, disorder or condition.

In subjects may have one or more of the diseases metabolic syndrome, type 2 diabetes mellitus, cardiovascular disease (CVD), and chronic kidney disease (CKD). Therefore, the method may detect NAFLD in patients with one or more of diseases metabolic syndrome, type 2 diabetes mellitus, CVD, and CKD.

The subject may be free of disease. The subject may have one or more of diseases metabolic syndrome, type 2 diabetes mellitus, CVD, and CKD. The subject may have metabolic syndrome with one or more of obesity, insulin resistance, diabetes mellitus, dyslipidemia, and hypertension. The subject may have diabetes, liver disease, or a combination of diabetes and liver disease. The subject may have type 2 diabetes. The subject may have NAFLD. The subject may have type 2 diabetes and NAFLD. The subject may or may not have nonalcoholic steatohepatitis (NASH).

D. Methods of Measuring Microbial Biomarker

The detection of the abundance or copy number of the microbial biomarker typically occurs in a sample with a plurality of microorganisms. The microbial biomarker may be a target microorganism, such as *L. lactis* or *Dorea* sp. 5-2. The abundance or the genome copy number of the target microorganism may be determined among a plurality of microorganisms using various methods known in the art. These methods include microbial 16s rRNA sequencing, sequence alignment and identification using numerous available sequence manipulation methods, including MEGAN, a metagenomic analysis tool with recent additions for phylogenetic comparisons and statistical analyses; STAMP, which does introduce a concept of 'biological relevance' in the form of confidence intervals; UniFrac, which compares sets of metagenomes at a strictly taxonomic level using phylogenetic distance; and MGRAST; ShotgunFunctionalizeR; mothur; and METAREP. All of these methods process metagenomic data using standard statistical tests (mainly t-tests with some modifications). (Segata et al., *Genome Biol;* 12:R60 (2011)). Additional methods include applying statistical tools to the sequence data to detect the degree of abundance as measured with LDA, as described in detail in Segata et al., *Genome Biol;* 12:R60 (2011).

Alternatively, the copy number of the target microbial biomarker may be obtained from amplification assays utilizing primers specific to the target microbial biomarker. The copy number can then be reported as copy/ng bacterial DNA.

1. Metagenomic Analyses Based on 16s rRNA Sequences and Linear Discriminant Analysis (LDA)

Typically, the method includes shotgun metagenomic sequencing, metagenomics analysis, and LDA, as described in Segata et al., *Genome Biol;* 12:R60 (2011).

An exemplary method may include extracting stool DNA using DNA extraction kits readily available in the art and subjecting the extracted DNA to library preparation. Library preparation and Illumina sequencing (such as with Paired-End sequencing of 150 bp on NovaSeq 6000) may be performed to generate sequence libraries. The libraries may then be processed to generate adapter ligated libraries, such as per protocol of KAPA Hyper Prep Kit (KR0961-V1.14). The adapter ligated library with a size range of 300-750 bp may be selected by dual-Solid Phase Reversible Immobilization method, followed by library enrichment via polymerase chain reaction (PCR). The enriched libraries may be validated by Fragment Analyzer (Agilent), Qubit and qPCR for quality control analysis. The libraries may be denatured and diluted to optimal concentration for sequencing.

Using software from Illumina (bcl2fastq), sequencing reads may be assigned to individual samples with each sample having an average throughput and a total throughput. Raw data may be pre-processed through quality control using SOAPnuke 2, and host-derived reads may be removed. The sequencing throughput for each sample may be rarefied to 35 million reads. Clean reads may be assembled using IDBA-UD 1.1.3 (Chen et al., *Gigascience;* 7:1-6 (2018), Peng et al., *Bioinformatics;* 28:1420-1428 (2012)) with default parameters. 16s genes may be predicted by barrnap 0.9 and compared statistically. Taxonomy profiling at different taxonomic levels may be performed with metaphlan v3 (Segata et al., *Nat Methods;* 9:811-814 (2012)). Analysis of α- and β-diversity in bacterial communities may be performed. Shannon index and Chao1 index may be calculated for α-diversity and richness analysis. Statistical method for data comparison may be applied. Ordination may be done by principal coordinate analysis (PCoA) with Bray-Curtis distance. Multivariate analysis may be performed using permutational multivariate analysis of variance.

Microbiota-based biomarker analysis may be performed with linear discriminant analysis (LDA) effect size (LEfSe) (Segata et al., *Genome Biol;* 12:R60 (2011)), a biomarker discovery tool for high-dimensional data that provides effect size estimation. LDA scores (>2.0) derived from LEfSe analysis may be used to show differences in relative abundance of bacterial taxa using graphical reports, including LDA bar plots (differential features ranked by effect size) and plot cladograms (representation of relevant features on taxonomic or phylogenetic trees).

2. Assays for Measuring Copy Number

Another assay that can specifically detect copy number of the target biomarker in an amount of DNA includes amplification assays. These include polymerase chain reactions (PCR) assays that are rapid, specific, and sensitive assay process for detection of the target biomarker by amplifying one or more nucleotide sequences. Real-time PCR based on the TaqMan® technology allows DNA or cDNA quantification over a large dynamic range (10 to $10^7$ copies) and is therefore well adapted to the quantification of bacterial genomes. Moreover, the possibility of handling numerous samples and the absence of post-PCR handling makes it a safe and convenient approach.

An oligonucleotide forward primer with a nucleotide sequence complementary to a unique sequence in a region of interest is hybridized to its complementary sequence and extended. Similarly, a reverse oligonucleotide primer complementary to a second sequence in the same or an alternate region is hybridized and extended. This system allows for amplification of specific gene sequences and is suitable for simultaneous or sequential detection systems.

The polymerization assay detects the presence or absence of nucleic acid molecules in a biological sample. The process involves obtaining a biological sample contacting the sample with a compound or an agent capable of detecting a nucleic acid sequence. Preferably, the assay is a quantitative real time polymerase chain reaction (qPCR) using the primers that are constructed based on a partial nucleotide sequence of cDNA corresponding to the target biomarker. A forward primer and a reverse primer are typically used for these purposes. In some aspects, the assay includes primer and probe sequences. The polymerization process typically results in an amplicon.

The primer and probe sequences used in production of an amplicon are specifically tailored and designed to satisfy several different parameters depending on the primer or probe. In general, an amplicon is ideally less than 150 nucleotides, optionally from 75 to 150 nucleotides or any value or range therebetween.

The assay may be used for the simultaneous or sequential detection of the presence or absence and the copy number of the target biomarker.

The assays are performed on an instrument designed to perform such assays, for example those available from Applied Biosystems (Foster City, Calif.). The assays typically include subjecting a nucleic acid from the sample to RT-PCR or PCR reactions using specific primers and detecting the amplified product.

The bacterial RNA sequences are typically converted to complementary DNA (cDNA) sequences and then amplified before being detected. The term "amplified" defines the process of making multiple copies of the nucleic acid in either RNA or DNA form a single or lower copy number of nucleic acid sequence molecule. The amplification of nucleic acid sequences is carried out in vitro by biochemical processes known to those of skill in the art. The amplification agent may be any compound or system that will function to accomplish the synthesis of primer extension products, including enzymes. Suitable enzymes for this purpose include, for example, *E. coli* DNA polymerase I, Taq polymerase, Klenow fragment of *E. coli* DNA polymerase I, T4 DNA polymerase, AmpliTaq Gold DNA Polymerase from Applied Biosystems, other available DNA polymerases, reverse transcriptase (preferably iScript RNase H+ reverse transcriptase), ligase, and other enzymes, including heat-stable enzymes (i.e., those enzymes that perform primer extension after being subjected to temperatures sufficiently elevated to cause denaturation). Suitable enzymes will facilitate combination of the nucleotides in the proper manner to form the primer extension products that are complementary to each mutant nucleotide strand. Generally, the synthesis is initiated at the 3'-end of each primer and proceed in the 5'-direction along the template strand, until synthesis terminates, producing molecules of different lengths. There may be amplification agents, however, that initiate synthesis at the 5'-end and proceed in the other direction, using the same process as described above. In any event, the process of the invention is not to be limited to the embodiments of amplification described herein.

One process of in vitro amplification may include the polymerase chain reaction (PCR) such as those described in U.S. Pat. Nos. 4,683,202 and 4,683,195. The term "polymerase chain reaction" refers to a process for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. Many polymerase chain processes are known to those of skill in the art and may be used in the process of the invention.

Primers used according to the process are complementary to each strand of nucleotide sequence to be amplified. The term "complementary" means that the primers must hybridize with their respective strands under conditions that allow the agent for polymerization to function. In other words, the primers that are complementary to the flanking sequences hybridize with the flanking sequences and permit amplification of the nucleotide sequence. Preferably, the 3' terminus of the primer that is extended is perfectly base paired with the complementary flanking strand. In some embodiments, probes possess nucleotide sequences complementary to one or more of the strands.

Those of ordinary skill in the art will know of various amplification processes that can also be utilized to increase the copy number of a target biomarker. The nucleic acid sequences detected in the process of are optionally further evaluated, detected, cloned, sequenced, and the like, either in solution or after binding to a solid support, by any process usually applied to the detection of a specific nucleic acid sequence such as another polymerase chain reaction, oligomer restriction (Saiki et al., *BioTechnology* 3:1008 1012 (1985)), allele-specific oligonucleotide (ASO) probe analysis (Conner et al., *PNAS* 80: 278 (1983)), oligonucleotide ligation assays (OLAs) (Landegren et al., *Science* 241:1077 (1988)), RNase Protection Assay and the like. Molecular techniques for DNA analysis have been reviewed (Landegren et al., *Science* 242:229 237 (1988)). Following DNA amplification, the reaction product may be detected by the high level of the amplified signal from the probe. In another embodiment, amplification primers are fluorescently labeled and run through an electrophoresis system. Visualization of amplified products may be by laser detection followed by computer assisted graphic display.

In some embodiments, the copy number for *L. lactis* target biomarker may be detected using amplification primers having a nucleic acid sequence as in SEQ ID NOs: 1 and 2; SEQ ID NOs:3 and 4; SEQ ID NOs:5 and 6; SEQ ID NOs:7 and 8; SEQ ID NOs:9 and 10; SEQ ID NOs:11 and 12 and/or SEQ ID NOs:15 and 16.

3. Controls

The methods including analyzing the abundance or the copy number of one or more biomarkers may include comparing to a control. For example, the level of a biomarker detected in a sample obtained from the subject can be compared to the level of the biomarker detected in a sample obtained a control. Suitable controls will be known to one of skill in the art. Controls can include, for example, healthy subjects, such as subjects without the disease or disorder, or non-diseased tissue from the same subject. A control can be a single or pooled or averaged values of like individuals using the same assay. Reference indices for control subjects can be established by analyzing samples from a plurality of control subjects. Reference indices for subjects with the disease can be established and/or by analyzing samples from a plurality of subjects that have been diagnosed with the disease or disorder.

Reference indices for control subjects for the abundance of a microbial biomarker may vary for each biomarker.

For example, reference indices for control subjects for the abundance of *Dorea* sp. 5-2 may be a relative abundance of above about 3%, such as about 4%, about 5%, about 6%, or greater, as measured by LDA.

Reference indices for control subjects for the abundance of *Lactococcus lactis* may be a relative abundance of above about 25%, such as about 30%, about 35%, about 40%, about 45%, about 50%, about 55%, about 60%, or greater, as measured by LDA. Similarly, reference indices for control subjects for copy number of *Lactococcus lactis* may be copy number of above about 20%, such as about 25%, about 30%, about 35%, about 40%, about 45%, about 50%, about 55%, about 60%, or greater, as measured by quantitative PCR.

E. Sensitivity and Specificity of Detecting NAFLD

The sensitivity can be expressed as a percentage, the proportion of actual positives which are correctly identified as such (e.g., the percentage of test subjects having NAFLD correctly identified by the test as having NAFLD). A test with high sensitivity has a low rate of false negatives, i.e., the cases of NAFLD not identified as such. Generally, the disclosed assays and methods have a sensitivity of at least 70%, at least 80%, of at least 90%, at least 92%, at least 94%, at least 95%, at least 96%, at least 97%, at least 98%, at least 99%, or at least 100%.

The specificity can be expressed as a percentage, the proportion of actual negatives which are correctly identified as such (e.g., the percentage of test subjects not having NAFLD correctly identified by the test as not having NAFLD). A test with high specificity has a low rate of false positives, i.e., the cases of individuals not having NAFLD but suggested by the test as having NAFLD. Generally, the disclosed methods have a specificity of at least 60%, at least 70%, at least 80%, at least 90%, at least 92%, at least 94%, at least 95%, at least 96%, at least 97%, at least 98%, at least 99%, or at least 100%.

Positive and negative predictive values are influenced by the prevalence of disease in the population that is being tested. In a high prevalence setting, it is more likely that persons who test positive truly have disease than if the test is performed in a population with low prevalence.

III. Methods of Treating NAFLD

A. NAFLD

Over 70% of patients with type 2 diabetes have concomitant NAFLD, or more specifically, metabolic dysfunction-associated fatty liver disease (MAFLD) using the recently proposed definition (Eslam et al., *J Hepatol.*, 73:202-209 (2020)). NAFLD is the most prevalent chronic liver disease in the U.S. NAFLD exists as two predominant histological subtypes: nonalcoholic fatty liver (NAFL) and nonalcoholic steatohepatitis (NASH) (Kleiner et al., *Hepatology.*; 41(6): 1313-1321 (2005)). NAFL is associated with a relatively benign clinical course, while NASH is associated with increased risk of progressive fibrosis and cirrhosis. NASH may be defined by the presence of hepatic steatosis and inflammation with hepatocyte injury (ballooning) with or without fibrosis (Chalasani et al., *Hepatology;* 55:2005-23 (2012)).

Metabolic syndrome is a prevalent condition among patients with NAFLD. Approximately 90% of patients with NAFLD have more than one component of metabolic syndrome and about one-third of patients meet the criteria of metabolic syndrome. The pathophysiology of NAFLD includes the intrahepatic accumulation of fat in the form of triglycerides, in which insulin resistance is believed to play an important role by facilitating the transport of free fatty acid into the liver from visceral fat stores or peripheral lipolysis. A large body of studies reveals that several metabolic conditions, such as obesity, insulin resistance, diabetes mellitus, dyslipidemia, and hypertension are strongly associated with NAFLD (Bang and Cho, *J Lifestyle Med.;* 5(1): 7-13 (2015)).

Steatosis, also called fatty change, is abnormal retention of fat within a cell or organ. Steatosis most often affects the liver—the primary organ of lipid metabolism—where the condition is commonly referred to as fatty liver disease. NAFLD includes a wide spectrum of liver conditions ranging from simple steatosis to nonalcoholic steatohepatitis (NASH) and advanced hepatic fibrosis.

There are non-invasive tests for detecting liver steatosis and liver fibrosis in NAFLD. These include controlled attenuation parameter (CAP™) and vibration controlled transient elastography (VCTE™), respectively, provided by Fibroscan® (Echosens, Paris, France).

Fibroscan® measurements typically include different probes for measurement accuracy and consistency. The range of probe models typically match the measurement area of most patient morphology. By adjusting the measurement area relative to the distance of the liver below the surface of the skin, a consistent three cubic centimeters explored volume can be maintained. This is achieved through three probes:

S+ Probe, Pediatric: Designed for pediatric patients with a thoracic perimeter less than 75 cm;

M+ Probe, Medium: Designed for adults in which the distance from the skin to the liver capsule is 25 mm or less; and XL+ Probe, Extra Large: Designed for heavier weight adults in which the distance from the skin to the liver capsule is over 35 mm.

Typically, non-invasive liver fibrosis (stiffness) may be measured by VCTE™, and non-invasive liver steatosis may be measures by CAP™. Stiffness (kPa) and CAP (dB/m) measurements can be measured at the same time using FibroScan®. The scan's S, M, and XL probes are compatible with all morphologies of patients. CAP is a tool for non-invasive assessment and quantification of steatosis. CAP is a measure of the ultrasound attenuation which corresponds to the decrease in amplitude of ultrasound waves as they propagate through the liver. CAP is powered by a sophisticated guidance process based on VCTE that ensures that:

CAP and liver stiffness are simultaneously measured in the same liver volume;

CAP is calculated only if liver stiffness measurement is valid CAP is measured with the M probe at 3.5 MHz at depth between 25 mm and 65 mm CAP is expressed in decibel per meter (dB/m);

CAP is calculated only if liver stiffness measurement is valid CAP is measured with the XL probe at 3.5 MHz at depth between 35 mm and 75 mm CAP is expressed in decibel per meter (dB/m).

Hepatic steatosis may be graded by published CAP cut-offs: Mild steatosis 248-267 dB/m, moderate steatosis 268-279 dB/m and severe steatosis ≥280 dB/m (Karlas et al., *J Hepatol;* 66:1022-1030 (2017)).

B. Compositions for Treating NAFLD

Subjects identified as having NAFLD may be treated to reduce one or more symptoms or characteristics of NAFLD. Some of the characteristics of NAFLD are presented in Table 2 and include BMI, CAP, liver stiffness, HbA1c, ALP, ALT, AST, triglycerides, total cholesterol, HDL-c, and LDL-c. For example, the treatment may reduce one or more of plasma levels of total cholesterol, total triglycerides, body mass index (BMI), and other symptoms or characteristics of NAFLD.

The treatment typically includes administering to the subject a composition containing an effective amount of one or more microbial biomarkers *L. lactis* and *Dorea* sp. 5-2. Typically, the composition provides sufficient number of the microbial biomarker to increase the number of these microbes in the subject's gastrointestinal GI tract to the level observed in healthy controls. The increase may be by direct supply of sufficient number of the microbes and/or by supply of sufficient number of the microbes with components aiding in colonization of the GI tract by the microbes. The composition may include between $1.0\times10^{11}$-$1.0\times10^{13}$ colony forming units (CFU) of the microorganisms per ml of the composition or per mg of the composition.

The compositions may be for oral or anal administration and may include capsules, tablets, fortified food, and fecal microbiota transplants. The compositions may include isolated microbial biomarkers *L. lactis* and/or *Dorea* sp. 5-2 alone, or in combination with other commensal bacteria of the microbiome.

1. Pharmaceutical Compositions

Pharmaceutical compositions containing a therapeutically effective amount of a *L. lactis* and/or *Dorea* species are disclosed. The compositions may be formulated with one or more excipients and/or carriers appropriate to the indicated route of administration. In some embodiments, the bacteria are formulated in a manner amenable for the treatment of human and/or veterinary patients. In some embodiments, compositions include admixing or combining one or more of the bacteria with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical compositions may be tableted or encapsulated. In some embodiments, the bacteria may be slurried in water, polyethylene glycol, propylene glycol, ethanol, corn oil, cottonseed oil, peanut oil, sesame oil, benzyl alcohol, sodium chloride, and/or various buffers. In some embodiments, the pharmaceutical compositions may be subjected to pharmaceutical operations, such as sterilization, and/or may contain carriers and/or excipients such as preservatives, stabilizers, wetting agents, emulsifiers, encapsulating agents such as lipids, dendrimers, polymers, proteins such as albumin, nucleic acids, and buffers.

The pharmaceutical compositions may include isolated *L. lactis* and/or isolated *Dorea*. The pharmaceutical compositions may include isolated and purified *L. lactis* and/or isolated and purified *Dorea*. A variety of amounts of these microbes may be included, for example between about $10^3$ CFU and $10^{13}$ CFU, such as between $10^6$ CFU to $10^{13}$ CFU, or between about $10^9$ CFU and $10^{13}$ CFU. In some embodiments, the microbes are included in a pharmaceutical composition or a probiotic composition formulated for oral or enteric administration. For single, or mixed (cultivated) bacteria administration, the bacteria can be administered orally (e.g., in form of tablets). The compositions may be administered by a variety of methods, e.g., orally, intracolonically, intranasally, intrarectally, via a catheter, via a lavage, via a nasogastric tube, via local delivery, or via a method for fecal microbiota transplantation (FMT). Depending on the route of administration, the bacterial compositions may be coated in a material to protect the bacterial compositions from the action of acids and other natural conditions which may inactivate the bacterial compositions. To administer the bacterial composition, it may be necessary to coat the bacterial composition with, or co-administer the bacterial composition with, a material to prevent its inactivation. In some embodiments, the bacterial composition may be administered to a patient in an appropriate carrier, for example, polymers, hydrogels, liposomes, starches, or a diluent. Pharmaceutically acceptable diluents include saline and aqueous buffer solutions. Liposomes include water-in-oil-in-water CGF emulsions as well as conventional liposomes.

Protective formulations may be employed to protect the bacterial compositions from the harsh gastric environment (Govander et al., AAPS PharmSciTech, Vol. 15, No. 1, 29-43 (2014)). Gastro-resistant polymers and coatings have been shown to supply protection against the harsh gastric environment. These coatings included enteric coated tablets and capsules that site-specifically deliver the administered probiotic bacteria to the intestinal system. These enteric coats are often pH selective and allow for protection against the harsh gastric conditions and subsequently dissolve in the alkali media of the intestinal system (Calinescu et al., 2005 and Yang et al., 2002). Non-limiting examples of excipients that may employed in the formulation of bacterial compositions are hydroxypropyl methylcellulose phthalate and carboxymethyl high amylose starch. Excipients may be combined to enhance delivery of the bacterial composition to the gastrointestinal tract. For example, carboxymethyl high amylose starch may be combined with chitosan for delivery of the bacterial composition to the colon. Formulations may include different polymers with different properties, or similar polymers with different properties, depending on the site of intended delivery to deliver the bacterial composition to different areas of the gastrointestinal tract (Yang et al., 2002).

The bacterial compositions may also be administered orally, intracolonically, intranasally, intrarectally, via a catheter, via a lavage, via a nasogastric tube, via local delivery, or via a method for fecal microbiota transplantation (FMT). The bacterial composition may be in the form of a dispersion. Dispersions can be prepared in glycerol, liquid polyethylene glycols, and mixtures thereof and in oils.

In some embodiments, the carrier includes an enteric coating to reduce or slow degradation in the stomach. For example, the enteric coating may be a fatty acid, a wax, a shellac, a plastic such as a phthalate, CAP, CAT, PVAP, HPMCP, or a plant fiber (e.g., Hussan et al., 2012). In some embodiments, the pharmaceutical or probiotic composition may contain chitosan-alginate beads, or a hydrogel.

The bacterial compositions disclosed herein can be administered orally, for example, with an inert diluent or an assimilable edible carrier. The bacterial compositions and other ingredients may also be enclosed in a hard or soft-shell gelatin capsule, compressed into tablets, or incorporated directly into the patient's diet. For oral therapeutic administration, the bacterial compositions disclosed herein may be incorporated with excipients and used in the form of ingestible tablets, buccal tablets, troches, capsules, elixirs, suspensions, syrups, wafers, and the like. The percentage of the therapeutic agent in the compositions and preparations may, of course, be varied. The amount of the therapeutic agent in such pharmaceutical formulations is such that a suitable dosage will be obtained.

In some embodiments, it may be advantageous to formulate compositions in dosage unit form for ease of administration and uniformity of dosage. Dosage unit form as used herein refers to physically discrete units suited as unitary dosages for the patients to be treated; each unit containing a predetermined quantity of therapeutic agent calculated to produce the desired therapeutic effect in association with the required pharmaceutical carrier. In some embodiments, the specification for the dosage unit forms of the invention is dictated by and directly dependent on (a) the unique characteristics of the therapeutic agent and the particular therapeutic effect to be achieved, and (b) the limitations inherent in the art of compounding such a therapeutic agent for the treatment of a selected condition in a patient. In some embodiments, the active agent(s) are administered at a therapeutically effective dosage sufficient to treat a condition associated with a condition in a patient. For example, the efficacy of a bacterial composition can be evaluated in an animal model system that may be predictive of efficacy in treating the disease in a human or another animal.

In some embodiments, the effective dose range for the therapeutic agent can be extrapolated from effective doses determined in animal studies for a variety of different animals Precise amounts of the therapeutic composition depend on the judgment of the practitioner and are specific to each individual. Other factors affecting the dose include the physical and clinical state of the patient, the route of administration, the intended goal of treatment and the potency, stability, and toxicity of the particular therapeutic formulation.

The actual dosage amount of a bacterial composition of the present disclosure administered to a patient may be determined by physical and physiological factors such as type of animal treated, age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

Single or multiple doses of the agents are contemplated. Desired time intervals for delivery of multiple doses can be determined by one of ordinary skill in the art employing no more than routine experimentation. As an example, patients may be administered two doses daily at approximately 12-hour intervals. In some embodiments, the agent is administered once a day.

The composition may be administered on a routine schedule. As used herein, a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the patient has eaten or will eat.

a. Fecal Microbiota Transplant

Microbial dysbiosis leads to the distinct shifts in bacterial products, including ethanol, lipopolysaccharides, short-chain fatty acids, conjugated bile acids, and trimethylamine N-oxide. These metabolites translocate into the portal vein through an impaired intestinal barrier ("leaky" gut), bind to specific toll-like receptors in the liver, and activate the proinflammatory pathways. While there is numerous evidence of an altered gut microbiota being associated with NAFLD, any potential causality has yet to be established.

Fecal microbiota transplantation (FMT) is emerging as a potential therapeutic option for multiple disease entities, such as recurrent *Clostridium difficile* infection, irritable bowel syndrome, inflammatory bowel disease and autoimmune diseases. Recently, a clinical trial showed NAFLD patients who received allogeneic FMT from a healthy donor demonstrating improved intestinal permeability when compared to those who received autologous FMT. Besides, FMT could also be used to construct human microbiota-associated murine models, which have become a well-accepted foundation for addressing causal relationships between altered gut microbiome and host disease and have been applied to understanding the pathophysiology and establishing causality in multiple disease entities. Fecal bacterial biomarkers have been identified via metagenomic sequencing to predict the clinical course of diseases, although such fecal biomarkers have yet to be recognized in NAFLD.

For the fecal microbiota transplantation from donors (FMT), the microbes can be added to the microbiota that is delivered to the gastrointestinal system, e.g., via nasogastric tube or intracolonic administration.

b. Restoring the Abundance of *L. lactis* and *Dorea* in the Gut Microbiome

Typically, the methods of treating include restoring the abundance of *L. lactis* and *Dorea* in the GI tracts of subjects with NAFLD to that observed in the GI tracts of healthy subjects. This may include providing these microbes in isolated form, or in combination with other commensal bacteria forming the microbiome of a healthy gut.

The microbiome includes and ecological community of commensal, symbiotic and pathogenic microorganisms. Commensal microorganisms colonize the host and establish a non-harmful coexistence. The relationship with their host is called symbiotic when microorganisms perform tasks that are known to be useful for the host, and parasitic/pathogenic, when disadvantageous to the host. Commensal microorganisms may be symbiotic microorganisms.

The microbiome can include bacteria, fungi, archaea, and viruses that inhabit the skin and mucosal surfaces of the mouth, nose, digestive tract, and vagina of a host.

Examples of commensal microorganisms include *Bacteroidetes* and *Firmicutes, Actinobacteria, Proteobacteria*, and *Verrucomicrobia*, methanogenic archaea (mainly *Methanobrevibacter smithii*), eukarya (mainly yeasts), and viruses (primarily phage) (Lozupone et al., *Nature,* 489 (7415):220-230 (2012)). See also a list of commensal bacteria provided in Hakansson and Molin, *Nutrients,* 3(6):637-682 (2011).

Examples of pathogenic microorganisms include *Escherichia coli* and *Salmonella* species, *Clostridium difficile, Vibrio cholerae, Shigella* and *Campylobacter*, Rotavirus and Calicivirus (formerly Norwalk virus), and some protozoa (especially *Entamoeba histolytica, Giardia lamblia, Strongyloides stercoralis*) (Gorbach, Chapter 95 "Microbiology of the Gastrointestinal Tract" in Medical Microbiology. 4th edition (1996)).

Disease states may exhibit either the presence of a novel microbe(s), absence of a commensal microbe(s), or an alteration in the proportion of microbes.

Diseases with alterations in the microbiome include Crohn's disease, ulcerative colitis, obesity, asthma, allergies, metabolic syndrome, diabetes, psoriasis, eczema, rosacea, atopic dermatitis, gastrointestinal reflux disease, cancers of the gastrointestinal tract, bacterial vaginosis, neurodevelopmental conditions such as autism spectrum disorders, Alzheimer's disease, Parkinson's disease, and numerous infections, among others. For example, in Crohn's disease, concentrations of *Bacteroides, Eubacteria* and *Peptostreptococcus* are increased whereas *Bifidobacteria* numbers are reduced (Linskens et al., Scand J Gastroenterol Suppl. 2001; (234):29-40); in ulcerative colitis, the number of facultative anaerobes is increased. In obese subjects, the relative proportion of *Bacteroidetes* has been shown to be decreased relative to lean people (Ley et al., Nature. 2006 Dec. 21; 444(7122):1022-3), and possible links of microbial imbalances with the development of diabetes have also been discussed (Cani et al., *Pathol Biol* (Paris). 2008 July; 56(5): 305-9). Segmented Filamentous Bacteria have been shown to play a critical role in prevention of infection and development of autoimmune diseases (Ivanov et al, *Cell.* 139(3): 485-98, 2009). In the skin, a role for the indigenous microbiota in health and disease in both infectious and noninfectious diseases, such as atopic dermatitis, eczema, rosacea, psoriasis, and acne has been noted (Holland et al. 1977 *Br J Dermatol.* 96(6):623-6; Thomsen et al. 1980 *Arch. Dermatol.* 116:1031-1034; Till et al. 2000 *Br. J. Dermatol.* 142:885-892; Paulino et al. 2006 *J. Clin. Microbiol.* 44:2933-2941). Furthermore, the resident microbiota may also become pathogenic in response to an impaired skin barrier (Roth and James 1988 *Annu. Rev. Microbiol.* 42:441-464). Bacterial vaginosis is caused by an imbalance of the naturally occurring vaginal microbiota. While the normal vaginal microbiota is dominated by *Lactobacillus*, in grade 2 (intermediate) bacterial vaginosis, *Gardnerella* and *Mobiluncus* spp. are also present, in addition to Lactobacilli. In grade 3 (bacterial vaginosis), *Gardnerella* and *Mobiluncus* spp. predominate, and Lactobacilli are few or absent (Hay et al., *Br. Med. J.,* 308, 295-298, 1994)

Probiotic bacteria, *Lactobacillus fermentum* and *Bifidobacterium lactis*, appears to inhibit permeability caused by gliadin and therefore to reduce gliadin-induced cellular damage in the gut.

C. Subjects to be Treated

The subjects benefiting from the disclosed methods may be humans, non-human primates, domestic animals, farm animals, or laboratory animals. For example, the subject may be a dog, cat, goat, horse, pig, mouse, rabbit, or the like. The subject may be a human. The subject may be healthy, suffering from, or susceptible to a disease, disorder or condition.

In subjects may have one or more of the diseases metabolic syndrome, type 2 diabetes mellitus, cardiovascular disease (CVD), and chronic kidney disease (CKD). Therefore, the method may detect NAFLD in patients with one or more of diseases metabolic syndrome, type 2 diabetes mellitus, CVD, and CKD.

The subject may be free of disease. The subject may have one or more of diseases metabolic syndrome, type 2 diabetes mellitus, CVD, and CKD. The subject may have metabolic syndrome with one or more of obesity, insulin resistance, diabetes mellitus, dyslipidemia, and hypertension. The subject may have diabetes, liver disease, or a combination of diabetes and liver disease. The subject may have type 2 diabetes. The subject may have NAFLD. The subject may have type 2 diabetes and NAFLD. The subject may or may not have NASH.

IV. Kits for Measuring Microbial Biomarkers

A composition set with one or more microorganisms may be packaged together in any suitable combination as a kit useful for performing, or aiding in the performance of, the disclosed method. It is useful if the kit components in a given kit are designed and adapted for use together in the disclosed method.

For example, disclosed are kits with one or more dosages of *L. lactis* and/or *Dorea*. The kit may include between $1.0 \times 10^{11}$-$1.0 \times 10^{13}$ colony forming units (CFU) of the microorganisms per ml of the composition or per mg of the composition The kits may include dilution buffers, sample buffers, and tools aiding in administration, such as tubes, capsules, and the like. The kits may include instructions use.

The disclosed compositions and methods of making and using the disclosed compositions can be further understood from the following enumerated paragraphs:

1. A method of non-invasively detecting non-alcoholic fatty liver disease (NAFLD) in a subject, the method containing:
   (a) measuring abundance or copy number of a microbial biomarker in a sample from the subject, and
   (b) detecting NAFLD in the subject when
      (i) the abundance of the microbial biomarker in the sample is less than half or about half of the abundance of the microbial biomarker in a healthy control, and/or
      (ii) the number of copies of the microbial biomarker DNA in the sample is about 20 copies/ng bacterial DNA or below 20 copies/ng bacterial DNA.

2. The method of paragraph 1, wherein measuring is by linear discriminant analysis (LDA) to measure abundance.

3. The method of paragraph 1, wherein measuring is by quantitative PCR to measure copy number.

4. The method of paragraphs 1 or 3, wherein measuring is by quantitative PCR using amplification primers containing the nucleic acid sequence of SEQ ID NO:1 and/or SEQ ID NO:2.

5. The method of any one of paragraphs 1-4, wherein microbial biomarker contains *Lactococcus lactis* or *Dorea* sp. 5-2.

6. The method of any one of paragraphs 1-5, wherein detecting NAFLD in the subject is detecting the number of copies of *Lactococcus lactis* DNA in the sample.

7. The method of any one of paragraphs 1-6, wherein detecting NAFLD in the subject is detecting about 20 copies of *Lactococcus lactis* DNA per ng bacterial DNA or below 20 copies of *Lactococcus lactis* DNA per ng bacterial DNA in the sample.

8. The method of any one of paragraphs 1-7, wherein detecting NAFLD in the subject is detecting between undetectable and about 20 copies of *Lactococcus lactis* DNA per ng bacterial DNA in the sample.

9. The method of any one of paragraphs 1-8, wherein detecting NAFLD in the subject is detecting between undetectable and about 15 copies of *Lactococcus lactis* DNA per ng bacterial DNA in the sample.

10. The method of any one of paragraphs 1-9, wherein detecting NAFLD in the subject is detecting between about 5 and about 15 copies of *Lactococcus lactis* DNA per ng bacterial DNA in the sample.

11. The method of any one of paragraphs 1-10, wherein the microbial biomarker contains *Lactococcus lactis* strains or subspecies.

12. The method of any one of paragraphs 1-11, wherein the microbial biomarker contains *Lactococcus lactis* subspecies (subsp.) selected from the group consisting of *L. lactis* subsp. *lactis, L. lactis* subsp. *cremoris, L. lactis* subsp. *hordniae*.

13. The method of any one of paragraphs 1-12, wherein the microbial biomarker contains *Lactococcus lactis* strains selected from the group consisting of CF102, 104, 109, MGYG-HGUT-00226, and *Lactococcus lactis*.

14. The method of any one of paragraphs 1-12, wherein the microbial biomarker contains *L. lactis* subsp. *lactis*.

15. The method of any one of paragraphs 1-14, wherein the microbial biomarker contains *L. lactis* subsp. *lactis* strain CF111 or 112.

16. The method of any one of paragraphs 1-15, wherein the microbial biomarker does not contain *L. lactis* subsp. *cremoris*.

17. The method of any one of paragraphs 1-16, wherein the sample is diluted or undiluted bodily fluid, mucus, or stool.

18. The method of any one of paragraphs 1-17, wherein the sample is a diluted sample diluted at a ratio between about 1:5 and 1:500 (v/v) of the sample to a sample dilution buffer.

19. The method of any one of paragraphs 1-18, wherein the subject has one or more diseases selected from the group consisting of metabolic syndrome, type 2 diabetes mellitus, cardiovascular disease (CVD), and chronic kidney disease (CKD).

20. The method of any one of paragraphs 1-18, wherein the healthy control is a subject free of one or more diseases selected from the group consisting of metabolic syndrome, type 2 diabetes mellitus, cardiovascular disease (CVD), and chronic kidney disease (CKD).

21. A method of treating a subject with non-alcoholic fatty liver disease (NAFLD) or preventing NAFLD in a subject, the method containing administering to the subject a composition containing an effective amount of *Lactococcus lactis* and/or *Dorea* sp. 5-2.

22. The method of paragraph 21, wherein the composition contains a microorganism selected from the group consisting of *L. lactis* subsp. *lactis*, *L. lactis* subsp. *cremoris*, *L. lactis* subsp. *hordniae*.

23. The method of paragraphs 21 or 22, wherein the composition contains *Lactococcus lactis* strains selected from the group consisting of CF102, 104, 109, MGYG-HGUT-00226, and *Lactococcus lactis*.

24. The method of any one of paragraphs 21-23, wherein the composition contains *L. lactis* subsp. *lactis*.

25. The method of any one of paragraphs 21-23, wherein the composition contains *L. lactis* subsp. *lactis* strain CF111 or 112.

26. The method of any one of paragraphs 21-25, wherein the composition does not contain *L. lactis* subsp. *cremoris*.

27. The method of any one of paragraphs 21-26, wherein the composition contains isolated *Lactococcus lactis* and/or isolated *Dorea* sp. 5-2.

28. The method of any one of paragraphs 21-27, wherein the composition contains *Dorea* sp. 5-2 at a relative abundance of about 3%, or greater than about 3%, such as between about 3% and 6%, as measured by linear discriminant analysis (LDA).

29. The method of any one of paragraphs 21-28, wherein the composition contains *Lactococcus lactis* at a relative abundance of about 30% or greater than about 30%, such as between about 30% and 60%, as measured by LDA.

30. The method of any one of paragraphs 21-29, wherein the composition contains *Lactococcus lactis* at a relative abundance of about 30 copies of *Lactococcus lactis* DNA per ng bacterial DNA, or greater than about 30 copies of *Lactococcus lactis* DNA per ng bacterial DNA, as determined by quantitative polymerase chain reaction (qPCR).

31. The method of any one of paragraphs 21-30, wherein the composition contains between $1.0 \times 10^{11}$-$1.0 \times 10^{13}$ colony forming units (CFU) of the microorganisms per ml of the composition or per mg of the composition.

32. The method of any one of paragraphs 21-31, wherein the composition is a fecal microbial transplant.

33. The method of paragraph 1, wherein measuring comprises a linear discriminant analysis (LDA) to measure abundance.

34. The method of paragraph 1 or 33, wherein measuring comprises a catalase activity test to measure the presence or absence of the catalase enzyme.

35. The method of any one of paragraphs 1, 33, or 34, wherein measuring comprises a quantitative PCR to measure copy number.

36. The method of any one of paragraphs 1 or 33-35, wherein measuring is by quantitative PCR using amplification primers comprising the nucleic acid sequence of (1) SEQ ID NO:1 and/or SEQ ID NO:2, (2) SEQ ID NO:3 and/or SEQ ID NO:4, (3) SEQ ID NO:5 and/or SEQ ID NO:6, (4) SEQ ID NO:7 and/or SEQ ID NO:8, (5) SEQ ID NO:9 and/or SEQ ID NO:10, (6) SEQ ID NO:11 and/or SEQ ID NO:12, (7) SEQ ID NO:13 and/or SEQ ID NO:14, and/or (8) SEQ ID NO:15 and/or SEQ ID NO:16.

37. The method of any one of paragraphs 1 or 33-36, wherein measuring is by quantitative PCR using amplification primers comprising the nucleic acid sequence of (1) SEQ ID NO:1 and/or SEQ ID NO:2.

38. The method of any one of paragraphs 1 or 33-37, wherein measuring is by quantitative PCR using amplification primers comprising the nucleic acid sequence of (2) SEQ ID NO:3 and/or SEQ ID NO:4.

39. The method of any one of paragraphs 1 or 33-38, wherein measuring is by quantitative PCR using amplification primers comprising the nucleic acid sequence of (3) SEQ ID NO:5 and/or SEQ ID NO:6.

40. The method of any one of paragraphs 1 or 33-39, wherein measuring is by quantitative PCR using amplification primers comprising the nucleic acid sequence of (4) SEQ ID NO:7 and/or SEQ ID NO:8.

41. The method of any one of paragraphs 1 or 33-40, wherein measuring is by quantitative PCR using amplification primers comprising the nucleic acid sequence of (5) SEQ ID NO:9 and/or SEQ ID NO:10.

42. The method of any one of paragraphs 1 or 33-41, wherein measuring is by quantitative PCR using amplification primers comprising the nucleic acid sequence of (6) SEQ ID NO:11 and/or SEQ ID NO:12.

43. The method of any one of paragraphs 1 or 33-42, wherein measuring is by quantitative PCR using amplification primers comprising the nucleic acid sequence of (7) SEQ ID NO:13 and/or SEQ ID NO:14.

44. The method of any one of paragraphs 1 or 33-43, wherein measuring is by quantitative PCR using amplification primers comprising the nucleic acid sequence of (8) SEQ ID NO:15 and/or SEQ ID NO:16.

45. The method of any one of paragraphs 36-44, wherein when primers of more than one of (1), (2), (3), (4), (5), (6), (7), and (8) are used for quantitative PCR, a separate quantitative PCR reaction is performed for the primers used from different of (1), (2), (3), (4), (5), (6), (7), and (8).

46. The method of paragraph 45, wherein when a separate quantitative PCR reaction is performed for the primers used from different of (1), (2), (3), (4), (5), (6), (7), and (8), the separate quantitative PCR reactions are performed in parallel.

47. The method of paragraph 45, wherein when a separate quantitative PCR reaction is performed for the primers used from different of (1), (2), (3), (4), (5), (6), (7), and (8), the separate quantitative PCR reactions are performed sequentially.

48. The method of paragraph 45, wherein separate quantitative PCR reactions are performed sequentially for primers of (1), primers of (2), (3), and/or (4), primers of (5), (6), and/or (7), and primers of (8), the separate quantitative PCR reactions are performed sequentially.

49. The method of any one of paragraphs 33-48, wherein microbial biomarker comprises *Lactococcus lactis* or *Dorea* sp. 5-2.

50. The method of any one of paragraphs 33-49, wherein detecting NAFLD in the subject is detecting the number of copies of *Lactococcus lactis* DNA in the sample.

51. The method of any one of paragraphs 33-50, wherein detecting NAFLD in the subject is detecting about 20 copies of *Lactococcus lactis* DNA per ng bacterial DNA or below 20 copies of *Lactococcus lactis* DNA per ng bacterial DNA in the sample.

52. The method of any one of paragraphs 33-51, wherein detecting NAFLD in the subject is detecting between undetectable and about 20 copies of *Lactococcus lactis* DNA per ng bacterial DNA in the sample.

53. The method of any one of paragraphs 33-52, wherein detecting NAFLD in the subject is detecting between undetectable and about 15 copies of *Lactococcus lactis* DNA per ng bacterial DNA in the sample.

54. The method of any one of paragraphs 33-53, wherein detecting NAFLD in the subject is detecting between about 5 and about 15 copies of *Lactococcus lactis* DNA per ng bacterial DNA in the sample.

55. The method of any one of paragraphs 33-54, wherein the microbial biomarker comprises *Lactococcus lactis* strains or subspecies.

56. The method of any one of paragraphs 33-55, wherein the microbial biomarker comprises *Lactococcus lactis* subspecies (subsp.) selected from the group consisting of *L. lactis* subsp. *lactis*, *L. lactis* subsp. *cremoris*, *L. lactis* subsp. *hordniae*.

57. The method of any one of paragraphs 33-56, wherein the microbial biomarker comprises *Lactococcus lactis* strains selected from the group consisting of CF102, 104, 109, MGYG-HGUT-00226, and *Lactococcus lactis*.

58. The method of any one of paragraphs 33-57, wherein the microbial biomarker comprises *L. lactis* subsp. *lactis*.

59. The method of any one of paragraphs 33-58, wherein the microbial biomarker comprises *L. lactis* subsp. *lactis* strain CF111 or 112.

60. The method of any one of paragraphs 33-59, wherein the microbial biomarker does not comprise *L. lactis* subsp. *cremoris*.

61. The method of any one of paragraphs 33-60, wherein the sample is diluted or undiluted bodily fluid, mucus, or stool.

62. The method of any one of paragraphs 33-61, wherein the sample is a diluted sample diluted at a ratio between about 1:5 and 1:500 (v/v) of the sample to a sample dilution buffer.

63. The method of any one of paragraphs 33-62, wherein the subject has one or more diseases selected from the group consisting of metabolic syndrome, type 2 diabetes mellitus, cardiovascular disease (CVD), and chronic kidney disease (CKD).

64. The method of any one of paragraphs 33-62, wherein the healthy control is a subject free of one or more diseases selected from the group consisting of metabolic syndrome, type 2 diabetes mellitus, cardiovascular disease (CVD), and chronic kidney disease (CKD).

EXAMPLES

Example 1. Stool Microbes from Healthy Human Donors Prevent NAFLD Development in Mice Materials and Methods Abbreviations ALP, alkaline phosphatase; ALT, alanine aminotransferase; AST, aspartate aminotransferase; AUC, area under the curve; dB/m, decibel per meter; BMI, body-mass index; CAP, controlled attenuation parameter; FABP4, fatty acid-binding protein 4; FMT, fecal microbiota transplantation; HbA1c, glycosylated hemoglobin A1c; HC, healthy controls; HDL-c, high-density lipoprotein cholesterol; HMA, human microbiota-associated; IPGTT, intraperitoneal glucose tolerance test; IQR, interquartile range; kPa, kilopascals; LDA, linear discriminant analysis; LDL-c, low-density lipoprotein cholesterol; LEfSe, linear discriminant analysis effect size; LN, lean non-alcoholic fatty liver disease; NAFLD, non-alcoholic fatty liver disease; ON, obese non-alcoholic fatty liver disease; PCR, polymerase chain reaction; PCoA, principal coordinate analysis; ROS, reactive oxygen species; SEM, standard error of the mean; VCTE, vibration-controlled transient elastography; ZO-1, zonula occludens-1.

Human Microbiota-Associated Murine Model

All animal experimental procedures were approved by the Committee on the Use of Live Animals in Teaching and Research at the University of Hong Kong. Collected fecal samples from human donors were utilized without pooling to prepare the fecal slurry for oral administration to mice. One gram of the stool was vortexed, centrifuged, and then suspended in 5 mL sterilized phosphate-buffered saline (PBS). The prepared fecal slurries were stored at −80° C. until preforming FMT. 28 seven-week-old male C57BL/6J mice (Centre for Comparative Medicine Research, The University of Hong Kong) were pre-treated with antibiotics mixture including ampicillin (1 g/L), vancomycin (500 mg/L), neomycin sulfate (1 g/L), and metronidazole (1 g/L) in drinking water for one week as reported previously (Wong et al., *Gastroenterology*; 153:1621-1633 (2017); Liu et al., *Cell Metab*; 31:77-91 (2020); and Hoyles et al., *Nat Med*; 24:1070-1080 (2018)). Antibiotic-containing water was changed three times a week. After a 3-day washout period, all mice were randomly divided into four groups: FMT with microbiota from healthy controls (FMT-Healthy, n=8), lean NAFLD patients (FMT-Lean, n=8), obese NAFLD patients (FMT-Obese, n=8), and oral gavage sterile PBS as control (non-FMT, n=4). An aliquot of 200 µl fecal suspension from each donor was transferred into their mouse counterpart once daily in the first week of colonization and three times a week in the following weeks to reinforce colonization for the next 11 weeks.

All of the mice were switched from a standard chow diet (5053, contained 13.134% fat from ether extract, 62.349% carbohydrates, and 24.517% protein, LabDiet, St. Louis, MO) to a high-fat diet (HFD, D12492, contained 60% fat from lard, 20% carbohydrates, and 20% protein, Research Diets, New Brunswick, NJ) for 12 weeks after the initial FMT, and were maintained under controlled environmental conditions (23±1° C., 50-60% humidity, 12-hour light/dark cycles) with food and water ad libitum (FIG. 1A). Body weight was monitored weekly. Body composition was assessed by the Minispec LF90 body composition analyzer (Bruker, Billerica, MA) according to manufacturer's instructions.

Human Donor Recruitment

Twenty four Asian human FMT donors were recruited and categorized as three groups (n=8 each): obese NAFLD patients with body-mass index (BMI)≥30 kg/m$^2$; lean NAFLD with BMI <25 kg/m$^2$; and non-obese, non-steatotic healthy controls. NAFLD was diagnosed using CAP measurements via VCTE (Fibroscan, Echosens, Paris) in donors without a drinking history, with steatosis defined as CAP ≥248 dB/m (Karlas et al., *Journal of hepatology;* 66:1022-1030 (2017)). VCTE was performed by an experienced operator who had performed more than 1,000 measurements. Both CAP and liver stiffness, a quantitative marker of liver fibrosis, were reported by the median of at least 10 successful measurements, expressed in decibel per meter (dB/m) and kilopascals (kPa) respectively, and considered valid with an interquartile range of <40 dB/m and <30% respectively (Fan et al., *Journal of hepatology;* 67:862-873 (2017)). Dietary intake was collected based on a validated food frequency questionnaire (Woo et al., *Nutr Res;* 17:1633-1641 (1997)). Participants provided their average frequency of consumption over the past year in the format of serving size, which was then converted to servings/week as reported (Nguyen et al., *Gastroenterology;* 158:1313-1325 (2020)). All recruited participants signed a written informed consent. The exclusion criteria consisted of: (1) concomitant liver diseases including co-infection with hepatitis B, hepatitis C or human immunodeficiency virus, co-existing Wilson's disease, primary biliary cholangitis, autoimmune hepatitis; (2) significant alcohol intake (≥30 g/d for men or ≥20 g/d for women); (3) history of liver transplantation, currently active or suspected hepatocellular carcinoma; (4) currently on medications known to induce hepatic steatosis (including corticosteroids, methotrexate, and tamoxifen); (5) antibiotic usage in last 12 months, herbal medicine, probiotic, laxative usage and hormonal therapy in last 12 months; (6) pregnancy at the time of recruitment. The study was approved by the Institutional Review Board, The University of Hong Kong and Hong Kong West Cluster of the Hospital Authority, Hong Kong.

Biochemical Measurements

Mice were sacrificed after 12 weeks of FMT and HFD feeding. Blood was collected by cardiac puncture and centrifuged with 3,000 rpm for 15 minutes. All plasma samples were frozen at −80° C. for further analysis. The circulating levels of triglyceride (TG), total cholesterol (TC), alanine aminotransferase (ALT), and aspartate aminotransferase (AST) were measured using commercial kits (Stanbio Laboratory). The circulating adiponectin (Antibody and Immunoassay Services) and fatty acid-binding protein 4 (ABclonal Inc.) levels were detected by way of enzyme-linked immunosorbent assay (ELISA) according to the manufacturer's instructions.

Histological Staining

Mouse liver, white adipose tissue and ileum tissues were directly embedded with optimal cutting temperature compound to make frozen sections. Another part of liver tissue was fixed in 10% neutral-buffered formalin for 24 hours and processed for paraffin embedding. The paraffin sections were prepared in 5 μm, subsequently deparaffinized and rehydrated in xylene and graded ethanol. The sections were processed for hematoxylin and eosin (H&E) to evaluate the morphology.

Determination of Intrahepatic Lipid Accumulation

The liver frozen sections were stained using Oil red O to evaluate intrahepatic lipids. 30-40 mg liver tissue was homogenized with 400 μl chloroform-methanol mixture (2:1, v/v), and the volume was adjusted by adding 80 μl methanol. The homogenate was centrifuged at the speed of 10,000 rpm at 4° C. for 5 minutes, and the supernatant was transferred into a new micro-centrifuge tube and mixed with 160 μl chloroform. The extract was mixed thoroughly with 128 μl distilled water and centrifuged at the speed of 10,000 rpm at 4° C. for 5 minutes. The upper phase was removed, and the lower phase was dried with nitrogen gas. The dried lipids were emulsified by sonication in modified 0.1% SDS-PBS buffer (5 mM $MgCl_2$, 0.1% SDS in PBS) at the amplification of 26%, 30 s, 3 times. The lipids were measured with the corresponding TG and TC kits according to the manufactory's instructions.

Intraperitoneal Glucose Tolerance Test

After 12 weeks of FMT and HFD feeding, intraperitoneal glucose tolerance test was used to evaluate the glucose intolerance. All mice were injected with D-glucose (2 g/kg body weight) intraperitoneally after fasted for 16 hours. Blood glucose levels on whole blood from tail vein were monitored at various time points (0, 15, 30, 60, and 120 minutes) with an ACCU-CHEK Glucose Meter (Roche Diabetes Care, Inc).

Determination of Hepatic Macrophage Infiltration and Reactive Oxygen Species (ROS) Production Hepatic macrophage infiltration was determined by immunostaining with anti-F4/80 antibody in the liver frozen sections and western blot analysis. Dihydroethidium (MedChemExpress, USA) was used to measure hepatic ROS production directly. The fluorescence units and densities were quantified using ImageJ software.

Examination of Intestinal Barrier Function

The ileal expression of lysozyme and zonula occludens (ZO-1) were determined by immunochemistry staining and western blot. Details of antibodies used in the immunoassays are listed in Table 1.

Western Blot

Proteins were extracted from the mouse livers and ileums using radioimmunoprecipitation assay buffer (Sigma Aldrich Inc.) with phenylmethylsulfonyl fluoride protease inhibitor in a ratio of 1:100. A total of 50 μg protein was subjected to electrophoresis and then transferred onto polyvinylidene fluoride membranes (Bio-Rad Laboratories), blocked in 5% blocking buffer (skim milk) for 1 h at room temperature, and incubated with anti-lysozyme rabbit antibody (Abbexa Ltd), anti-F4/80 rabbit antibody (Thermo Fisher), anti-zonula occludens-1 (anti-ZO-1) rabbit antibody (ABclonal Inc.), anti-β-actin rabbit antibody (Thermo Fisher) overnight at 4° C. The membranes were incubated with horseradish peroxidase-conjugated anti-mouse or anti-rabbit IgG (Cell Signaling Technology). The protein bands were visualized with enhanced chemiluminescence detection kit (Bio-Rad Laboratories) and imaged with Chemi-Doc™ MP Imaging System (Bio-Rad Laboratories). The densities were analyzed by ImageJ software (National Institutes of Health).

TABLE 1

Antibodies used for immunoassays.

| Application | Specificity | Catalog# | Vendor | Dilution |
| --- | --- | --- | --- | --- |
| Immunohistochemistry/ Western Blot | Lysozyme | Abx125359 | Abbexa, UK | 1:200/ 1:5000 |
| Immunofluorescence/ Western Blot | F4/80 | A1256 | ABclonal | 1:100/ 1:1000 |
| Western Blot | zonula ocludens-1 (ZO-1) | 617300 | Thermo Fisher Scientific, USA | 1:1000 |
| Western Blot | β-actin | MA1140 | Thermo Fisher Scientific, USA | 1:5000 |
| Immunofluorescence | Alexa Fluor 594 goat anti-mouse IgG (H + L) | A11005 | Thermo Fisher Scientific, USA | 1:200 |
| Immunohistochemistry/ Western Blot | Anti-rabbit IgG, HRP-linked Antibody | CST-7074S | Cell Signaling Technology, USA | 1:5000 |
| Western Blot | Anti-mouse IgG, HRP-linked Antibody | CST-7076S | Cell Signaling Technology, USA | 1:5000 |

Quantitative Detection of Identified Microbial Biomarker in Human Fecal Samples by Targeted Quantitative Polymerase Chain Reaction The standard strain *Lactococcus lactis* as a control was cultured in brain heart infusion broth and then inoculated to a brain heart infusion agar plate at room temperature for 24-28 hours. The number of colony-forming units was standardized by measuring optical density (600 nm). Diluted genomic DNA ($1.0 \times 10^{11}$-$1.0 \times 10^{13}$ CFU/mL) was used as standard. The logarithm of the identified microbial biomarker concentration (x) was the horizontal coordinate, and the threshold cycle (Ct) values (y) was the ordinate to generate a standard curve: y=−3.3036x+33.563 with a good linear relationship with $R^2$=0.996.

QPCR was performed to quantify the abundance of the identified microbial biomarker in human fecal samples using DNA Engine Opticon® 2 System for Real-Time PCR Detection (Bio-Rad Laboratories) with SYBR Green I (Takara Bio) and specific primers. The used primers for *Lactococcus lactis* in this study were: forward 5'-TGTCACAAGC-CATGCGAAAC-3' (SEQ ID NO:1), reverse 5'-CACGCAATTGGTTGATGAAAA-3' (SEQ ID NO:2). The results are presented as copies of per ng fecal DNA.

Metagenomics Analysis and Fecal Biomarker Discovery

Stool DNA was extracted using QIAamp PowerFecal DNA kit (Qiagen) and subjected to library preparation. Library preparation and Illumina sequencing (Paired-End sequencing of 150 bp on NovaSeq 6000) were performed at the Centre for PanorOmic Sciences, The University of Hong Kong. All libraries were prepared based on the protocols of KAPA Hyper Prep Kit (KR0961-V1.14). The adapter ligated library with a size range of 300-750 bp was selected by dual-Solid Phase Reversible Immobilization method, followed by library enrichment via polymerase chain reaction (PCR). The enriched libraries were validated by Fragment Analyzer (Agilent), Qubit and qPCR for quality control analysis. The libraries were denatured and diluted to optimal concentration for sequencing.

Using software from Illumina (bcl2fastq), sequencing reads were assigned to individual samples with each sample having an average throughput of 10.4 Gb and a total throughput of 501.3 Gb for the forty-eight samples. In terms of sequence quality, an average of 95% of the bases achieved a quality score of Q30 where Q30 denotes the accuracy of a base call to be 99.9%.

Raw data was pre-processed through quality control using SOAPnuke 2 (Chen et al., *Gigascience;* 7:1-6 (2018)) and host-derived reads were removed using kneaddate website. The sequencing throughput for each sample was rarefied to 35 million reads. Clean reads were assembled using IDBA-UD 1.1.3 (Peng et al., *Bioinformatics;* 28:1420-1428 (2012)) with default parameters. 16S genes were predicted by barrnap 0.9. All statistical analyses of the gut microbiome were performed with R v3.4.4 software, unless otherwise stated. Taxonomy profiling at different taxonomic levels was performed with metaphlan v3 (Segata et al., *Nat Methods;* 9:811-814 (2012)). Analysis of α- and β-diversity in bacterial communities was performed using vegan: Community Ecology Package version 2.5-6 Shannon index and Chao1 index were calculated for α-diversity and richness analysis. Statistical method was Mann-Whitney test and p-value was adjusted by Benjamini-Hochberg was applied. Ordination was done by principal coordinate analysis (PCoA) with Bray-Curtis distance. Multivariate analysis was performed using permutational multivariate analysis of variance.

Microbiota-based biomarker analysis was performed with linear discriminant analysis (LDA) effect size (LEfSe) (Segata et al., *Genome Biol;* 12:R60 (2011)), a biomarker discovery tool for high-dimensional data that provides effect size estimation. LDA scores (>2.0) derived from LEfSe analysis were used to show differences in relative abundance of bacterial taxa using graphical reports, including LDA bar plots (differential features ranked by effect size) and plot cladograms (representation of relevant features on taxonomic or phylogenetic trees). Spearman's rank correlation coefficient was adopted to understand the correlation.

The co-occurrence network was visualized with Cytoscape software (Shannon et al., *Genome Res;* 13:2498-2504 (2003)) if the |Spearman's rank correlation coefficient|>0.3 and p-value<0.05. For pathway enrichment, humann3 (Franzosa et al., *Nat Methods;* 15:962-968 (2018)) was employed for functional annotation to Metacyc database (SRI International, Menlo Park, CA). Pathway abundances were estimated by summing up the abundance of all genes present in the corresponding pathways, with enrichments as quantified and defined by the Enzyme Commission (EC) number compared using Mann-Whitney U test. EC 2.3.1.47, EC 2.6.1.62, EC 6.3.3.3 and EC 2.8.16 were assigned to 8-amino-7-oxononanoate synthase, 8-amino-7-oxononanoate transaminase, dethiobiotin synthetase, and biotin synthase. Differentially altered Metacyc pathway were performed by LEfSe analysis and displayed using LDA bar plots. Boxes represent the IQRs between the first and third quartiles, and the line inside the box represents the median; whiskers represent the lowest or highest values within 1.5 times IQR from the first or third quartiles. Dots represent data point beyond the whiskers.

Statistical Analysis

All data were analyzed using GraphPad Prism 6.0 (GraphPad Software, San Diego, CA) or SPSS (version 19.0, SPSS Inc, Chicago, IL) and presented as the mean±SEM or median (IQR) as appropriated. To examine the significant differences between groups, the data were compared using unpaired two-tailed Student's t test, Mann-Whitney U test, Kruskal-Wallis test or one-way ANOVA test with or without Tukey's multiple comparisons as appropriate for continuous variables. p-value<0.05 was considered statistically significant throughout.

Results

Subject Characteristics

The baseline clinical characteristics of all 24 human fecal donors are depicted in Table 2. Significant differences were observed in median CAP, ALP, ALT, glycosylated hemoglobin (HbA1c) and fasting blood glucose (all p<0.05), and a borderline significant difference in median liver stiffness (p=0.0661) of healthy, lean NAFLD and obese NAFLD donors (Table 2 and Table 3). When comparing lean NAFLD versus obese NAFLD donors, there were no significant differences in dietary intake, liver biochemistry, lipid profiles, fasting glucose and HbA1c levels (all p>0.05, Table 2 and Table 3).

TABLE 2

Baseline characteristics of all subjects.

| | Healthy (n = 8) Median (IQR) | Lean NAFLD (n = 8) Median (IQR) | Obese NAFLD (n = 8) Median (IQR) | p-value |
|---|---|---|---|---|
| Age, y | 30.67 (28-34.67) | 63.5 (57.5-69.5) ** | 57 (52.25-61.25) ** | 0.0003 |
| Male patients, n (%) | 5 (62.5%) | 5 (62.5%) | 5 (62.5%) | — |
| BMI, kg/m$^2$ | 21.45 (18.8-22.6) | 23.85 (22.78-24.6) | 33.45 (31.93-35.9) ** | <0.0001 |
| CAP, dB/m | 182.5 (177.5-200.5) | 305 (276.25-317.75) | 356.5 (334-383) ** | <0.0001 |
| Liver stiffness, kPa | 4.73 (4.33-5.2) | 4.65 (4.2-6) | 8.35 (4.9-11.33) | 0.0661 |
| Diabetes, n (%) | 0 (0%) | 8 (100%) | 8 (100%) | — |
| Usage of antidiabetic drugs, n (%) | 0 (0%) | 8 (100%) | 8 (100%) | — |
| Usage of antilipemic drugs, n (%) | 0 (0%) | 6 (75%) | 7 (87.5) | — |
| HbA1c, % | 5.4 (5.35-5.6) | 7.2 (6.6-7.25) | 7.8 (7.5-8.8) ** | 0.0060 |
| ALP, U/L | 48 (41.5-54) | 61 (50.5-71) | 84.5 (61.75-95) ** | 0.0163 |
| ALT, U/L | 12 (10-18) | 21 (18-23.5) | 24.5 (18.5-30.25) ** | 0.0401 |
| AST, U/L | 17 (25-20) | 19 (17.5-23.5) | 23 (16-25.75) | 0.2886 |
| Fasting blood glucose, mM | 5.1 (4.49-5.15) | 8.35 (7.4-9.6) ** | 7.6 (6.5-8.9) | 0.0040 |
| Triglycerides, mM | 1.07 (0.92-1.46) | 1.35 (0.93-1.48) | 1.5 (1.28-1.78) | 0.4219 |
| Total Cholesterol, mM | 4.44 (3.59-6.01) | 3.65 (3.425-4.1) | 4.5 (3.73-4.88) | 0.2187 |
| HDL-c, mM | 1.4 (1.28-1.53) | 1.25 (0.975-1.3) | 1.1 (1-1.25) | 0.0845 |
| LDL-c, mM | 3 (2.81-3.91) | 1.9 (1.63-2.25) ** | 2.8 (2.15-3) | 0.070 |

Data are expressed as median (IQR). Kruskal-Wallis test was adopted to calculate significance among three groups and multiple comparisons were followed by Dunn's test.
* p < 0.05, ** p < 0.01 indicate healthy vs. lean NAFLD.
* p < 0.05, ** p < 0.01 denote comparisons between healthy and obese NAFLD.
* p < 0.05, ** p < 0.01 indicate comparisons between lean NAFLD and obese NAFLD.
ALP, alkaline phosphatase; ALT, alanine transaminase; AST, aspartate transaminase; BMI, body mass index; CAP, controlled attenuation parameter; HbA1c, glycosylated hemoglobin A1c; HDL-c, high-density lipoprotein cholesterol; LDL-c, low-density lipoprotein cholesterol; IQR, interquartile range; NAFLD, non-alcoholic fatty liver disease.

TABLE 3

Dietary intake of all subjects.

| Dietary intake (servings/week) | Healthy (n = 8) Median (IQR) | Lean NAFLD (n = 8) Median (IQR) | Obese NAFLD (n = 8) Median (IQR) | p-value |
|---|---|---|---|---|
| Five cereals | 17.50 (14.00-23.63) | 14.00 (10.50-24.50) | 14.00 (14.00-24.50) | 0.1665 |
| Vegetables | 10.50 (7.00-19.25) | 10.50 (7.00-14.00) | 10.00 (8.00-17.50) | 0.9077 |
| Fruits | 7.00 (5.25-13.13) | 5.625 (2.25-7.00) | 7.50 (7.00-14.00)* | 0.0235 |
| Meats | 7.00 (7.00-12.25) | 8.00 (3.438-18.38) | 8.75 (5.25-14.00) | 0.9795 |
| Eggs | 3.50 (3.00-5.75) | 4.75 (3.25-6.50) | 3.00 (2.00-6.00) | 0.6030 |
| Fish | 3.50 (2.25-5.50) | 3.25 (2.25-4.875) | 4.00 (3.00-7.00) | 0.6759 |
| Other seafoods | 2.00 (0.00-5.25) | 0.75 (0.00-1.15) | 1.00 (0.00-1.00) | 0.3349 |

TABLE 3-continued

Dietary intake of all subjects.

| Dietary intake (servings/week) | Healthy (n = 8) Median (IQR) | Lean NAFLD (n = 8) Median (IQR) | Obese NAFLD (n = 8) Median (IQR) | p-value |
|---|---|---|---|---|
| Legumes | 2.30 (2.00-3.375) | 1.00 (0.00-2.50) | 0.50 (0.00-3.00) | 0.0545 |
| Dairy products | 7.00 (5.00-7.00) | 0.25 (0.00-5.00) | 1.00 (0.00-1.00) | 0.0289 |

Data are expressed as median (IQR: interquartile range). Kruskal-Wallis test was adopted to calculate significance among three groups and multiple comparisons were followed by Dunn's test.
*p < 0.05, **p < 0.01 indicate healthy vs. lean NAFLD.
*p < 0.05, **p < 0.01 denote comparisons between healthy and obese NAFLD.
*p < 0.05, **p < 0.01 indicate comparisons between lean NAFLD and obese NAFLD.

Figure 1B:
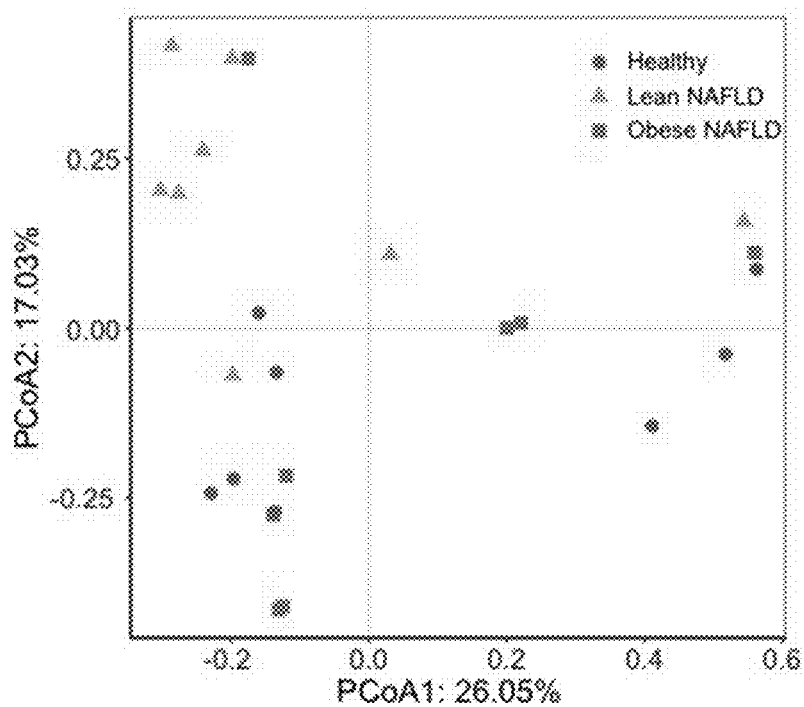
FIG. 1B is a graph showing Principal coordinates analysis (PCoA) of microbiota based on Bray-Curtis distance (a quantitative measure of community dissimilarity); Significance of different groups was calculated by permutational multivariate analysis of variance (PERMANOVA) test with 9999 permutations.
Figure 2A:
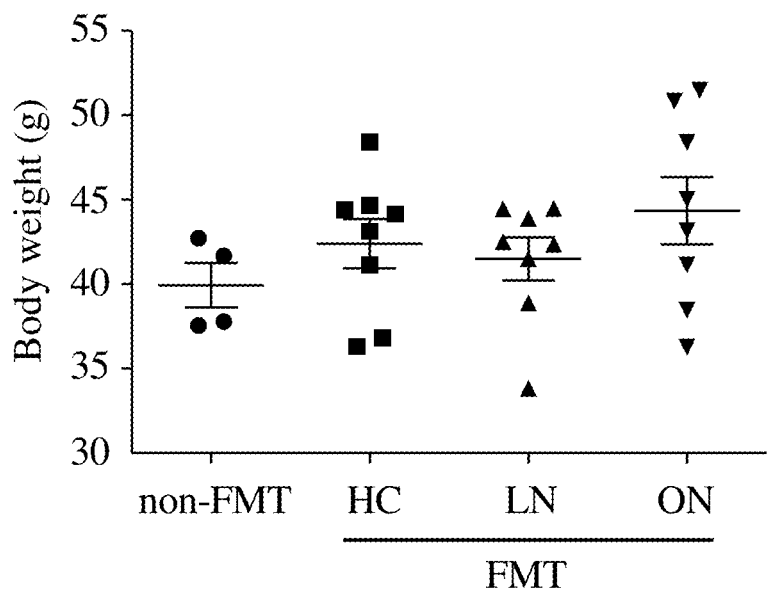
FIGS. 2A-2C are graphs showing Body weight (g) (FIG. 2A); Plasma triglycerides levels (mg/dL) (FIG. 2B); Plasma total cholesterol levels (mg/dL) (FIG. 2C) in mice colonized with microbiota from healthy, lean NAFLD and obese NAFLD donors (n=8 in each group) and vehicle as non-FMT group.

Shotgun metagenomic sequencing was performed on human fecal samples, with the fecal microbial profiles. No significant differences in Shannon index (alpha diversity) or Chao 1 (richness) was observed between all three groups (p>0.05), possibly due to high individual variation within groups. There was a discrimination at the genus level observed within human donor groups (p<0.05, FIG. 1B, FIG. 2A and Table 4).

TABLE 4

Permutational multivariate analysis of variance (PERMANOVA) analysis among different groups.

| Groups | Variation (R2) | Pr (>F) | Significance |
|---|---|---|---|
| Healthy donors vs. Lean NAFLD donors | 0.139562 | 0.0341 | * |
| Lean NAFLD donors vs. Obese NAFLD donors | 0.123261 | 0.0479 | * |
| FMT-Healthy vs. FMT-Obese NAFLD | 0.15401 | 0.0227 | * |
| FMT-Lean vs. FMT-Obese NAFLD | 0.155767 | 0.0274 | * |

The Effects of Stool Microbes from Human Donors on the Intrahepatic Lipid Accumulation The potential causal relationship between gut microbiota and NAFLD was examined via the human-microbiota associated mouse model. No significant differences were found in body weight between FMT-Healthy and FMT-Obese (p>0.05, FIG. 2A).

Figure 2B:
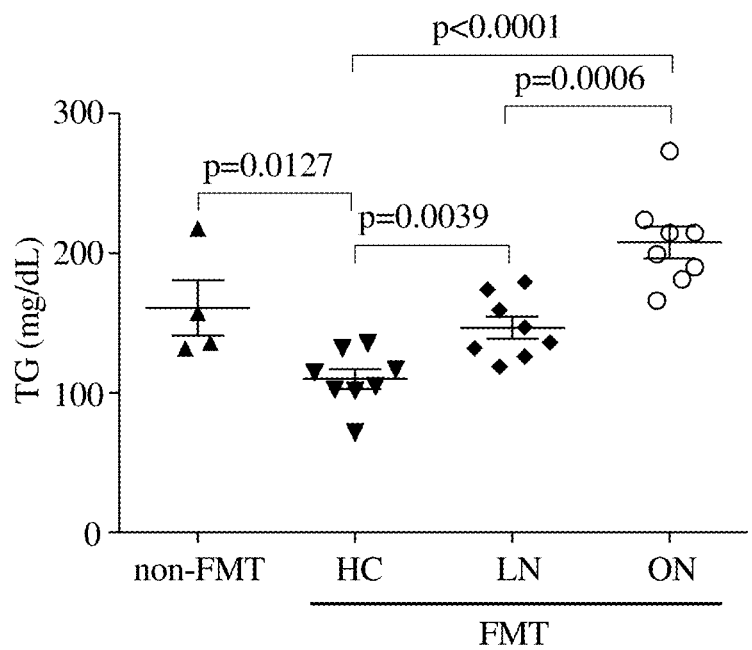
Figure 2C:
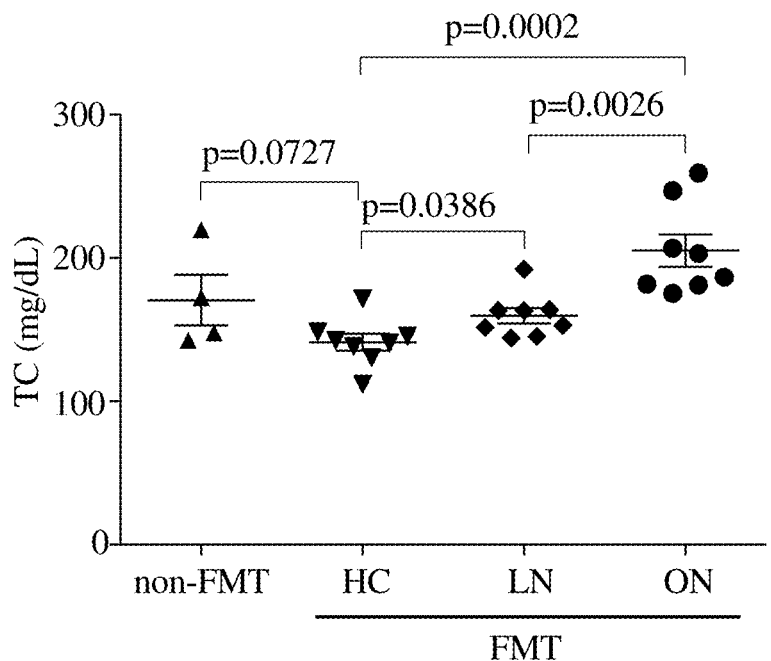

As depicted in FIG. 2B, FMT-Healthy, when compared to FMT-Lean and FMT-Obese, had significantly lower mean plasma triglyceride levels (110.0±7.12 mg/dL vs. 146.7±7.90 mg/dL and 207.9±11.52 mg/dL, p=0.0039 and p<0.0001 respectively). A similarly significant effect was seen in mean plasma total cholesterol levels (FIG. 2C, 141.3±75.93 mg/dL vs. 159.7±5.44 mg/dL and 205.2±11.23 mg/dL, p=0.0386 and p=0.0002 respectively).

Figure 2D:
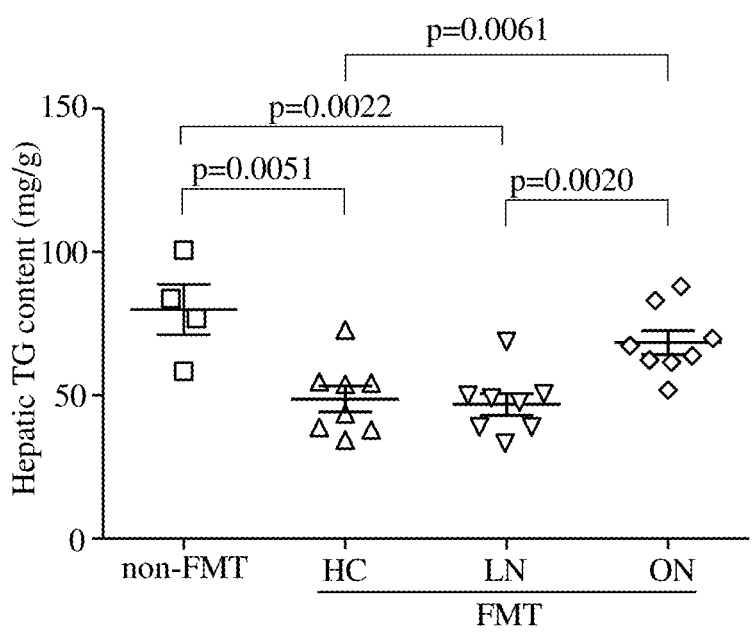
FIGS. 2D and 2E are graphs showing Hepatic triglyceride content (mg/g) and hepatic total cholesterol content (mg/g) from mice colonized with microbiota from healthy, lean NAFLD and obese NAFLD donors (n=8 in each group) and vehicle as non-FMT group.
Figure 2E:
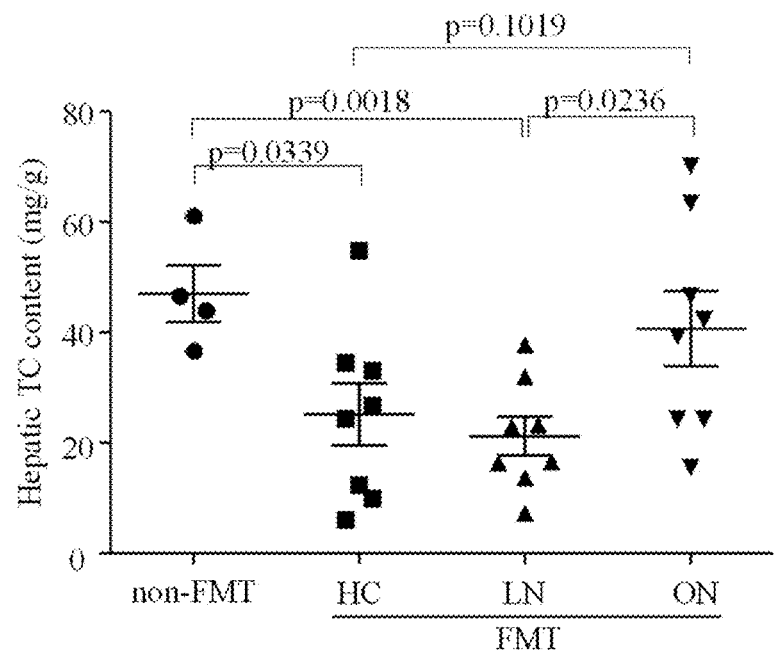

Histological analysis of liver tissues revealed a lower intrahepatic lipid accumulation in FMT-Healthy and FMT-Lean mice whereas higher in non-FMT and FMT-Obese mice. In addition, mean hepatic triglyceride (FIG. 2D) in FMT-Healthy and FMT-Lean mice were 48.80±4.46 mg/g and 46.89±3.86 mg/g respectively, significantly lower than that of non-FMT (79.93±8.75 mg/g, p=0.0051 and p=0.0022 respectively) and FMT-Obese (68.51±4.18 mg/g, p=0.0061 and p=0.0020 respectively). Similar results were noted for mean hepatic total cholesterol (FIG. 2E, all p<0.05).

Figure 2F:
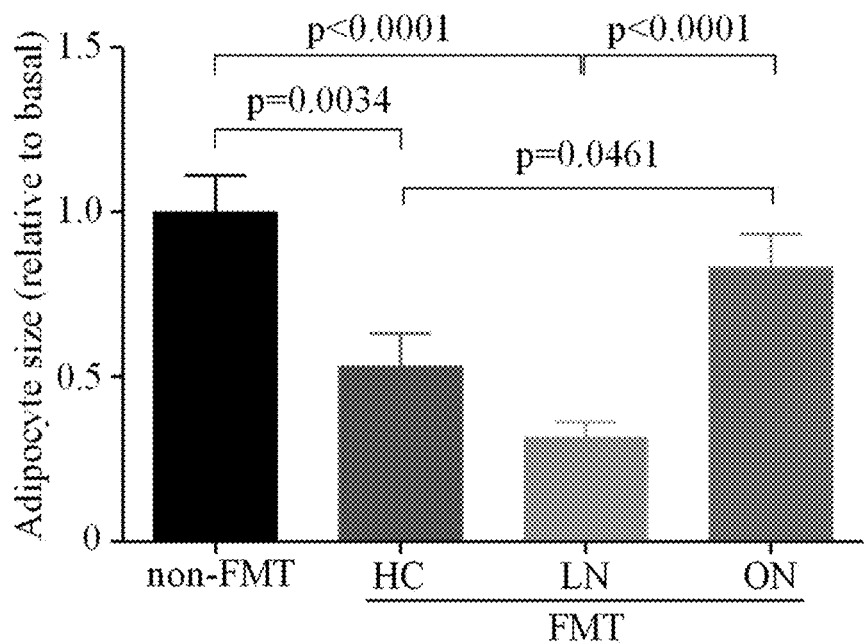
FIG. 2F is a graph showing mean adipocyte cell size from white adipose tissue of mice colonized with microbiota from healthy, lean NAFLD and obese NAFLD donors (n=8 in each group) and vehicle as non-FMT group. Quantification of adipocyte size using Image J software with Fiji package. Data were shown as mean±SEM. Significance between every two groups was calculated using unpaired two-tailed Student's t test. *p<0.05, **p<0.01.

Histological analysis of white adipose tissue (FIG. 2F) showed FMT-Healthy and FMT-Lean mice had a significantly smaller mean adipocyte cell size (0.53±0.10 and 0.32±0.04 respectively) compared to non-FMT (1.00±0.11, p=0.0034 and p<0.0001 respectively) and FMT-Obese (0.83±0.10, all p<0.0001). No significant differences were observed between FMT-Healthy vs. FMT-Lean mice.

Figure 3A:
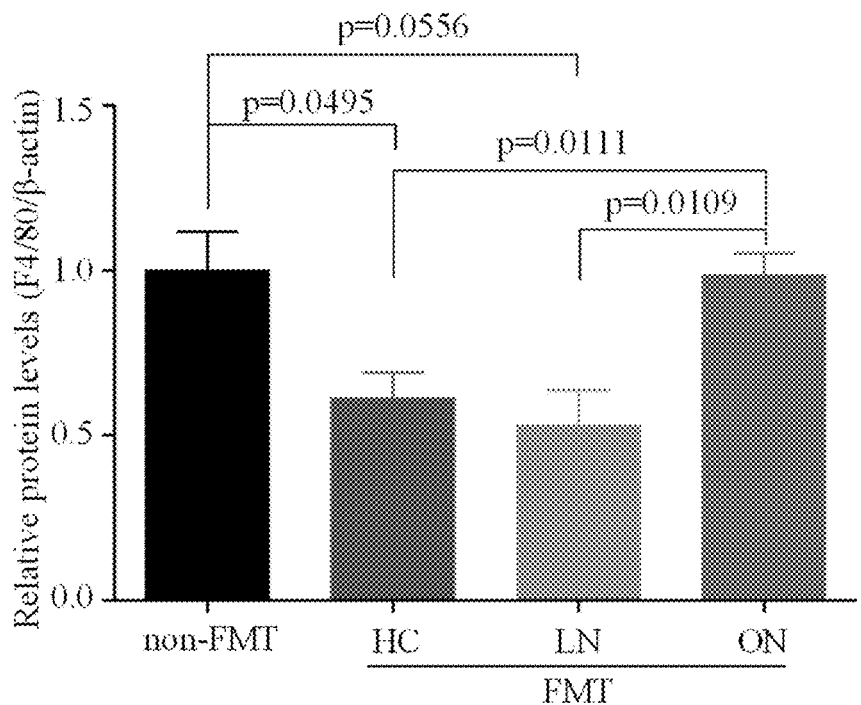
FIGS. 3A-3D are bar graphs showing Western blot analysis of F4/80, a macrophage-specific membrane marker in the liver tissues (FIG. 3A), relative fluorescence units of DHE staining (FIG. 3B), densitometric quantification of lysozyme from Western blot analysis of lysozyme protein levels in the ileum after FMT (FIG. 3C), and densitometric quantification of ZO-1, a tight junction gene zonula occludens-1 (ZO-1, a marker of gut permeability) in the ileum as assessed by Western blot (FIG. 3D). Data were shown as mean±SEM. Significance between every two groups was calculated using unpaired two-tailed Student's t test. *p-value<0.05, ** p-value<0.01.
Figure 3B:
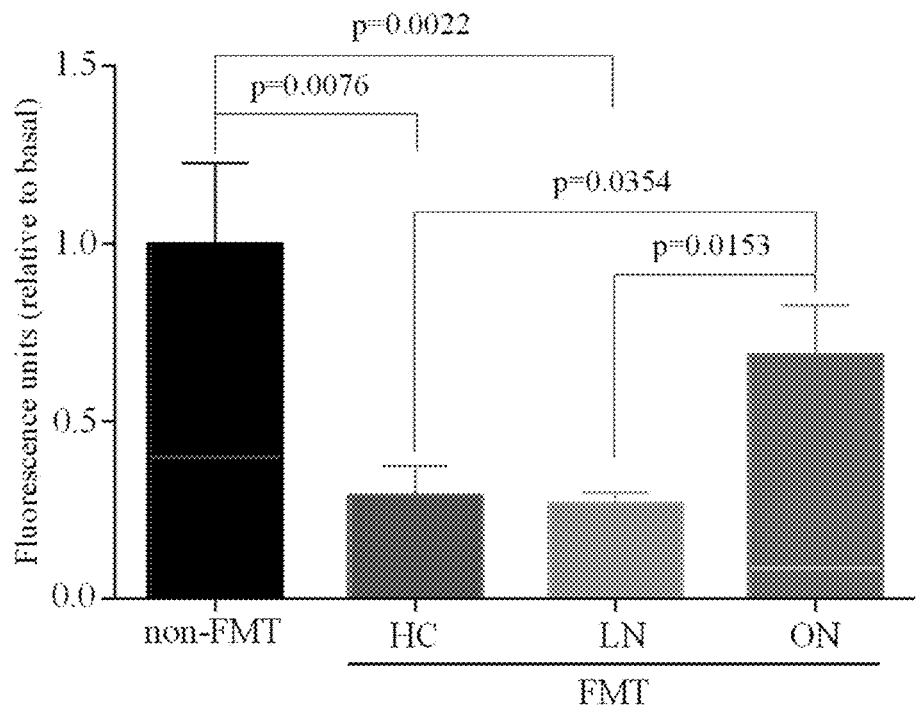

The Effects of Stool Microbes from Human Donors on Macrophage Infiltration, ROS Production and Intestinal Barrier Function The expression of macrophage-specific hepatic F4/80$^+$ cells was markedly decreased in FMT-Healthy and FMT-Lean mice when compared to non-FMT and FMT-Obese. As depicted in FIG. 3A, Western blot showed a significantly decreased relative mean F4/80 expression in FMT-Healthy and FMT-Lean (0.61±0.08 and 0.5317±0.11 respectively) when compared to FMT-Obese (0.99±0.07, p=0.0111 and 0.0109 respectively). Dihydroethidium stains of liver tissue demonstrated a markedly reduced hepatic ROS in FMT-Healthy and FMT-Lean when compared to non-FMT and FMT-Obese. The mean relative fluorescence units of dihydroethidium stains (FIG. 3B) in FMT-Healthy and FMT-Lean were 0.29±0.08 and 0.27±0.03 respectively, significantly lower than FMT-Obese (0.69±0.14, p=0.0354 and 0.0153 respectively) and non-FMT (1.00±0.23, p=0.0076 and 0.0022 respectively). Macrophage infiltration and hepatic ROS production are widely accepted to play an important role in the development and progression of NAFLD.

Figure 3C:
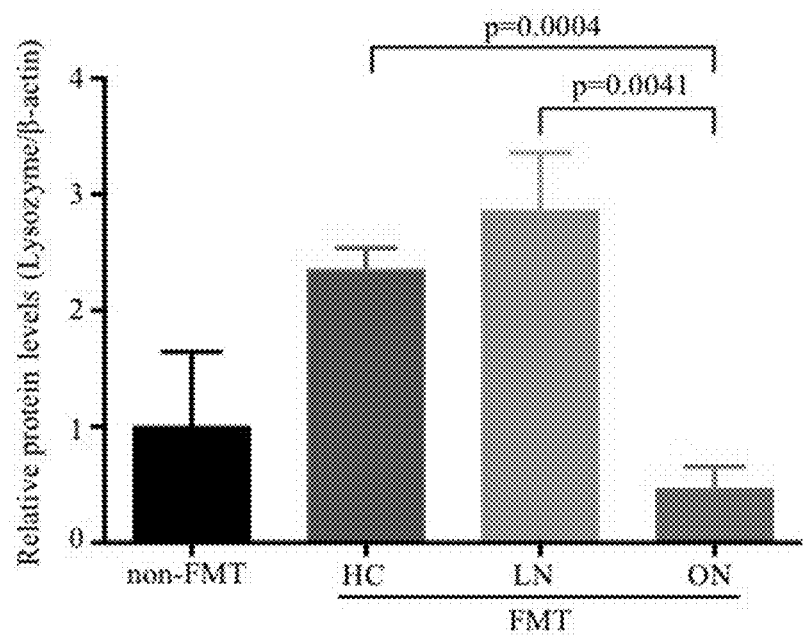
Figure 3D:
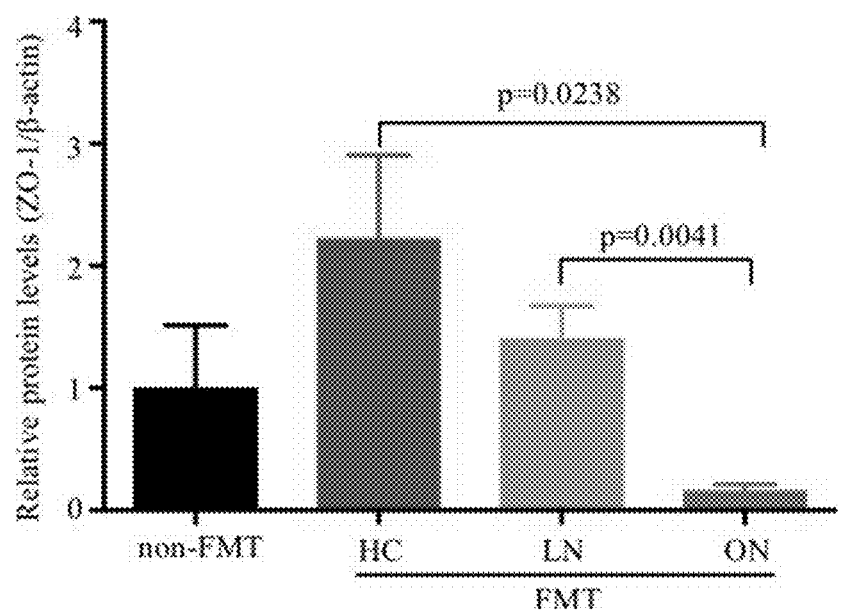

In the examination of FMT on intestinal barrier function, immunohistochemical staining showed that the expression of lysozyme, a marker of Paneth cell which clustered in the crypt base of ileum with antimicrobial function and host defense as described previously (Sato et al., Nature; 469: 415-418 (2011)), was markedly upregulated in FMT-Healthy and FMT-Lean mice compared to FMT-Obese. In Western blot analysis (FIG. 3C), the mean relative ileal lysosome protein levels in FMT-Healthy and FMT-Lean were 2.35±0.19 and 2.86±0.50 respectively, significantly higher than that of FMT-Obese (0.47±0.19, p=0.0004 and 0.0041 respectively). Similarly, as depicted in FIG. 3D, ileal ZO-1 expression as determined by Western blot was significantly increased in FMT-Healthy (2.22±0.68) and FMT-Lean (1.40±0.27) when compared to FMT-Obese (0.16±0.05, p=0.0238 and 0.0041 respectively).

Example 2. The Fecal Presence of *Lactococcus lactis* is Associated with Reduced NAFLD Risk

Materials and Methods

Materials and methods are as described for Example 1.

Results

Altered Microbial Profile in Post-FMT Mice and Causal Association with *Lactococcus lactis*

The microbial profiling at the genus level obtained from shotgun metagenomic sequencing of fecal samples of different mice groups was obtained. There was a distinct separation, among FMT-Obese mice when compared to FMT-Healthy and FMT-Lean (FIG. 4B and Table 3, both p<0.05).

Figure 4A:
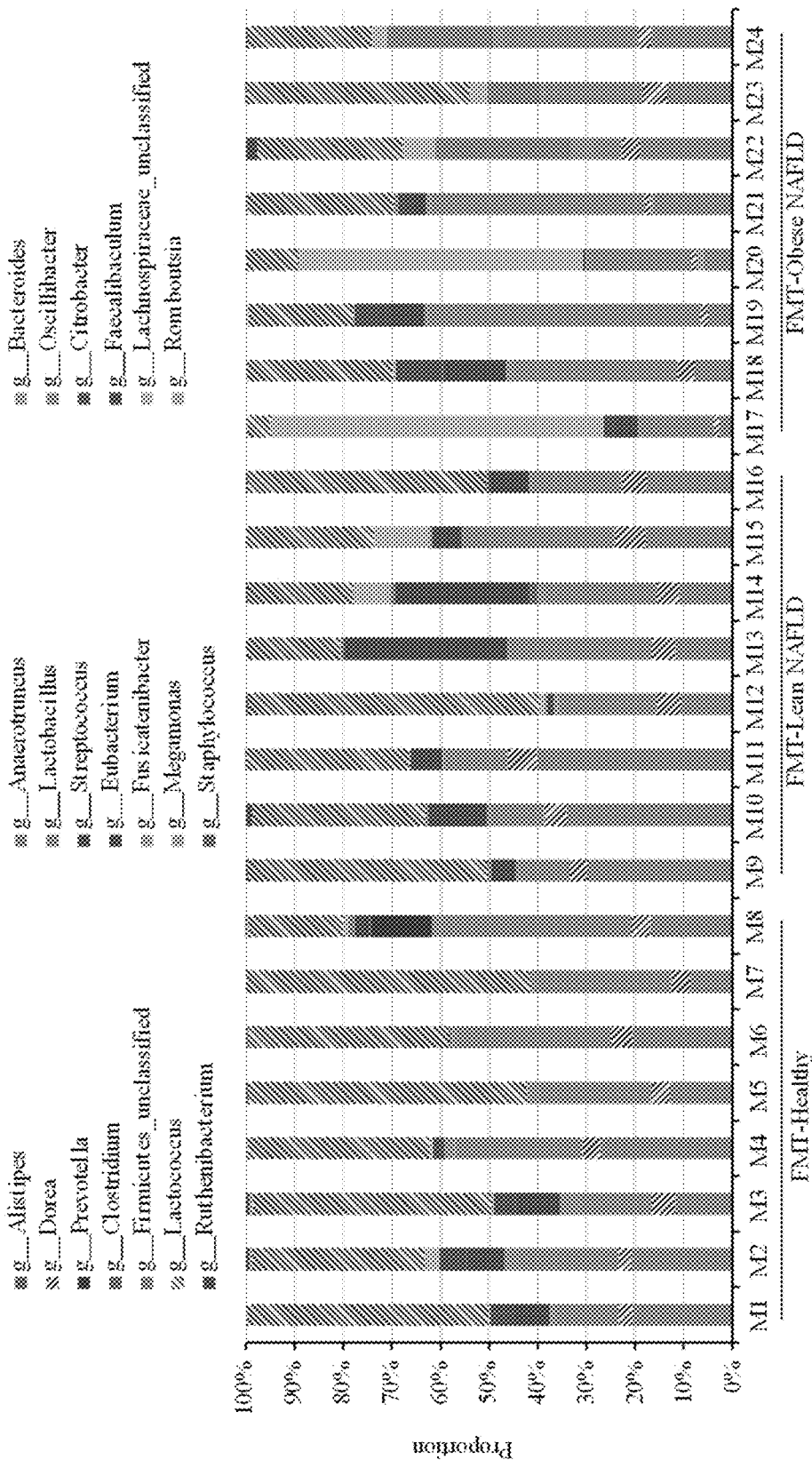
FIG. 4A is a graph showing the microbial profiles at the genus level.
Figure 4B:
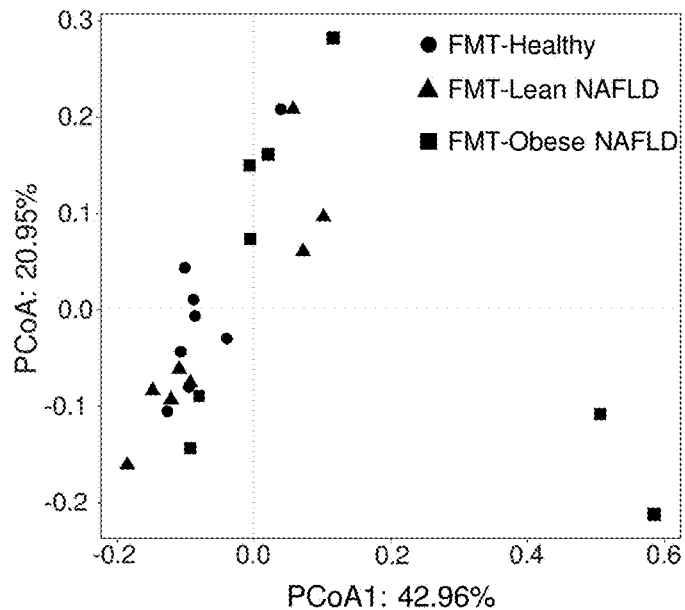
FIG. 4B is a dot plot of principal coordinates analysis of microbiota based on Bray-Curtis distance (a quantitative measure of community dissimilarity); Significance of different groups was calculated by permutational multivariate analysis of variance test with 9999 permutations.
Figure 4C:
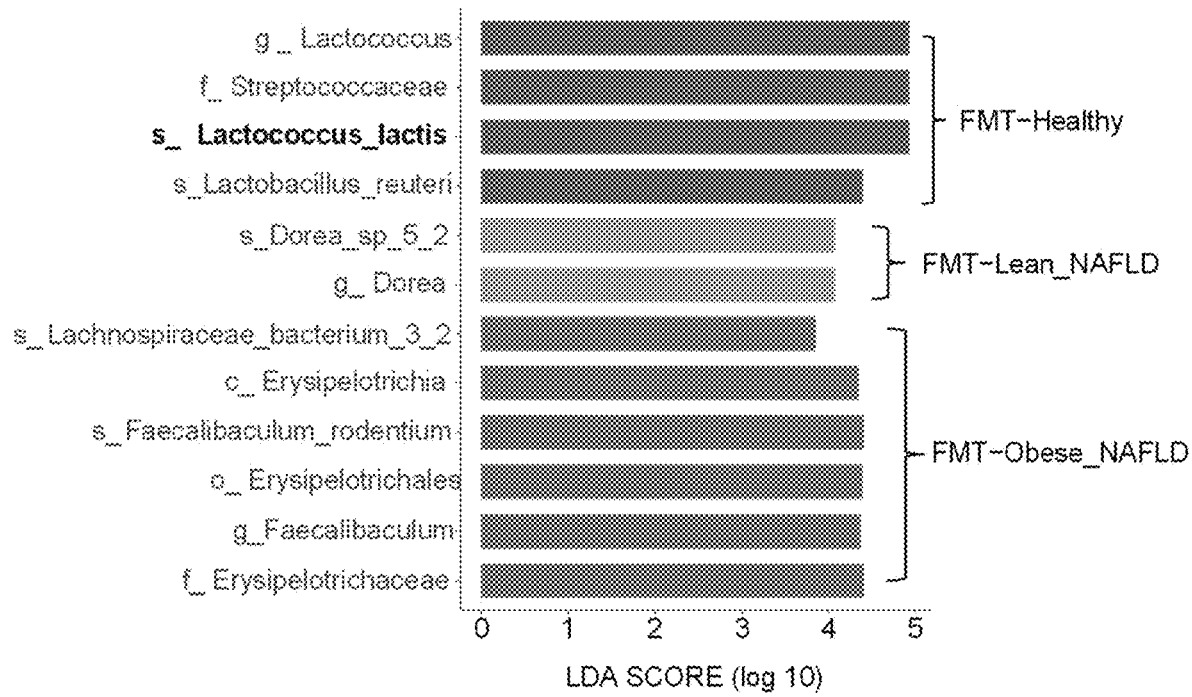
FIG. 4C is a graph showing Linear discriminant analysis (LDA) effect size (LEfSe) method to identify fecal biomarkers in post-FMT mice; LDA scores provided for differential taxon abundance among different groups; The presence of *Lactococcus lactis* in FMT-healthy mice was identified with the highest LDA score.
Figure 4D:
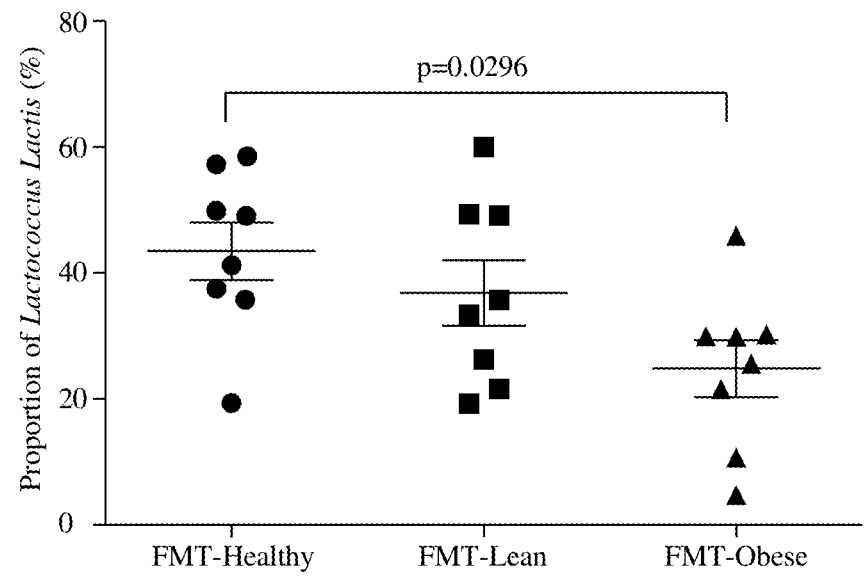
FIG. 4D is a graph showing proportion (%) of *Lactococcus lactis* in post-FMT mice. One-way ANOVA followed by Tukey's multiple comparisons test was adopted to calculate the significance.
Figure 4E:
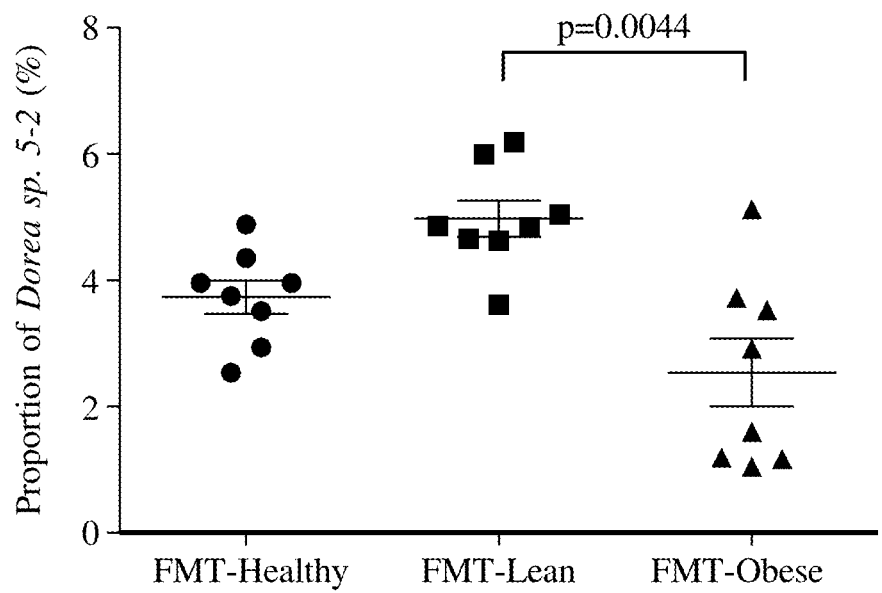
FIG. 4E is a graph showing proportion (%) of *Dorea* sp. 5-2 in post-FMT mice. One-way ANOVA followed by Tukey's multiple comparisons test was adopted to calculate the significance.

Differential taxonomic abundance among different mice groups via linear discriminant analysis (LDA) effect size method is depicted in FIG. 4C. *Lactococcus lactis* present in FMT-Healthy mice had the highest log LDA score 4.9306 when compared at the species level with higher mean abundance than *Lactobacillus reuteri* (43.50±4.57% vs. 8.72±1.37%, p<0.0001, see also FIG. 4A). The results also demonstrated *Lactococcus lactis* to be of significantly higher mean abundance in FMT-Healthy mice when compared to FMT-Obese (43.50±4.57% vs 24.82±4.51%, p=0.0296) (FIG. 4D). No significant differences were observed between FMT-Healthy vs. FMT-Lean (p>0.05). *Dorea* sp. 5-2 had the highest log LDA score 4.0765 in FMT-Lean mice, with significantly higher mean abundance than that in FMT-Obese mice (4.98±0.29% vs. 2.54±0.54%, p=0.0044, FIG. 4E).

Figure 5A:
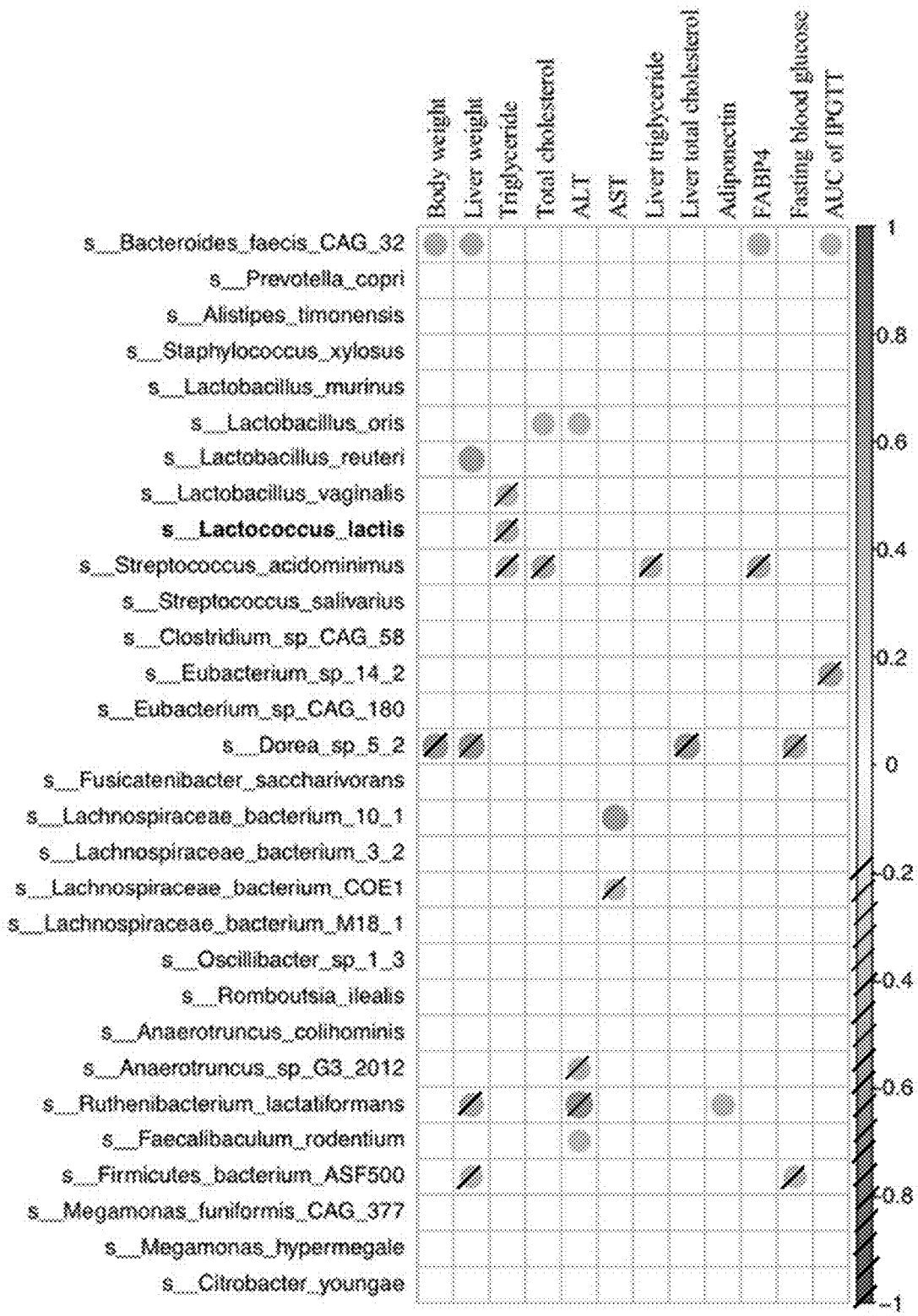
FIG. 5A is a heatmap of the Spearman's rank correlation coefficient between species and metabolic parameters as filtered by |rho|>0.3, p-value (adjusted by Benjamini-Hochberg)<0.05. A dot indicates a positive correlation and a crossed dot indicates a negative correlation. AUC, area under the curve; FABP4, fatty acid-binding protein 4; FMT, fecal microbiota transplantation; IPGTT, intraperitoneal glucose tolerance test.

The 16S rRNA gene sequences from the study data were aligned to NCBI database (National Center for Biotechnology Information, U.S. National Library of Medicine). Based on the blast result, five *Lactococcus lactis* strains (CF102, 104, 109, MGYG-HGUT-00226, and *Lactococcus lactis*) and two *Lactococcus lactis* subsp. *lactis* strains (CF111 and 112) were annotated from whole genome shotgun sequence in post-FMT mice (Table 5). Heatmap displayed the correlation between metabolic parameters and species and indicated that *Lactococcus lactis* correlated negatively with circulating triglycerides levels (rho=−0.45, p=0.03, FIG. 5A). In addition, *Dorea* sp. 5-2 correlated negatively with body weight (rho=−0.56, p=0.0043) and liver weight (rho=−0.58, p=0.0027) (FIG. 5A).

Figure 5B:
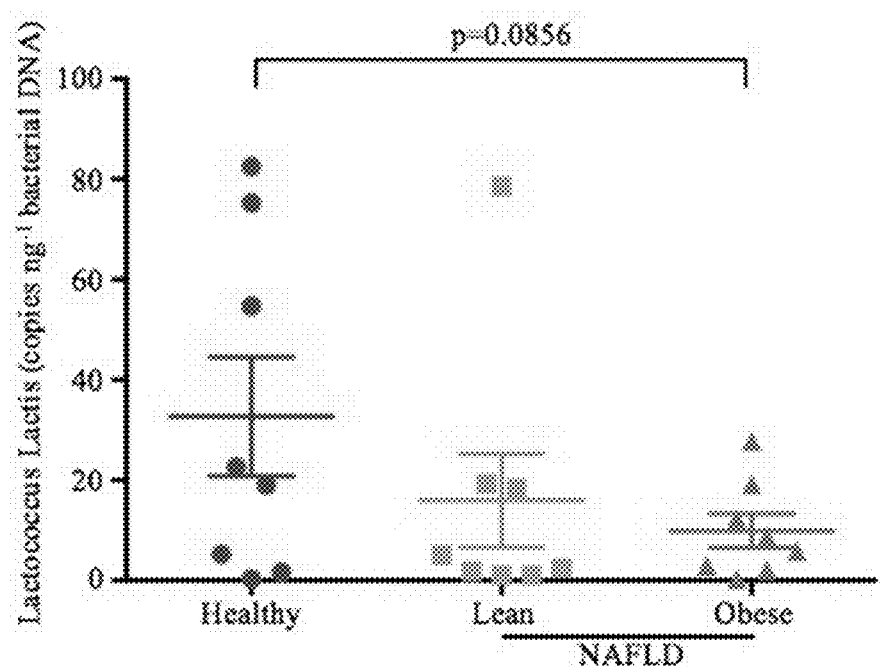
FIG. 5B is a graph showing the fecal abundance of *Lactococcus lactis* as quantified by targeted quantitative Polymerase Chain Reaction; Data were showed as mean±SEM. Significance was calculated by Kruskal-Wallis followed by Dunn's multiple comparison test. *p<0.05, **p<0.01.

When performing quantitative detection of *Lactococcus lactis* in human donor stool, higher mean abundance of *Lactococcus lactis* was observed in healthy donors (32.67±11.84 copies/ng bacterial DNA), borderline significantly higher than that of obese NAFLD donors (9.01±3.36 copies/ng bacterial DNA, p=0.0856, FIG. 5B).

Figure 6A:
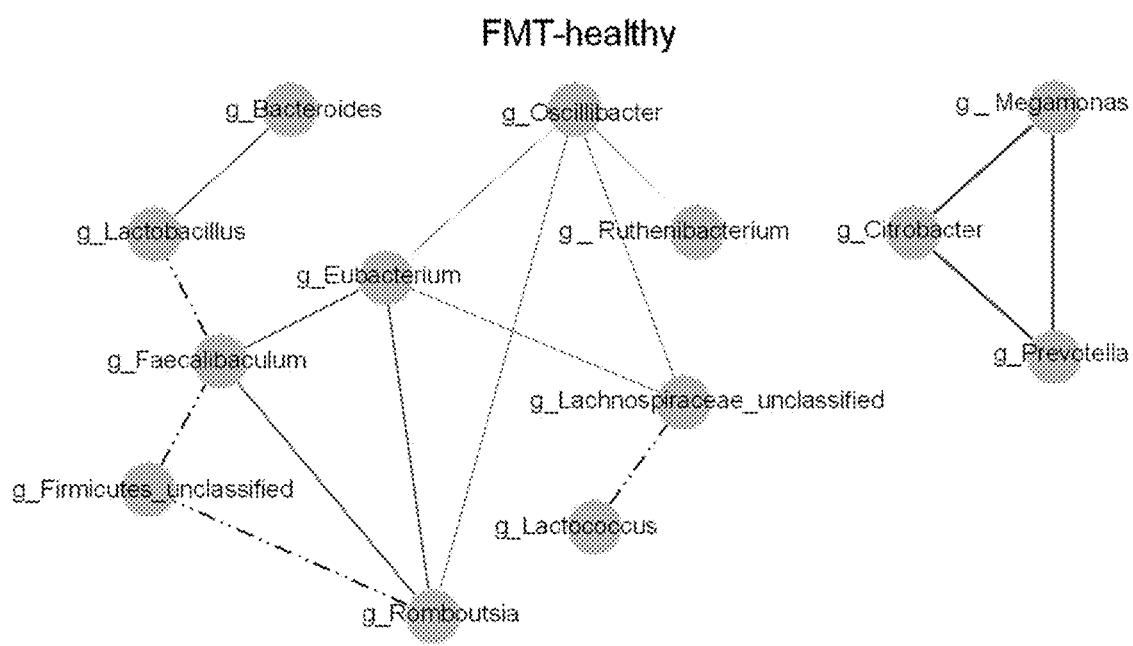
FIGS. 6A-6C are diagrams showing the co-occurrence networks filtered by |rho|>0.3, p-value (adjusted by Benjamini-Hochberg)<0.05 were used to understand the relationship between *Lactococcus* and other genera at the genus level under different groups. Red line indicated a positive correlation and blue crossed line indicated a negative correlation. Kruskal-Wallis test was adopted to calculate the significance.
Figure 6B:
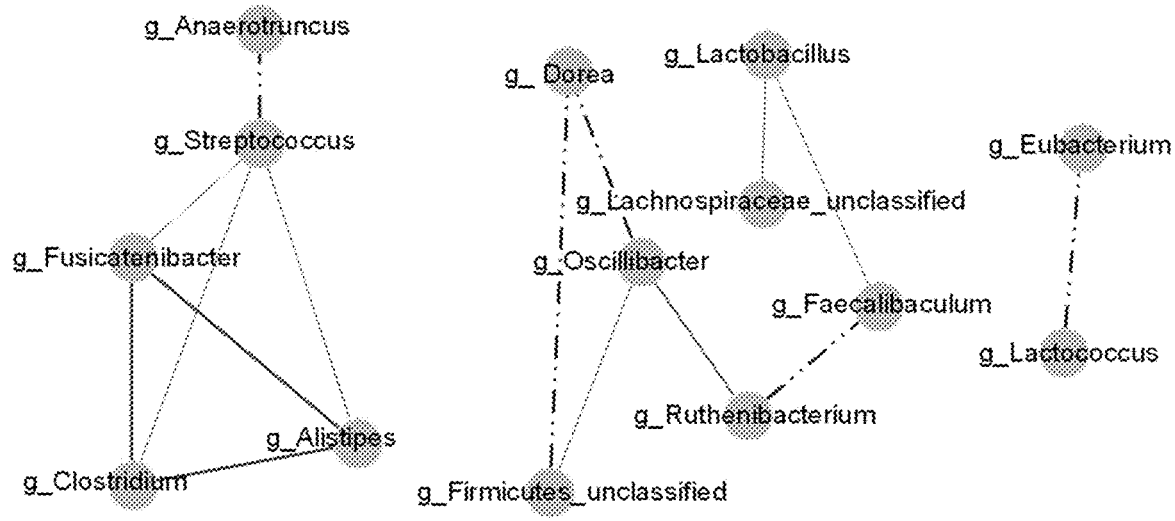
Figure 6C:
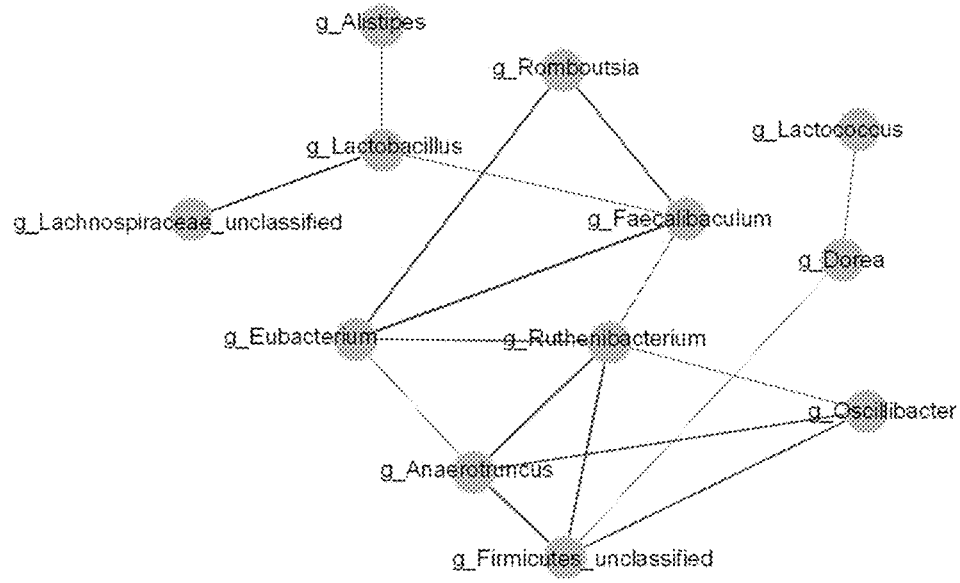
Figure 6D:
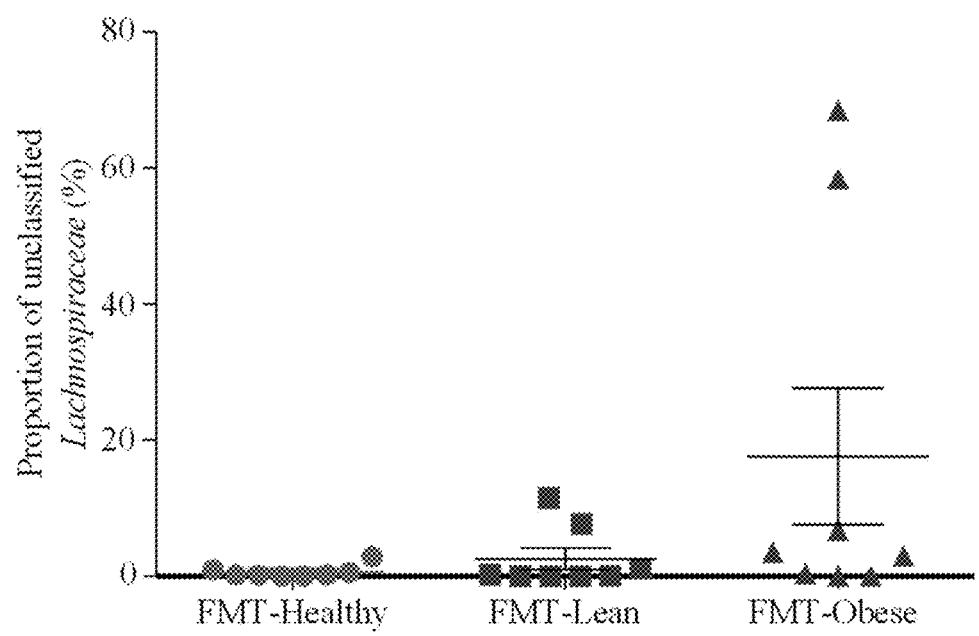
FIG. 6D is a graph showing unclassified Lachnospiraceae in post-FMT mice. One-way ANOVA followed by Tukey's multiple comparisons test was adopted to calculate the significance.

Co-Occurrence Among Taxa and Correlation Between Differential Pathways and Bacterial Species in Post-FMT Mice The co-occurrence networks were used to understand the relationship between *Lactococcus* and other genera in post-FMT mice. In FMT-healthy mice, *Lactococcus* had a negative correlation (rho=−0.83, p=0.0102) with unclassified Lachnospiraceae, an obesogenic bacterium with association with type 2 diabetes and obesity. A negative correlation (rho=−0.79, p=0.0208) was also demonstrated with *Eubacterium*, a member of Lachnospiraceae family known for its association with obesity in FMT-Lean mice. No association between *Lactococcus* and the aforementioned 2 genera was observed in FMT-Obese group (FIG. 6A-6C). This might suggest that the lower abundance of *Lactococcus* in this group could not control the outgrowth of such bacteria especially Lachnospiraceae, which showed the highest median abundance (17.63±10.09%) in FMT-Obese group when compared to that in FMT-Lean (2.59±1.58%) and FMT-Healthy group (0.64±0.34%) although statistically not significant (FIG. 6D).

Annotation of Microbial Function

Figure 7A:
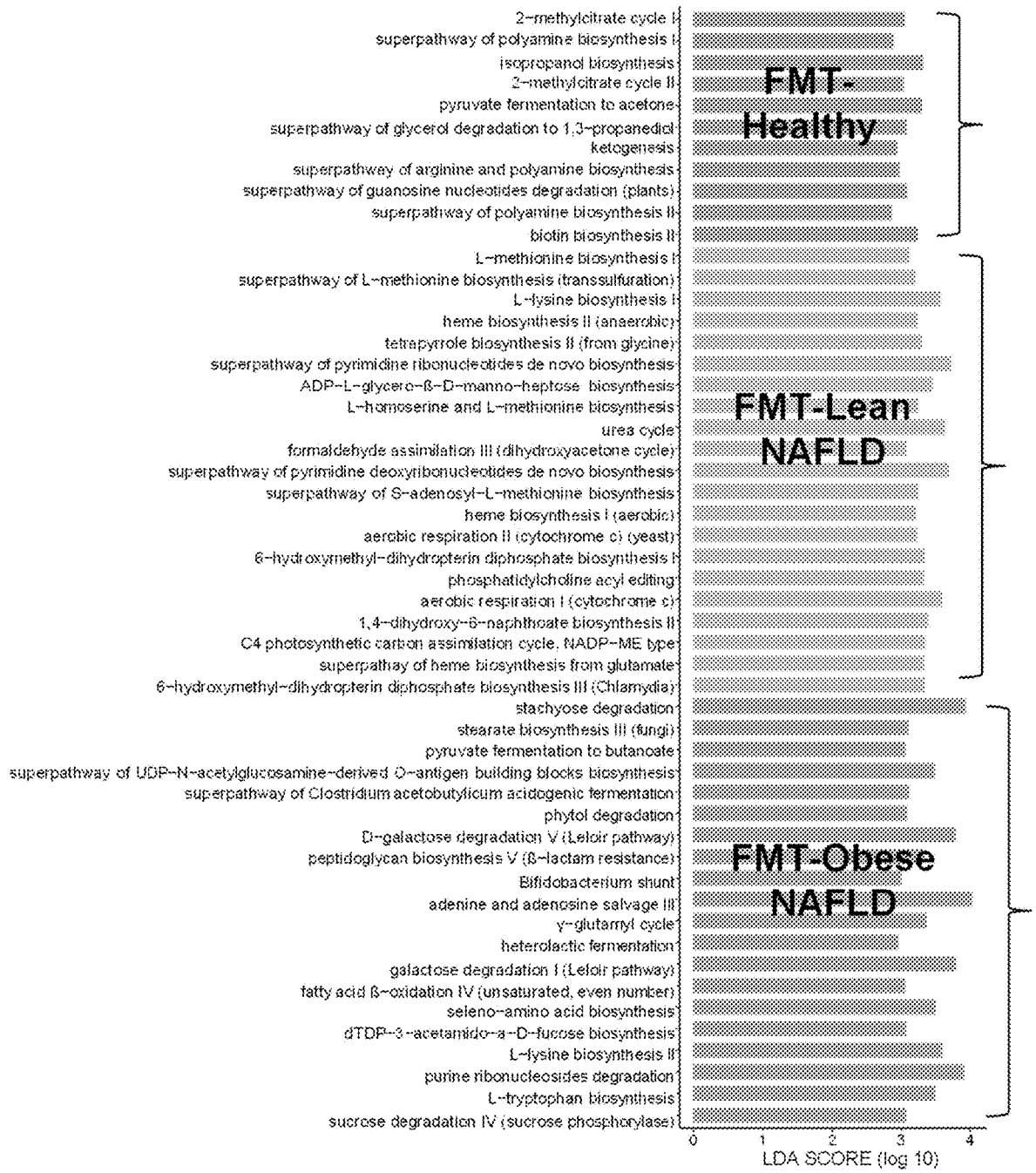
FIG. 7A is graph showing Linear discriminant analysis (LDA) effect size (LEfSe) method was used to screen the differential pathways.
Figure 7B:
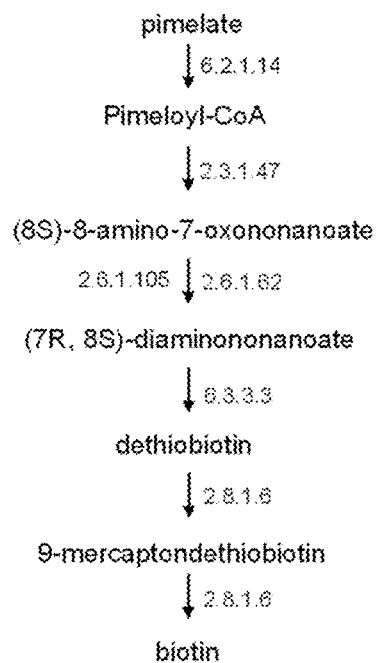
FIG. 7B is a diagram of enzymic reactions from biotin biosynthesis II pathway.
Figure 7C:
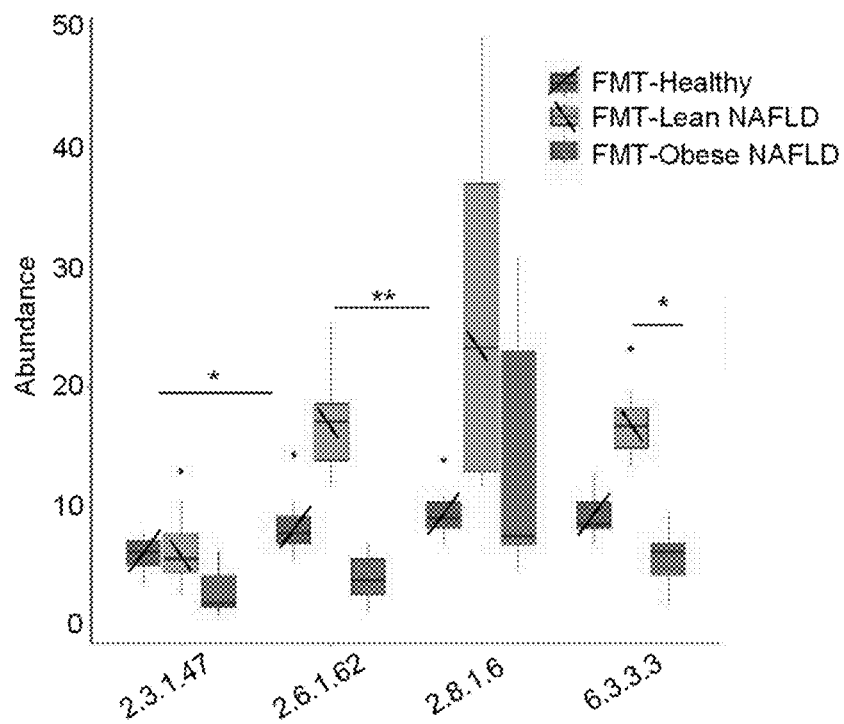
FIG. 7C is a graph showing the differential enrichment (copies per million) of processing gene involved in biotin biosynthesis. Significance was calculated using unpaired Mann-Whitney U test. *p-value<0.05, ** p-value<0.01.

In the annotation of microbial genes to the MetaCyc database, 11, 21 and 20 pathways were significantly altered in FMT-Healthy, -Lean and -Obese mice, respectively (FIG. 7A). When comparing FMT-Obese with FMT-Healthy, significantly higher mean enrichments of 8-amino-7-oxononanoate synthase (Enzyme Commission (EC) number 2.3.1.47, 6.11±0.56 vs. 2.94±0.70 copies per million, p<0.05), 8-amino-7-oxononanoate transaminase (EC 2.6.1.62, 8.52±1.00 vs. 4.08±0.75 copies per million, p<0.01), and dethiobiotin synthetase (EC 6.3.3.3, 9.24±0.70 vs. 5.69±0.86 copies per million, p<0.05) of biotin biosynthesis pathway was observed in FMT-Obese mice (FIGS. 7B and 7C).

Figure 7D:
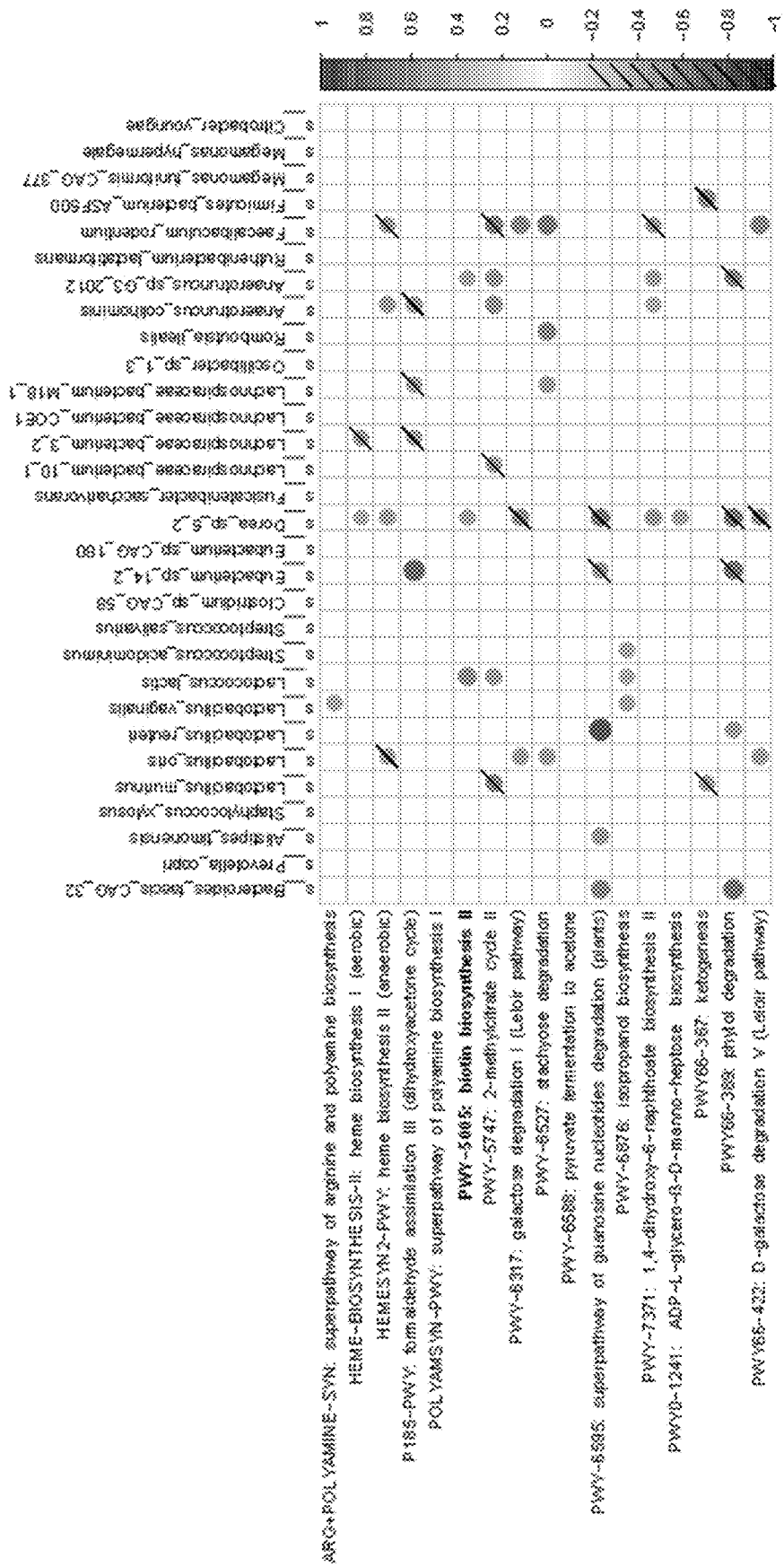
FIG. 7D is a heatmap of the Spearman's rank correlation coefficient between differential pathways and species was filtered by |rho|>0.3, p-value (adjusted by Benjamini-Hochberg)<0.05. A dot indicates a positive correlation, and a crossed dot indicates a negative correlation. *Lactococcus lactis* column is indicated with a box.
Figure 7E:
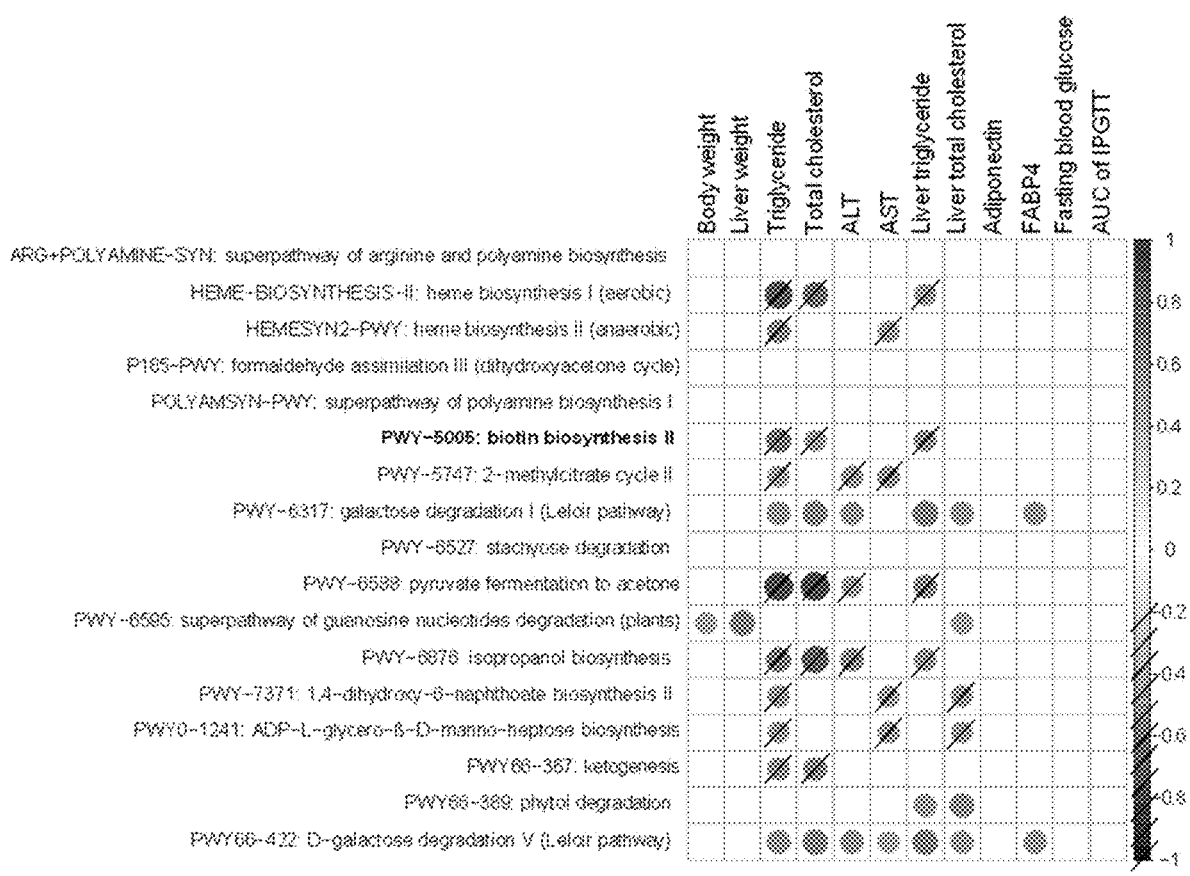
FIG. 7E is a heatmap of the Spearman's rank correlation coefficient between pathways and metabolic parameters was filtered by |rho|>0.3, p-value (adjusted by Benjamini-Hochberg)<0.05. A dot indicates a positive correlation, and a crossed dot indicates a negative correlation.
Figure 8:
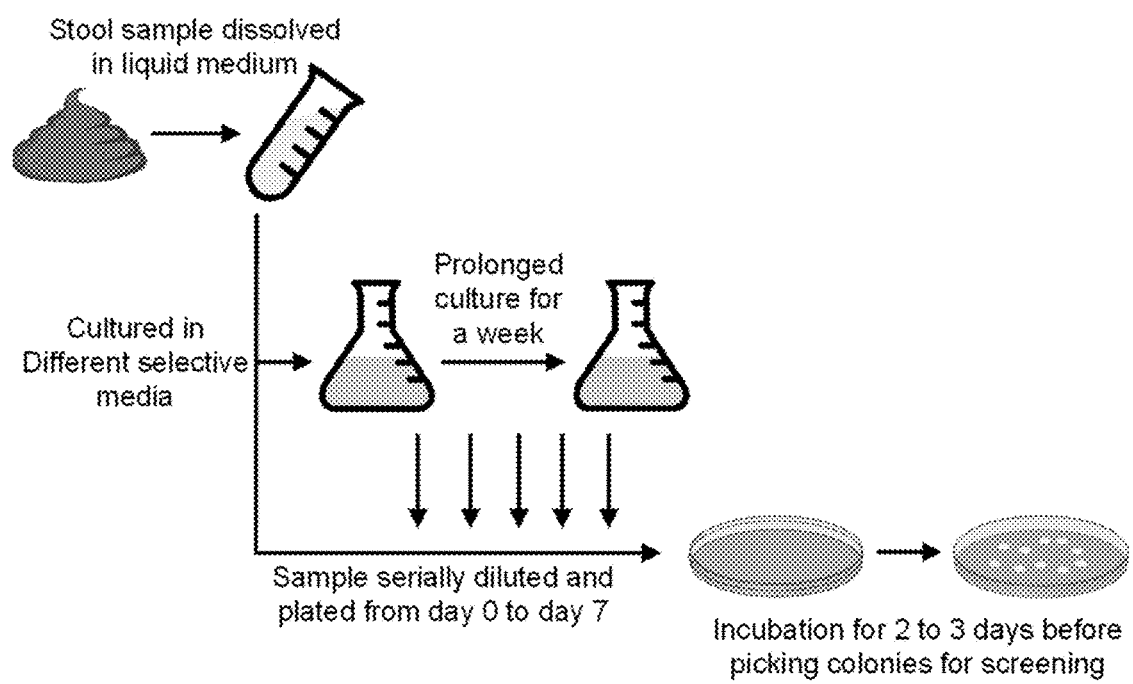
FIG. 8 is a schematic of the protocol for the isolation of *Lactococcus lactis* obtained from the stool samples of the mouse and human subjects. 100 mg of the stool samples from the mice were first diluted and dissolved in 500 µl brain heart infusion (BHI) broth. The fecal mixture was then serially diluted for plating on BHI agar to obtain individual bacteria as a single colony. The agar plates were then incubated at 30° C. for 2 to 3 days. Next, colonies on the plate were selected for screening. The remaining fecal mixture was further cultured in different selective media for one week. These cultures were sampled every day and plated on agar for PCR screening.

Concerning correlation analysis, *Lactococcus lactis* had the strongest positive correlation with biotin biosynthesis pathway (rho=0.59, p=0.0075, FIG. 7D, boxed column) Biotin biosynthesis pathway correlated negatively with circulating triglycerides levels (rho=−0.56, p=0.0047), circulating cholesterol levels (rho=−0.44, p=0.0324), and intra-hepatic triglycerides content (rho=−0.46, p=0.0235, FIG. 7E). The second strongest correlation was found with the 2-methylcitrate cycle (rho=0.46, p=0.0234, FIG. 7D), which also correlated negatively with circulating triglycerides levels (rho=−0.42, p=0.0420, FIG. 7E).

TABLE 5

Annotations of the 16S rRNA gene sequences.

| | NCBI Accession ID |
|---|---|
| *Lactococcus lactis* subsp. *lactis* strain CF111 | NZ_OLME01000004.1 |
| *Lactococcus lactis* subsp. *lactis* strain CF112 | NZ_OLMC01000021.1 |
| *Lactococcus lactis* isolate CF104 | NZ_OESK01000004.1 |
| *Lactococcus lactis* isolate CF109 | NZ_OESI01000004.1 |
| *Lactococcus lactis* isolate CF102 | NZ_OESF01000012.1 |
| *Lactococcus lactis* isolate MGYG-HGUT-00226 | NZ_CABJEC010000008.1 |
| *Lactococcus lactis* isolate *Lactococcus lactis* | NZ_OGTW02000193.1 |

Discussion

While emerging evidence has linked the gut microbiome to the development of NAFLD, underlying causality has not been well-investigated. This study identified a causal relationship between the gut microbiota and NAFLD. In addition, a specific bacterium, *Lactococcus lactis*, may have a therapeutic function for NAFLD.

The data of FMT modulating the development of NAFLD in human studies has not been convincing (Craven et al., *Am*

*J Gastroenterol;* 115:1055-1065 (2020); and Vrieze et al., *Gastroenterology;* 143:913-916 (2012)), and it can be influenced by numerous factors including variations in study design and sample size. The human microbiota-associated model has the advantage of establishing causal relationships between an altered microbiome and disease if the taxon in question is able to colonize in the recipient animal. In this study, the mice were fed with microbiota from healthy, lean NAFLD and obese NAFLD donors. Donor liver steatosis were quantified with CAP measurements via VCTE, with all obese NAFLD donors within the range of severe steatosis (>280 dB/m). FMT demonstrated a differential causal role in the development of fatty liver disease in human microbiota-associated mice following exposure to a high-fat diet, as evidenced by the changes in mice intrahepatic lipid accumulation, intrahepatic triglyceride and total cholesterol levels, and adipocyte cell size (FIGS. 2A-2F). This study additionally found FMT from non-obese donors causally altered processes integral to NAFLD development, including macrophage infiltration and hepatic ROS generation (FIGS. 3A-3D). Markers of intestinal barrier function, including ileal lysozyme expression and ZO-1, were affected, further illustrating the microbiome modulation involves the increase of intestinal permeability and the development of a "leaky gut."

The second important finding of the study was the identification of a specific bacterium, *Lactococcus lactis*, which may intervene in NAFLD development. Mice colonized with healthy microbiota exhibited a remarkable higher abundance of *Lactococcus lactis* but not in mice colonized with obese NAFLD microbiota. Moreover, the abundance of *Lactococcus lactis* negatively correlated with triglycerides in circulation, indicating that this species can be a biomarker linking gut microbiota and NAFLD status. *Lactococcus lactis* is extensively used in the fermentation of buttermilk due to the capability of producing lactic acid and has been generally recognized as a rare opportunistic pathogen in human (Shimizu et al., *J Infect Chemother;* 25:141-146 (2019)). Buttermilk is a traditional dietary remedy for patients with fatty liver disease (Jeznach-Steinhagen et al., *Medicina (Kaunas);* 55:166 (2019)). Skim milk fermented by *Lactococcus lactis* has been reported to have antidiabetic effects (Yadav et al., *Biosci Biotechnol Biochem;* 70:1255-1258 (2006)), and its subspecies *Lactococcus lactis* ssp. *cremoris* may protect against diet-induced metabolic changes (Naudin et al., *Gastroenterology;* 159:639-651 (2020)). Although these are consistent with the current findings, these previous findings are in animals and their applicability to humans was not demonstrated. Further, their purpose was to investigate the potential of existing standard *L. lactis* strains for treatment in animal models. This type of intervention study could not identify biomarkers and that was not their purpose. The discovery disclosed herein uses human microbiota transplanted mice and confirms, for the first time, consistent biomarkers in both human and human microbiota transplanted mice.

Moreover, mice colonized with microbiota from lean NAFLD donors showed a favorable metabolic profile than those with microbiota from obese NAFLD donors. Their underlining metabolism may be quite different from FMT-Obese mice, which deserves further attention. Although no significant difference was observed in *Lactococcus lactis* between FMT-Lean and FMT-Obese, the LEfSe analysis tool indicated a greater prominence of species *Dorea* sp. 5-2 in FMT-Lean mice. An increase in *Dorea* was identified as a gut microbiota signature of NAFLD onset (Del Chierico et al., *Hepatology* (Baltimore, Md); 65:451-464 (2017)). There was a negative correlation with body weight and liver weight (FIG. 5A), which was congruent with previous studies (Chen et al., *Hepatology* (Baltimore, Md); 71:1213-1227 (2020)). However, the role of *Dorea* sp. 5-2 in the development of lean NAFLD is still unknown. *Dorea* sp. 5-2 may signify the onset of NAFLD, and it may take time for the metabolic-related phenotypes e.g., obesity to appear. Pathophysiological difference between NAFLD phenotypes observed in this study supports the causal effect of gut microbiota on obese NAFLD while lean NAFLD could be due to genetic predisposition as previously described (Feldman et al., *Am J Gastroenterol;* 112:102-110 (2017)).

The functional association of *Lactococcus lactis* with the biotin biosynthesis pathway is also described. Biotin is an essential micronutrient that functions as a cofactor for several carboxylase enzymes with key roles in metabolism, and has a role in reducing hypertriglyceridemia (Revilla-Monsalve et al., *Biomed Pharmacother;* 60:182-185 (2006), and Larrieta et al., *Eur J Pharmacol;* 644:263-268 (2010)), although its function in hepatic steatogenesis is not well-defined (Li et al., *Integr Med Insights;* 11:19-25 (2016)). In this study, the increasing capability of producing biotin was found in FMT-Healthy microbiota but not in FMT-Obese. Impaired intestinal barrier function may contribute, by affecting the absorption and processing of the micronutrients (Li et al., *Integr Med Insights;* 11:19-25 (2016)), although it remains unclear whether biotin generated by gut microorganisms contributes significantly to host biotin absorption (Zempleni et al., *J Nutr Biochem;* 10:128-138 (1999)). Secondly, 2-methylcitrate cycle, which can produce intermediates pyruvate and succinate, positively correlated with *Lactococcus lactis*, but negatively correlated with circulating triglyceride level. Succinate was reported as a danger signal that induces IL-1β (Tannahill et al., *Nature;* 496:238-242 (2013)). The data show *Lactococcus lactis* could play a role in NAFLD development via these metabolites, however, the exact mechanistic role will require further study.

*Lactococcus lactis* has not been recognized as a natural inhabitant of human gastrointestinal tract (Gotoh et al., *Biosci Microbiota Food Health;* 39:19-22 (2020)). Although healthy stool donors had a borderline significantly higher mean abundance of *Lactococcus lactis* when compared to obese NAFLD donors (FIG. 5B), its quantity (32.67±11.84 copies/ng bacterial DNA) was still much lower than that of other common fecal microbes as profiled via shotgun metagenomic sequencing. The majority of the probiotics are dietary supplement ingredients that confer a benefit to host health but are mainly limited to *Lactobacillus* ssp. and *Bifidobacterium* ssp. Currently, next-generation probiotics or live biotherapeutic products are emerging and are different from traditional probiotics by being tailored as a specific treatment for disease. Potential investigational candidates include Akkermansia muciniphila for atherosclerosis and *Bacteroides thetaiotaomicron* for obesity. *Lactococcus lactis* could be developed as a next-generation probiotic to prevent NAFLD development; this can be crucially momentous given the current limited available pharmaceutical agents for NAFLD treatment.

A limitation of this study was the use of antibiotic gavage in eliminating the presence of gut microbiota in C57B/6J mice since germ-free mice and associated breeding facilities were not available in our institute. Intestinal microbiota plays a crucial role in gut and host immune system development, and a germ-free environment may not be intrinsically representative of associated immune and metabolic processes. The current antibiotic gavage-based model was adopted, which is broadly available and more economical, and successfully achieved substantial engraftment of human microbiota after FMT. The recommendations of human microbiota-associated models were adhered to and no pooling of the fecal samples of human donors was conducted. Pooling can eliminate the variation between individuals and may falsely inflate any statistical interference observed (Lazic et al., *PLoS Biol;* 16: e2005282 (2018)).

The stool microbes from healthy human donors prevented the development of NAFLD in mice, signifying a potential causal relationship. The fecal presence of *Lactococcus lactis* as a biomarker was associated with a reduced risk of NAFLD development. Colonization with fecal microbiota from healthy and lean NAFLD but not obese NAFLD donors prevented the development of fatty liver. The abundance of *Lactococcus lactis* was markedly decreased in mice transplanted with obese NAFLD microbiota and was positively correlated with biotin biosynthesis pathway but correlated negatively with plasma triglyceride levels. The findings of the current study identified a previously unknown causal relationship between NAFLD and gut microbiota and highlighted the functional role and therapeutic potential of *Lactococcus lactis*.

Example 3: Isolation and Typing of *Lactococcus lactis* Inhabited in Human and Animal Gastrointestinal Tract In Example 1 and Example 2, it was demonstrated that *Lactococcus lactis* was correlated with reduced NAFLD risk in a human-microbiota-associated (HMA) mouse model. Isolation and culture of *Lactococcus lactis* from healthy animals or human donors provided further evidence of the beneficial effects of the bacteria in varying settings.

Materials and Methods

Stool Samples

Using HMA mouse model, mice transplanted with fecal microbiota from healthy human donors were protected from diet-induced nonalcoholic fatty liver disease. Stool samples from these mice were selected for bacterial isolation because these mice possessed the highest proportion of *Lactococcus lactis* in their stool. For comparison, fresh stool samples from healthy donors were collected for isolation of *Lactococcus lactis*. The criteria of health donors included body mass index <25 kg/m$^2$; absence of fatty liver, controlled attenuation parameter measurements <248 dB/m via vibration controlled transient elastography (Fibroscan, Echosens, Paris) (Thomas et al. (2017) *Journal of Hepatology,* 66(5): pages 1022-1030); no significant alcohol intake, no antibiotic intake, and no laxative usage within the past twelve months.

Isolation of *Lactococcus lactis*

To isolate the *Lactococcus lactis,* 100 mg of the mouse stool sample was first diluted and dissolved in 500 µl brain heart infusion (BHI) broth. The amount of culturable bacteria in the fecal slurry varies in different samples. The fecal mixture was serially diluted for plating on BHI-infused agar plates to obtain optimal separation and resolution. The agar plates were then incubated at 30° C. for 2 to 3 days. Next, colonies on the plate were sampled for screening using polymerase chain reaction (PCR) and catalase activity test. The remaining fecal mixture was further cultured for one week in 6 ml BHI broth buffered at varying pHs, including pH 7.4, pH 5.8 and pH 4.6. These cultures were sampled every day and screening for *Lactococcus lactis* was performed as described below (FIG. 7). The protocol for bacterial isolation from the human fecal sample was the same except that 1 gram of fresh stool sample was diluted in 5 ml broth for ease of handling.

PCR Screening for *Lactococcus lactis*

Colonies were selected from the agar plate and diluted to produce liquid cultures which were used as templates for PCR screening. Several primer pairs were used to determine the genotypes of the bacteria (Table 6). The screening for *Lactococcus lactis* was performed by PCR using a *Lactococcus*-specific primer pair. PCR genotyping using three other primer pairs further confirmed isolates as *Lactococcus lactis*. The differentiation of subspecies was also based on PCR genotyping using primers specified for subspecies *lactis* and subspecies *cremoris*. Moreover, the presence of citrate permease gene tested by PCR determined the different bio-variants of the bacteria.

TABLE 6

Primer sequences for PCR screening of *Lactococcus lactis*

| # | Primer | Specificity | Amplicon size (bps) | 5'-Sequence-3' | Ref |
|---|--------|-------------|---------------------|----------------|-----|
| 1 | LL1 | *Lactococcus lactis* | 142 | F: AGC AGT AGG GAA TCT TCG GCA (SEQ ID NO: 3)<br>R: GGG TAG TTA CCG TCA CTT GAT GAG (SEQ ID NO: 4) | I |
| 2 | LL2 | *Lactococcus lactis* | 126 | F: TGA AGA ATT GAT GGA ACT CG (SEQ ID NO: 5)<br>R: CAT TGT GGT TCA CCG TTC (SEQ ID NO: 6) | — |
| 3 | LL3 | *Lactococcus lactis* | 387 | F: GTT GTA TTA GCT AGT TGG TGA GGT AAA (SEQ ID NO: 7)<br>R: GTT GAG CCA CTG CCT TTT AC (SEQ ID NO: 8) | II |
| 4 | lactis1 | subspecies *lactis* | 78 | F: TGT CAC AAG CCA TGC G (SEQ ID NO: 9)<br>R: CAC GCA ATT GGT TGA AAA (SEQ ID NO: 10) | — |

TABLE 6-continued

Primer sequences for PCR screening of *Lactococcus lactis*

| # | Primer | Specificity | Amplicon size (bps) | 5'-Sequence-3' | Ref |
|---|--------|-------------|---------------------|----------------|-----|
| 5 | lactis2 | subspecies *lactis* | 254 | F: TTA ATT CAA CCT GGA GAC ACA GTC TTA G (SEQ ID NO: 11)<br>R: CTA TCA GCG ATT TCA CGG AAC TTA G (SEQ ID NO: 12) | III |
| 6 | cremoris | subspecies *cremoris* | 241 | F: GAT GAA GAT TGG TGC TTG CAC CAA TTT GAA GAG (SEQ ID NO: 13)<br>R: CCT CTC AGG TCG GCT ATG TA (SEQ ID NO: 14) | IV |
| 7 | citP | subsp. *lactis* biovar *diacetylactis* | 616 | F: GGA GTT GGT GCT GGT ATT GTG (SEQ ID NO: 15)<br>R: CTG CTA TTA CAG GGT TGG (SEQ ID NO: 16) | V |

References:
I. Zhang, et al. (2016), *The ISME journal* 10(9): pages 2235-2245.
II. Odamaki, et al. (2011), *Letters in Applied Microbiology*, 52(5): pages 491-496.
III. van Mastrigt et al. (2018), *BMC Genomics*, 19(1): pages 1-19.
IV. Grattepanche, et al. (2005), *Applied Microbiology and Biotechnology*, 66(4): pages 414-421.
V. Klijn et al. (1995), *Applied and Environmental Microbiology*, 61(2): pages 788-792.

Catalase Activity Test

The catalase activity test was a second assay used for screening. *Lactococcus lactis* is catalase-negative and a negative result in this test permitted the elimination of false-positive results in PCR genotyping. Briefly, the active culture of the potential isolates was added to an equal volume of 3% $H_2O_2$. Generation of air bubbles following 5 minutes of incubation indicated that the sample was catalase positive.

Identification of *Lactococcus lactis* by Matrix-Assisted Laser Desorption-Ionization Time of Flight Mass Spectrometry (MALDI-TOF MS)

The MALDI-TOF MS was performed by the Veterinary Diagnostic Laboratory of the City University of Hong Kong. Briefly, following PCR genotyping and catalase activity tests, potential isolates were cultured on agar plates for 24 hours at 37° C. Colonies on the plate were then selected, isolated, and tested using MALDI-TOF mass spectrometry (MALDI Biotyper®, Bruker, Massachusetts, United States). The mass spectra of individual colonies were matched against the Biotyper reference library to identify the microbial colonies.

Results

*Lactococcus* Isolates Identified in Mouse Stool Samples

The stool samples from the mice receiving the fecal microbiota transplant from a healthy human donor were screened for *Lactococcus lactis*. Following plating of the fecal microbial culture at day one on the BHI agar, two were identified as *Lactococcus* strains following screening by PCR genotyping and the catalase activity test. For the catalase activity assay, 3% $H_2O_2$ was added to the active culture. The generation of air bubbles indicated that the cultures in question had catalase activity. *Lactococcus lactis* is catalase negative. *E. coli* was used as a positive control for the catalase activity test. Two subspecies of *Lactococcus lactis*, the subspecies *cremoris* ATCC 19257 and the subspecies *lactis* bv. *diacetylactis* were also observed to be catalase negative. Also conducted was PCR amplification of isolates from the mice stool samples with primer pair (LL1) specific for *Lactococcus*. The lanes in the gel were loaded as follows: Lane 1, 50-bp DNA ladder (Invitrogen); Lane 2, positive isolates #1; Lane 3, positive isolates #2; Lane 4, positive control *L. lactis* ssp. *cremoris* ATCC 19257; Lane 5, positive control *L. lactis* ssp. *lactis* bv. *diacetylactis*; and Lane 6, negative control.

The two isolates (specified as Isolate #1 and Isolate #2) were then subjected to PCR genotyping to confirm that they were *Lactococcus* strains. Gel electrophoresis was conducted to confirm the species of the gut microbial isolates from mice receiving fecal microbiota transplant from a healthy human donor. PCR amplification using three sets of specific PCR primer for *L. lactis* and *L. lactis* subspecies *lactis* were used. The lanes of the gels were loaded as follows: Lane 1, 50-bp DNA ladder (Invitrogen); Lanes 2, 7 & 12, positive isolates #1; Lanes 3, 8 & 13, positive isolates #2; Lanes 4, 9 & 14, positive control *L. lactis* ssp. *cremoris* ATCC 19257; Lanes 5, 10 & 15, positive control *L. lactis* ssp. *lactis* bv. *diacetylactis*; Lanes 6, 11 & 16, negative control. The primer pair used were LL2; LL3 and *lactis*1 as listed in Table 6.

The subspecies of the *Lactococcus* isolates from the mice receiving fecal microbiota transplant from the health control was confirmed. PCR was carried out with DNA from the isolates with primer pairs specific to *L. lactis* ssp. *lactis* or specific to *L. lactis* ssp. *cremoris*. The lanes of the gel were loaded as follows: Lanes 1, 50-bp DNA ladder (Invitrogen); Lane 2 and 7, Isolates #1; Lanes 3 and 8, isolates #2; Lanes 4 and 9, *L. lactis* ssp. *cremoris* ATCC 19257; Lanes 5 and 10, *L. lactis* ssp. *lactis* bv. *diacetylactis*; Lanes 6 and 11, negative control. Both isolates were found to belong to subspecies *lactis* but not subspecies *cremoris* by using these tailored primer sets as described in Table 6.

The difference between the *Lactococcus* isolates by citrate permease gene was determined. PCR was conducted on the DNA from the isolates with the primer pair targeting the citrate permease (CitP) gene. CitP is responsible for transporting citrate into the bacterial cell and is indispensable for the bacteria to metabolize citrate. The ability to metabolize citrate also aids in distinguishing different subspecies of *Lactococcus*. *L. lactis* ssp. *cremoris* and *L. lactis* ssp. *lactis* are citP negative while *L. lactis* ssp. *lactis* bv. *diacetylactis* is citP-positive. The lanes of the gels were loaded as follows: Lanes 1, marker; Lane 2, isolates #1; Lane 3, isolates #2; Lane 4, *L. lactis* ssp. *cremoris* ATCC 19257; Lane 5, *L.*

*lactis* ssp. *lactis* bv. *diacetylactis*; and Lane 6, negative control. The two isolates were distinguished from each other by detecting the citrate permease (citP) gene. Isolate #1 was citP positive and isolate #2 was citP negative.

Apart from genotyping and biological properties, the identity of these two isolates were validated using MALDI-TOF MS typing. According to mass spectrum matching, the typing report indicated that both isolates were identified as *Lactococcus lactis* (Table 7 and Table 8). Tables 7 and 8 are representative MALDI-TOF reports for Isolate #1 and Isolate #2.

TABLE 7

MALDI-TOF Report for Isolate #1

| Rank (Quality) | Matched Pattern | Score Value | NCBI Identifier |
|---|---|---|---|
| 1 (+++) | *Lactococcus lactis* DSM 4366 DSM | 2.46 | 1358 |
| 2 (+++) | *Lactococcus lactis* DSM 20661 DSM_2 | 2.44 | 1358 |
| 3 (+++) | *Lactococcus lactis* ssp *lactis* DSM 20175 DSM | 2.39 | 1360 |
| 4 (+++) | *Lactococcus lactis* ssp *lactis* DSM 20661 DSM | 2.36 | 1360 |
| 5 (+++) | *Lactococcus lactis* ssp *lactis* DSM 20384 DSM | 2.31 | 1360 |
| 6 (+++) | *Lactococcus lactis* IBS_MS_6 IBS | 2.29 | 1358 |
| 7 (+++) | *Lactococcus lactis* DSM 30863 DSM | 2.28 | 1358 |
| 8 (+++) | *Lactococcus lactis* ssp *cremoris* DSM 20388 DSM | 2.22 | 1359 |

TABLE 8

MALDI-TOF Report for Isolate #2

| Rank (Quality) | Matched Pattern | Score Value | NCBI Identifier |
|---|---|---|---|
| 1 (+++) | *Lactococcus lactis* DSM 4366 DSM | 2.30 | 1358 |
| 2 (+++) | *Lactococcus lactis* DSM 20661 DSM_2 | 2.24 | 1358 |
| 3 (+++) | *Lactococcus lactis* ssp *lactis* DSM 20661 DSM | 2.22 | 1360 |
| 4 (+++) | *Lactococcus lactis* ssp *lactis* DSM 20175 DSM | 2.22 | 1360 |
| 5 (+++) | *Lactococcus lactis* DSM 30863 DSM | 2.20 | 1358 |
| 6 (+++) | *Lactococcus lactis* DSM 20834 DSM | 2.16 | 1360 |
| 7 (+++) | *Lactococcus lactis* spp *lactis* 3C1_QSA IBS | 2.08 | 1360 |
| 8 (+++) | *Lactococcus lactis* IBS_MS_6 IBS | 2.06 | 1358 |

*Lactococcus* Isolates Identified in Human Stool Samples

Seven *Lactococcus* isolates were identified from two healthy individuals using the same screening protocol as used in mice. The *Lactococcus* isolates were first confirmed by PCR and catalase activity test. Afterwards, the identities of the *Lactococcus* isolates were validated by MALDI-TOF MS typing (Table 9). Table 9 is a representative MALDI-TOF report for a *Lactococcus* isolate from a healthy human donor.

TABLE 9

Representative MALDI-TOF MS report for *Lactococcus* isolate from a healthy human donor.

| Rank (Quality) | Matched Pattern | Score Value | NCBI Identifier |
|---|---|---|---|
| 1 (+++) | *Lactococcus lactis* DSM 4366 DSM | 2.17 | 1358 |
| 2 (+++) | *Lactococcus lactis* DSM 20834 DSM | 2.06 | 1360 |
| 3 (+++) | *Lactococcus lactis* ssp *lactis* DSM 20661 DSM | 2.04 | 1360 |
| 4 (+++) | *Lactococcus lactis* DSM 20661 DMS_2 | 1.97 | 1358 |
| 5 (+++) | *Lactococcus lactis* DSM 30863 DSM | 1.96 | 1358 |
| 6 (+++) | *Lactococcus lactis* ssp *lactis* DSM 20175 DSM | 1.94 | 1360 |
| 7 (+++) | *Lactococcus lactis* spp *tructae* DSM 21502T DSM | 1.89 | 1358 |
| 8 (+++) | *Lactococcus lactis* spp *lactis* DSM 20481T DSM | 1.88 | 1360 |

We claim:

1. A method comprising:
   (a) measuring abundance or copy number of a microbial biomarker in a sample from a subject, wherein the subject is a human or non-human mammal, wherein the microbial biomarker comprises microbes from the *Lactococcus* genus or genus *Dorea*, and
   (b) administering to the subject a composition comprising *Lactococcus lactis* and/or *Dorea* sp. 5-2 when
      (i) the abundance of the microbial biomarker in the sample is less than half or about half of the abundance of the microbial biomarker in a healthy control, and/or
      (ii) the number of copies of the microbial biomarker DNA in the sample is about 20 copies/ng bacterial DNA or below 20 copies/ng bacterial DNA,
   wherein the amount of the *Lactococcus lactis* and/or *Dorea* sp. 5-2 administered is effective to treat non-alcoholic fatty liver disease (NAFLD) in the subject.

2. The method of claim 1, wherein measuring comprises a linear discriminant analysis (LDA) to measure abundance, a catalase activity test to measure the presence or absence of the catalase enzyme, and/or a quantitative PCR to measure copy number.

3. The method of claim 1, wherein measuring comprises a quantitative PCR (qPCR) reaction;
   wherein the qPCR reaction comprises a forward primer and a reverse primer for amplifying a microbial biomarker of *Lactococcus lactis*,
   wherein the forward primer for amplifying a microbial biomarker of *Lactococcus lactis* is selected from the group consisting of SEQ ID NO:1, SEQ ID NO:3, SEQ ID NO:5, and SEQ ID NO: 7; and
   wherein the reverse primer for amplifying a microbial biomarker of *Lactococcus lactis* is selected from the group consisting of SEQ ID NO:2, SEQ ID NO:4, SEQ ID NO:6, and SEQ ID NO: 8.

4. The method of claim 3, wherein the measuring further comprises a further qPCR reaction, wherein the further qPCR reaction comprises a forward primer and a reverse primer for amplifying a microbial biomarker of *Lactococcus lactis* subspecies *lactis*, wherein the forward primer for amplifying a microbial biomarker of *Lactococcus lactis* subspecies *lactis* is selected from the group consisting of SEQ ID NO:9 and SEQ ID NO:11; and wherein the reverse primer for amplifying a microbial biomarker of *Lactococcus lactis* subspecies *lactis* is selected from the group consisting of SEQ ID NO:10 and SEQ ID NO:12.

5. The method of claim 3, wherein the measuring further comprises a further qPCR reaction, wherein the further qPCR reaction comprises a forward primer and a reverse primer for amplifying a microbial biomarker of *Lactococcus lactis* subspecies *cremoris*, wherein the forward primer for amplifying a microbial biomarker of *Lactococcus lactis* subspecies *cremoris* is SEQ ID NO:13 and the reverse primer for amplifying a microbial biomarker of *Lactococcus lactis* subspecies *cremoris* is SEQ ID NO: 14.

6. The method of claim 3, wherein the measuring further comprises a further qPCR reaction, wherein the further qPCR reaction comprises a forward primer and a reverse primer for amplifying a microbial biomarker of *Lactococcus lactis* subspecies *lactis* biovar *diacetylactis*, wherein the forward primer for amplifying a microbial biomarker of *Lactococcus lactis* subspecies *lactis* biovar *diacetylactis* is SEQ ID NO:15 and the reverse primer for amplifying a microbial biomarker of *Lactococcus lactis* subspecies *lactis* biovar *diacetylactis* is SEQ ID NO: 16.

7. The method of claim 1, wherein microbial biomarker comprises *Lactococcus lactis* or *Dorea* sp. 5-2.

8. The method of claim 1, wherein the microbial biomarker in the subject is measured by detecting the number of copies of *Lactococcus lactis* DNA in the sample.

9. The method of claim 1, wherein the microbial biomarker in the subject is measured by detecting about 20 copies of *Lactococcus lactis* DNA per ng bacterial DNA or below 20 copies of *Lactococcus lactis* DNA per ng bacterial DNA in the sample.

10. The method of claim 1, wherein the microbial biomarker in the subject is measured by detecting between undetectable and about 20 copies of *Lactococcus lactis* DNA per ng bacterial DNA in the sample.

11. The method of claim 1, wherein the microbial biomarker comprises *Lactococcus lactis* strains or subspecies.

12. The method of claim 1, wherein the microbial biomarker comprises *Lactococcus lactis* subspecies (subsp.) selected from the group consisting of *L. lactis* subsp. *lactis*, *L. lactis* subsp. *cremoris*, and *L. lactis* subsp. *hordniae*.

13. The method of claim 1, wherein the microbial biomarker comprises *Lactococcus lactis* strains selected from the group consisting of CF102, 104, 109, MGYG-HGUT-00226, and *Lactococcus lactis*.

14. The method of claim 1, wherein the microbial biomarker comprises *L. lactis* subsp. *lactis* strain CF111 or 112.

15. The method of claim 1, wherein the subject has one or more diseases selected from the group consisting of metabolic syndrome, type 2 diabetes mellitus, cardiovascular disease (CVD), and chronic kidney disease (CKD).

16. The method of claim 1, wherein the healthy control is a subject free of one or more diseases selected from the group consisting of metabolic syndrome, type 2 diabetes mellitus, cardiovascular disease (CVD), and chronic kidney disease (CKD).

17. The method of claim 1, wherein the composition comprises *Lactococcus lactis* at a relative abundance of about 30 copies of *Lactococcus lactis* DNA per ng bacterial DNA, or greater than about 30 copies of *Lactococcus lactis* DNA per ng bacterial DNA, as determined by quantitative polymerase chain reaction (qPCR).

18. The method of claim 1, wherein the composition comprises between $1.0 \times 10^{11}$ to $1.0 \times 10^{13}$ colony forming units (CPU) of the microorganisms per ml of the composition or per mg of the composition.

19. The method of claim 1, wherein the composition is a fecal microbial transplant.

20. The method of claim 1, wherein the composition comprises *Dorea* sp. 5-2 at a relative abundance of between about 3% and 6%, as measured by linear discriminant analysis (LDA).

21. The method of claim 1, wherein the composition comprises *Lactococcus lactis* at a relative abundance of between about 30% and 60%, as measured by LDA.

\* \* \* \* \*